United States Patent
Allen et al.

(10) Patent No.: US 12,336,729 B2
(45) Date of Patent: Jun. 24, 2025

(54) TISSUE ENGAGEMENT DEVICES, SYSTEMS, AND METHODS

(71) Applicant: PATVJA One, LLC, Eden Prairie, MN (US)

(72) Inventors: John J. Allen, Mendota Heights, MN (US); Andreas C. Pfahnl, Eden Prairie, MN (US)

(73) Assignee: PATVJA ONE, LLC, Eden Prairie, MN (US)

( * ) Notice: Subject to any disclaimer, the term of this patent is extended or adjusted under 35 U.S.C. 154(b) by 56 days.

(21) Appl. No.: 17/494,816

(22) Filed: Oct. 5, 2021

(65) Prior Publication Data

US 2022/0022907 A1  Jan. 27, 2022

Related U.S. Application Data

(63) Continuation of application No. 16/149,371, filed on Oct. 2, 2018, now abandoned, which is a continuation
(Continued)

(51) Int. Cl.
*A61B 17/32* (2006.01)
*A61B 17/34* (2006.01)

(52) U.S. Cl.
CPC .......... *A61B 17/32* (2013.01); *A61B 17/3478* (2013.01); *A61B 2017/320044* (2013.01); *A61B 2017/3488* (2013.01)

(58) Field of Classification Search
CPC .............. A61M 25/0067; A61B 17/32; A61B 17/3478; A61B 2017/320044; A61B 2017/3488
See application file for complete search history.

(56) References Cited

U.S. PATENT DOCUMENTS 4,222,380 A    9/1980  Terayama
5,364,408 A *  11/1994 Gordon ............ A61B 17/06066
                                                  606/139
(Continued)

FOREIGN PATENT DOCUMENTS

EP    2179698 A1    4/2010
WO    9405213 A1    3/1994
(Continued)

OTHER PUBLICATIONS

The extended European Search Report rendered by the European Patent Office for European Patent Application No. 16740670.1 (regional phase of PCT application No. PCT/US2016/014114), dated Jul. 26, 2018, 10 pages.
(Continued)

*Primary Examiner* — Brooke Labranche
(74) *Attorney, Agent, or Firm* — Skaar Ulbrich Macari, P.A.

(57) ABSTRACT

Devices and related methods to engage tissue layers to access the space between the layers are provided. The access devices include engagement arms that can be deployed and retracted to easily engage the top tissue layer and allow it to be separated from the underlying layer. The engagement arms are coupled to an actuation rod that is in turn coupled to a switch or lever that allows a user to control the actuation from outside the patient. The engagement arms and coupling to the actuation rod are unique and compact to ensure the entire mechanism fits in a small diameter shaft.

23 Claims, 45 Drawing Sheets

Related U.S. Application Data of application No. 15/002,349, filed on Jan. 20, 2016, now abandoned.

(60) Provisional application No. 62/242,257, filed on Oct. 15, 2015, provisional application No. 62/221,011, filed on Sep. 19, 2015, provisional application No. 62/105,289, filed on Jan. 20, 2015.

(56) References Cited

U.S. PATENT DOCUMENTS

| | | | |
|---|---|---|---|
| 8,128,593 | B2 | 3/2012 | Kassab et al. |
| 11,627,951 | B2 | 4/2023 | Muse et al. |
| 2001/0016754 | A1 | 8/2001 | Adams et al. |
| 2007/0049968 | A1* | 3/2007 | Sibbitt .............. A61B 17/0057 606/213 |
| 2010/0105981 | A1* | 4/2010 | Ho ..................... A61B 17/3478 600/104 |
| 2010/0160719 | A1 | 6/2010 | Kassab et al. |
| 2010/0168761 | A1 | 7/2010 | Kassab et al. |
| 2011/0082339 | A1 | 4/2011 | Elliott, III |
| 2012/0330184 | A1 | 12/2012 | Mahapatra et al. |
| 2013/0006288 | A1 | 1/2013 | Callas et al. |
| 2013/0085388 | A1 | 4/2013 | Stangenes et al. |
| 2013/0274782 | A1 | 10/2013 | Morgan |
| 2013/0310833 | A1 | 11/2013 | Brown et al. |
| 2014/0058371 | A1 | 2/2014 | Krishnan |
| 2014/0277056 | A1 | 9/2014 | Poore et al. |
| 2014/0364901 | A1 | 12/2014 | Kiser et al. |
| 2015/0025560 | A1 | 1/2015 | Alhumaid |

FOREIGN PATENT DOCUMENTS

| | | |
|---|---|---|
| WO | 2013190967 A1 | 12/2013 |
| WO | 2014117087 A1 | 7/2014 |
| WO | 2016118616 A1 | 7/2016 |

OTHER PUBLICATIONS

Office Action to the corresponding European Patent Application No. 21159431.2 rendered by the European Patent Office (EPO) on Jul. 29, 2024 8 pages.

The extended European Search Report rendered by the European Patent Office for European Patent Application No. 21159431.2, dated Jul. 7, 2021, 10 pages.

* cited by examiner

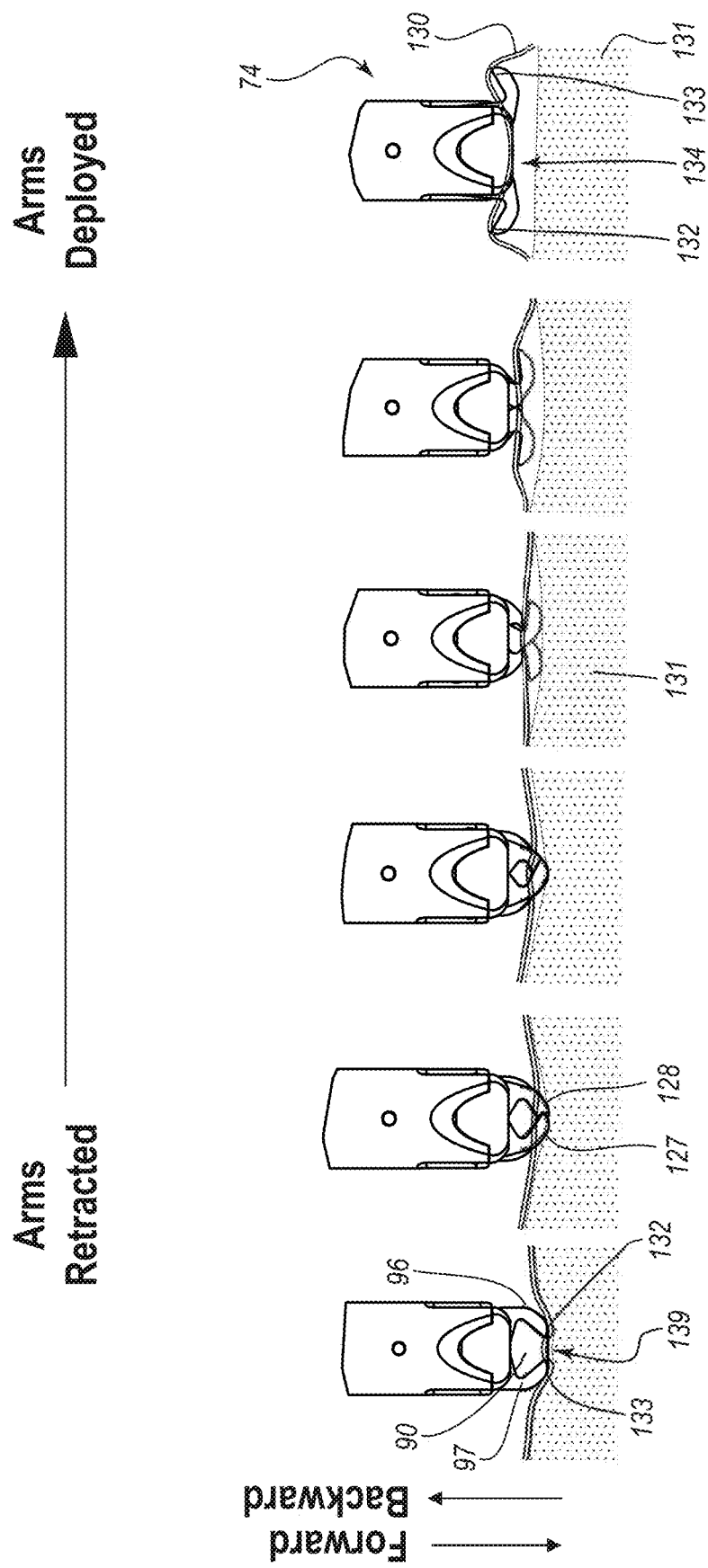

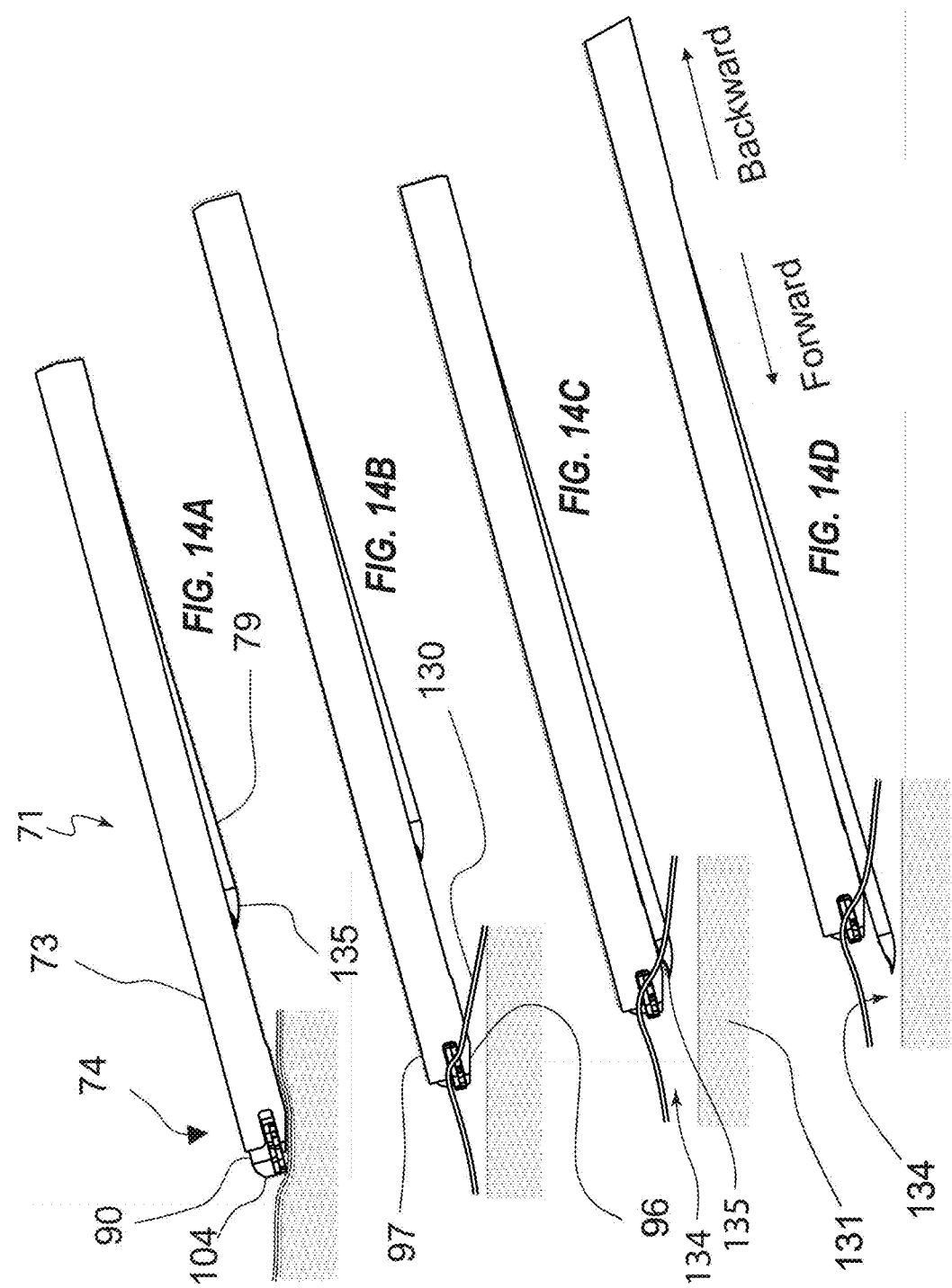

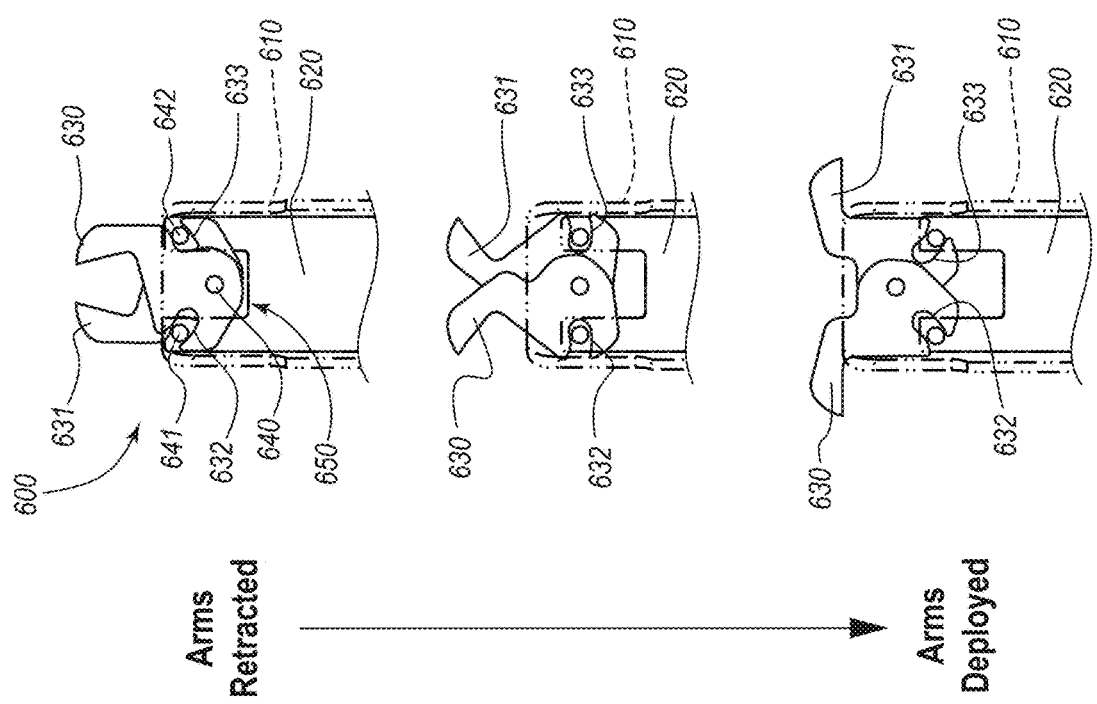

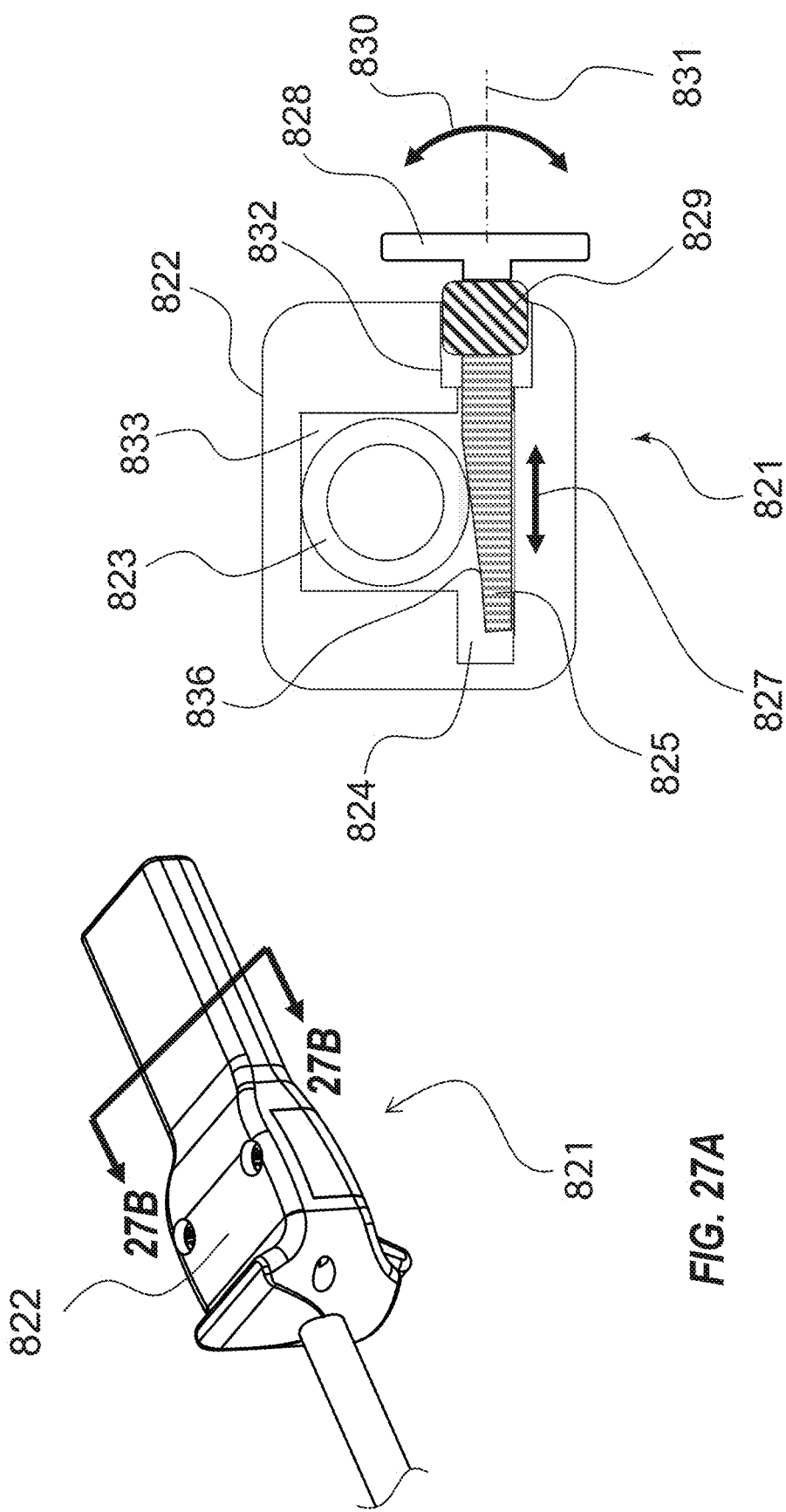

TISSUE ENGAGEMENT DEVICES, SYSTEMS, AND METHODS

CROSS-REFERENCE TO RELATED APPLICATIONS

This application is a continuation of U.S. patent application Ser. No. 16/149,371, filed on Oct. 2, 2018, titled TISSUE ENGAGEMENT DEVICES, SYSTEMS, AND METHODS, which is a continuation of U.S. patent application Ser. No. 15/002,349, titled TISSUE ENGAGEMENT DEVICES, SYSTEMS, AND METHODS, filed on Jan. 20, 2016, which claims the benefit under 35 U.S.C. § 119(e) of U.S. Provisional Patent Application No. 62/105,289, titled TISSUE ENGAGEMENT SYSTEM AND METHOD, filed on Jan. 20, 2015, U.S. Provisional Patent Application No. 62/221,011, titled TISSUE ENGAGEMENT SYSTEM AND METHOD, filed on Sep. 19, 2015, and U.S. Provisional Patent Application No. 62/242,257, titled TISSUE ENGAGEMENT SYSTEM AND METHOD, filed on Oct. 15, 2015, the entire contents of each of which are hereby incorporated by reference herein.

TECHNICAL FIELD

The present disclosure relates generally to systems, devices and methods for separating one tissue layer from underlying tissue or material. More specifically, the present disclosure relates to devices and methods for accessing the space between a tissue layer and an underlying structure, such as the pericardial space.

BACKGROUND

In the field of cardiac medicine, minimally invasive therapies for treating conditions at the heart's surface, or epicardium, have been developed or contemplated. Example treatments include epicardial ablation, left atrial appendage ligation, lead placement, and drug delivery. An important element of these procedures is safely gaining access to the pericardial space through the pericardium, which is a thin, protective, multi-layer membrane surrounding the heart. As described in the book Basic Human Anatomy—A Regional Study of Human Structure by O'Rahilly et al (reference FIG. 23-1), the outermost layer is the fibrous pericardium and the inner surface facing the pericardial space is a serous membrane called the parietal layer or pericardium. Opposing the parietal pericardium is another serous membrane called the visceral layer, which forms the outer surface of the epicardium. The pericardial space between the visceral and parietal layers is a thin film of serous fluid that provides lubrication. Because of its close proximity to the epicardium, creating an access port through the very thin pericardium can be difficult without injuring the underlying epicardium, heart muscles (myocardium tissue) and other structures such as blood vessels and nerves. The movement of the beating heart, breathing motions, presence of fatty surface tissue on the external surface of the fibrous pericardium, and toughness of the pericardium are some of the additional factors that can increase access difficulty.

Non-minimally invasive ways are considered surgical methods and use a thorascope to create an opening in the pericardium called a pericardial window. Presently, the accepted minimally invasive method for accessing the pericardial space between the pericardium and epicardium for purposes other than draining effusions (pericardiocentesis) involves carefully inserting a needle with fluoroscopic guidance as described by Sosa E., Scanavacca M., D'Avila A., and Pilleggi F. in "A New Technique to Perform Epicardial Mapping in the Electrophysiology Laboratory" in J Cardiovasc Electrophysiol., Vol. 7, pp. 531-536, June 1996. The procedure today is still performed with a commercially available Tuohy needle (typically 17 G or 18 G) that accommodates a standard 0.035" guide wire. St. Jude Medical has a general Epicardial Kit that includes different devices to perform epicardial procedures and a 17 G Tuohy needle for access. More recently, some epicardial access procedures are being performed with a 21 G Micropuncture needle which, because of the much smaller diameter, is more benign to unintended heart puncture, but very difficult to use because it is less stiff and requires exchanging to a larger, more stable 0.035" guide wire. Micropuncture needle kits are commercially available from a number of different manufacturers. Using either needle type requires a high degree of skill and practice, and can be very time-consuming, and therefore this procedure has not been widely adopted, limiting the use of emerging epicardial therapies. Some known procedures utilize needles enhanced with electrical measurement capability or ultrasound to better monitor the needle tip position during entry into the pericardial space.

It has been recognized that passing a needle through the pericardium could be made safer and less difficult by creating greater separation between the pericardium and epicardium. This has been demonstrated by the procedure known as pericardiocentesis, a procedure for draining excess fluid from the pericardial space. In this situation, the excess fluid creates pressure that forces the pericardium outward allowing safer needle passage. Various known methods to create this separation use vacuum apparatus, adhesion, or mechanical means (such as jaws or protruding needles). Further, some known devices for engaging tissue using needle-like members that bend or rotate into tissue. Known devices for engaging tissue or for creating a greater separation between the pericardium and epicardium suffer from a variety of drawbacks, however, as will be apparent from the disclosure herein. These limitations can be ameliorated or eliminated by embodiments disclosed hereafter.

SUMMARY

Certain embodiments disclosed herein include a mechanical engagement device that is sized to fit within a small opening such as a hypodermic tube. In some implementations, the engagement device consists of one or more small pivotable (e.g., pivotally mounted) arms with penetrating tips that engage tissue and bypass one another as they superficially pierce into the tissue. When fully actuated, the arms are positioned in such a way as to securely hold the tissue like hooks, allowing subsequent tissue manipulation such as lifting, pushing, pulling, or twisting. Lifting, for example, can create separation between the tissue and underlying layer or body of tissue beneath it. The pivotable arms can be sized and actuated to pierce into only the top layer of the tissue while minimizing the likelihood of injury or a puncture to the underlying layer. In some instances, this mechanism can be advantageous over existing devices and techniques in its ability to selectively engage thin tissue. In other or further instances, the device may be more robust to varying conditions, such as, for example, tissue thickness, toughness, and the presence of interfering tissue, such as fat.

Some embodiments advantageously facilitate passage of a needle to the arms and beyond, e.g., via a channel or conduit along a length of the device. The channel is located so that the needle can pierce the tissue layer in close proximity to the arms and in a way that makes advantageous use of the tissue traction from the tip of the engagement device. After the needle has passed through the tissue it may be used to perform additional procedural steps such as the introduction of a guide wire, injection of fluids such as imaging contrast agents or drugs, introduction of diagnostic or therapeutic devices, and the like.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 13A-13F depict the tip of the tissue engagement device engaging a tissue layer, with the stages of deployment of each of FIGS. 13A-13F corresponding with the six stages of deployment depicted in each of FIGS. 11 and 12.

FIG. 14A depicts a side view of the tissue engagement device engaging a tissue layer at a shallow angle.

FIG. 14B depicts a side view of the tissue engagement device pulling the tissue layer back.

FIG. 14C depicts a side view of the tissue engagement device deploying a puncture needle through the tissue layer.

FIG. 14D depicts a side view of the puncture needle being advanced into the pericardial space.

FIG. 25C depicts detailed sequential views of the tip of a still further embodiment of a tissue engagement device in which an actuation rod is pulled relative to a shaft to deploy the engagement arms, which are pivotally mounted to the shaft.

FIG. 27A is a perspective view of an embodiment of a handle for a tissue engagement device that includes an adjustable needle brake.

FIG. 27B is a cross-sectional view of the handle taken along the view line 27B-27B in FIG. 27A.

DETAILED DESCRIPTION

Illustrative embodiments are described in the following with reference to the drawings. It should be understood that such embodiments are by way of example only and are merely illustrative of the many possible embodiments which can represent applications of the principles of the present disclosure. Various changes and modifications obvious to one skilled in the art to which the present disclosure pertains are deemed to be within the spirit, scope and contemplation of the present disclosure as further defined in the appended claims. The illustrative embodiments described herein are not intended to be exhaustive or to limit the disclosure to the precise forms disclosed in the following detailed description. Rather, the illustrative embodiments described herein are chosen and described so those skilled in the art can appreciate and understand the disclosed principles and practices.

The inventors have recognized that known devices and methods for accessing the pericardial space, such as those discussed in the Background above, have been unsuccessful and impractical in clinical use. For example, capital equipment and facility connections, such as for vacuum, are undesirable, increase cost, require maintenance, and take up space in generally crowded clinical labs. The required penetration angle can vary widely and be very shallow too (e.g. almost 0 degrees to almost 90 degrees, with shallow being around 30 degrees or less), and varying approaches to target anterior and inferior areas of the heart also make it difficult to engage the pericardium. Further, varying fat and loose connective tissue adjacent the pericardium interferes with engagement. Additionally, known devices are not designed specifically for engaging a tissue layer (versus a thicker mass of tissue like in lead anchoring devices) and do not have features for creating an access pathway for a guidewire or catheter type device into the potential space between the tissue layer being engaged and an underlying tissue layer. Embodiments disclosed herein address, ameliorate, or eliminate one or more of the foregoing limitations and/or other limitations of prior art devices. Certain devices and methods, for example, can reliably and safely separate the pericardium from the epicardium and facilitate passage of a needle or guidewire into the pericardial space.

Figure 1:
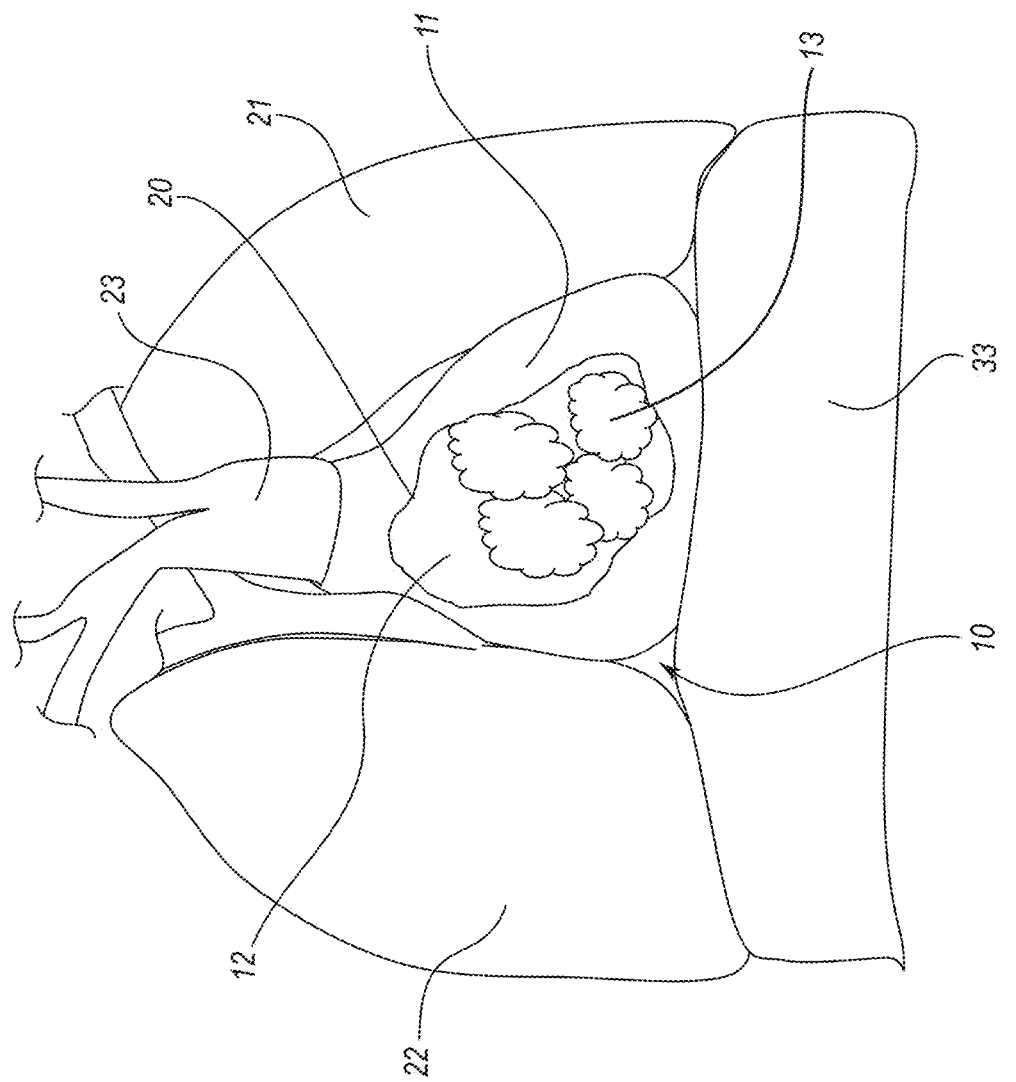
FIG. 1 is an anterior view of the thoracic cavity of a patient.

Referring to FIG. 1, an anterior view of the thoracic cavity, the pertinent anatomical structures such as the diaphragm 33, left lung 21, right lung 22, aorta 23, and heart 10 are shown. A portion 20 of the parietal pericardium 11 is cut away to so that the underlying epicardium 12 and epicardial fat 13 can be seen.

Figure 2:
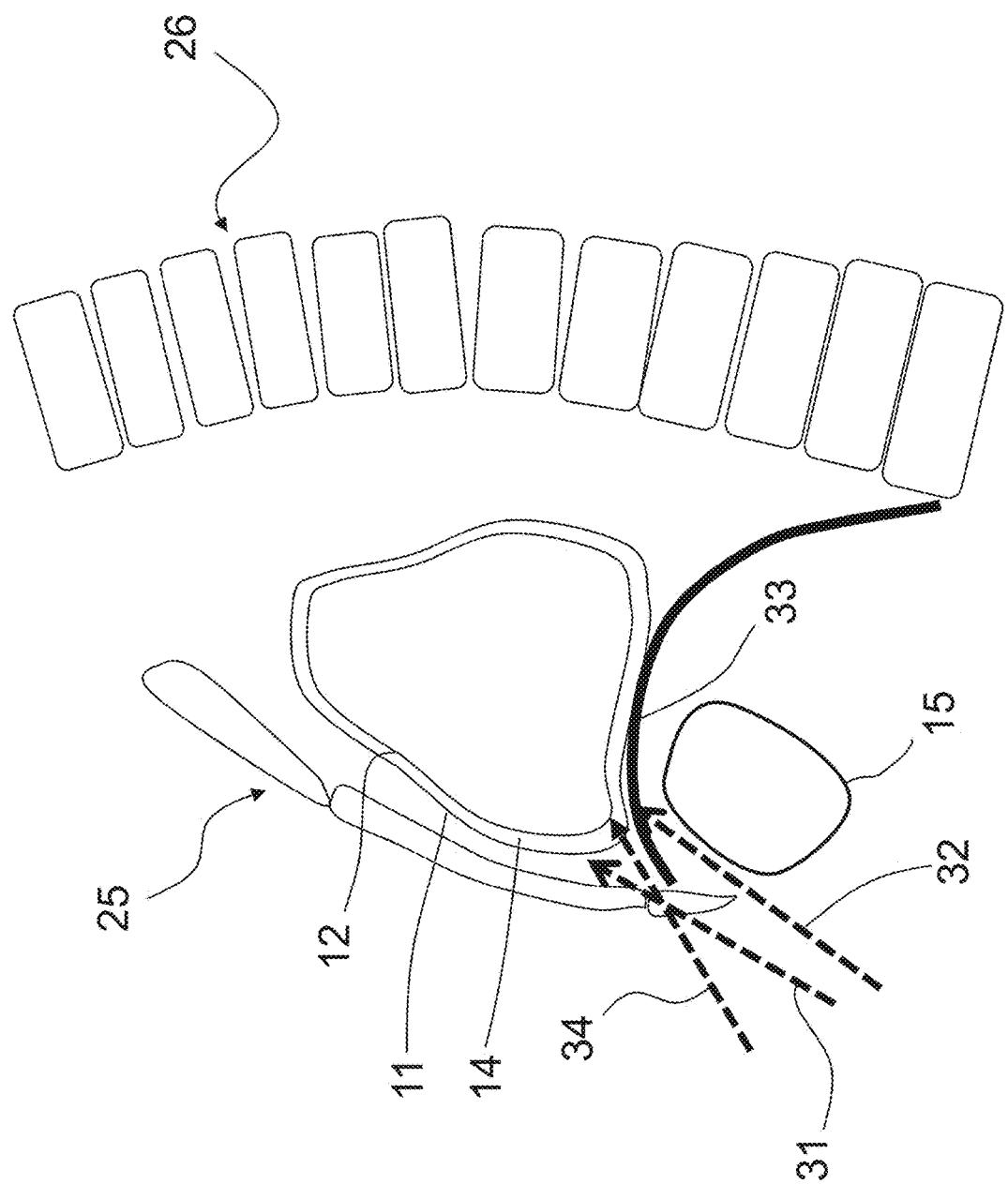
FIG. 2 illustrates a lateral view of the thoracic cavity of the patient.

Referring to FIG. 2, a midsection lateral view of the thoracic cavity is shown again showing the heart the pericardium 11 and further showing the epicardium 12, the pericardial space 14, and the liver 15. For additional reference the sternum 25 and spine 26 are shown. The pericardial space 14 exists between the pericardium 11 and the epicardium 12. Under normal conditions, the surfaces of the epicardium and pericardium enclose a potential space; thus there is minimal to no clearance between the two layers, as described by Swale M. et al, "Epicardial Access: Patient Selection, Anatomy, and a Stepwise Approach." The Journal 240 (2011). In this figure, an anterior approach 31 is depicted, which is a preferred pericardial access approach and one used most commonly today. This approach is called the anterior approach because it provides access into the pericardial space on the anterior side of the heart. In this figure, inferior approaches 32 and 34 are also shown, and provide access to the inferior side of the pericardial space 14. The inferior approach 32 requires passing through the diaphragm 33 and for this reason is also referred to as a transdiaphragmatic or subdiaphragmatic approach. Both the anterior approach and 31 and the inferior approach 34 are called subxiphoid approaches and differ in the angle to the heart.

Figure 3:
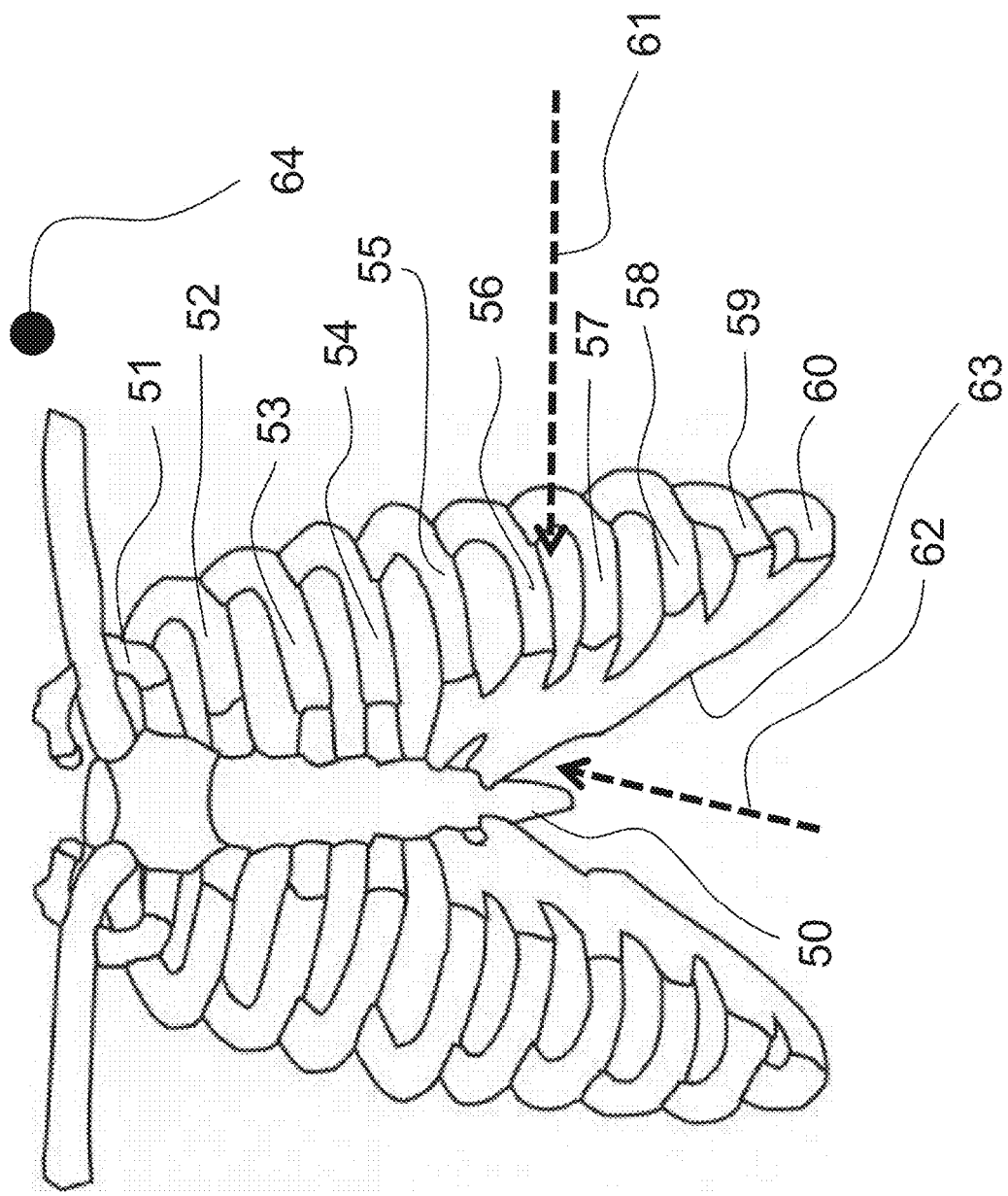
FIG. 3 illustrates a view of the chest of the patient and includes illustration of a subxiphoid approach.

FIG. 3 shows a view of the chest of a person with the xiphoid process 50 and the 1st costal 51 to the 10th costal 60 identified and numbered sequentially (i.e., the 2nd costal 52, 3rd costal 53, etc. through the 10th costal 60). An intercostal approach 61 shown here between the 6th and 7th ribs 56, 57 provides direct access to different areas of the heart. In this example, the intercostal space allows the apex of the heart to be accessed, and so such an approach is also called a transapical approach. Limitations to such an approach are the ability to eventually deliver and maneuver catheters because of the steep angle relative to the heart. The subxiphoid approach 62 is shown and its position relative to the xiphoid 50 and the costal margin 63. With the heart always positioned more to a person's left side the subxphoid approach 62 is angled towards the person's left shoulder area 64.

Figure 4:
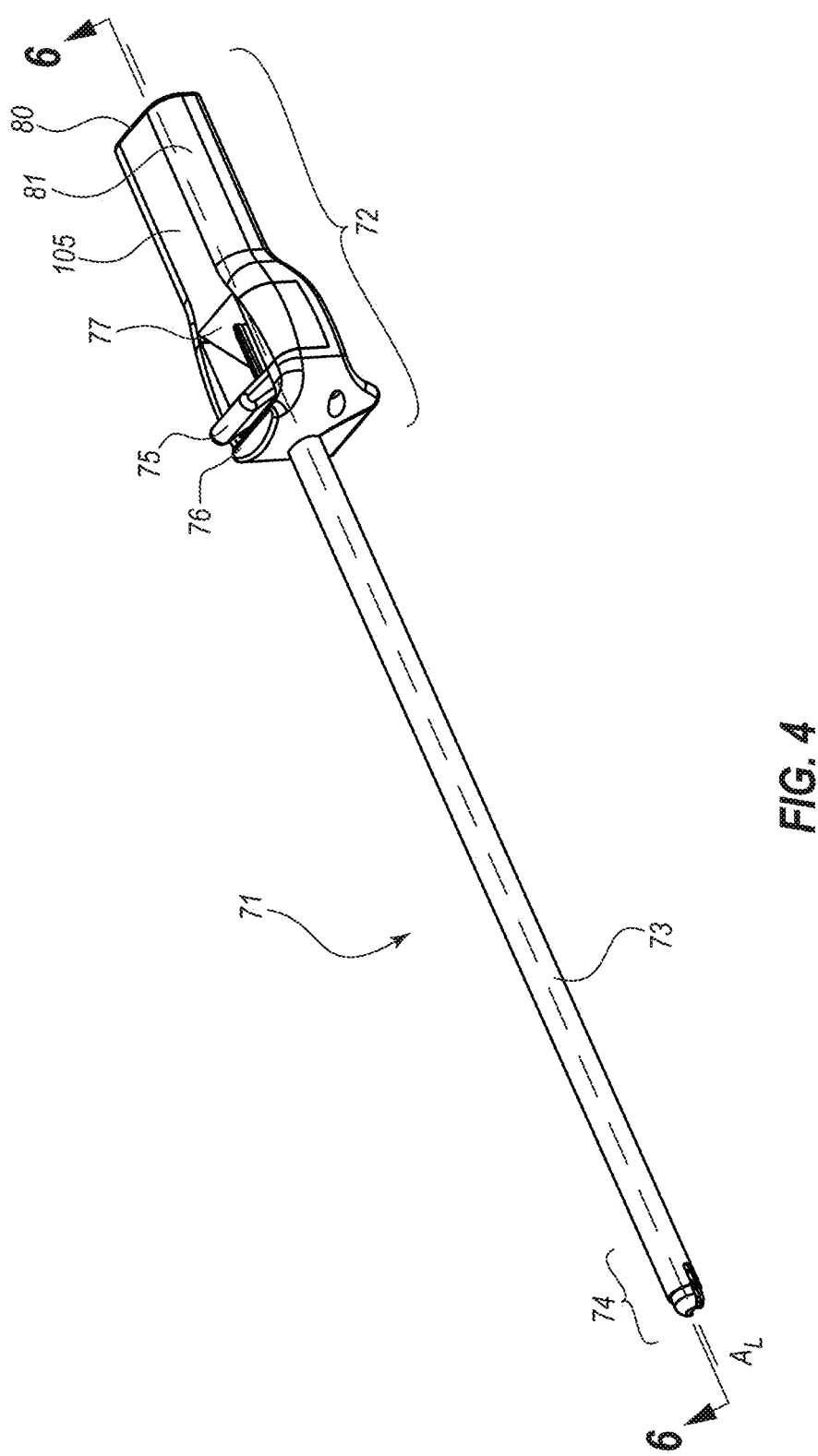
FIG. 4 shows a top side perspective view of an embodiment of a tissue engagement device in an undeployed or retracted state.
Figure 5:
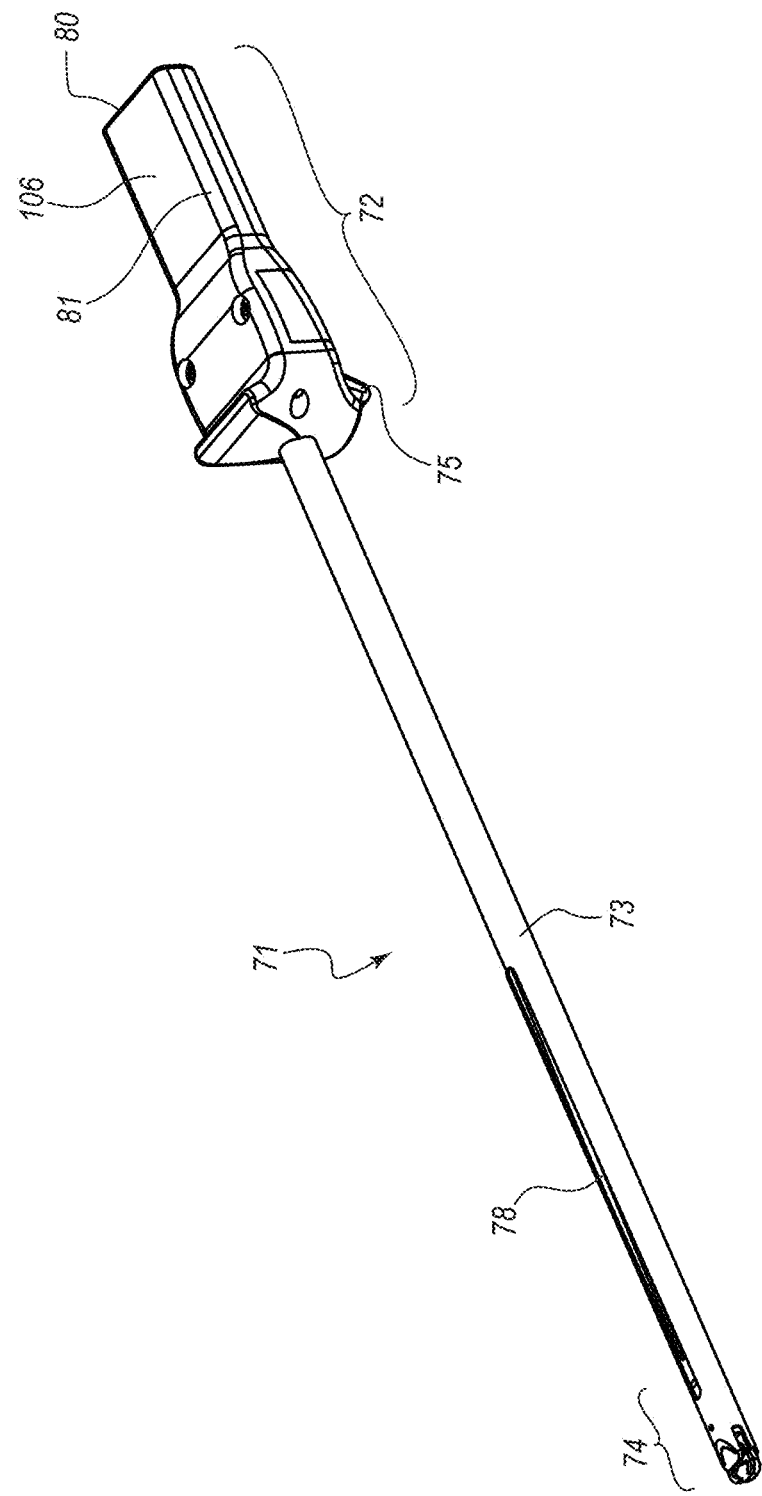
FIG. 5 shows a bottom side perspective view of the tissue engagement device in the undeployed state.
Figure 6:
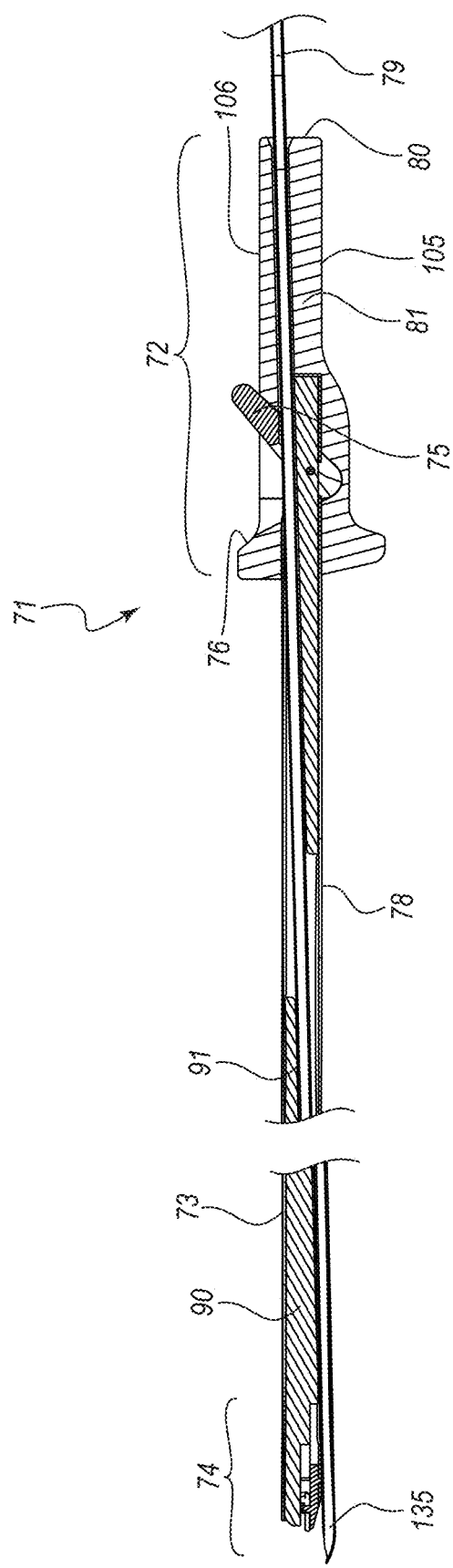
FIG. 6 shows a cross sectional view of the tissue engagement device taken along the view line 6-6 in FIG. 4, or stated otherwise, taken along a longitudinal axis of the device, that further depicts a puncture needle inserted through the device.

FIGS. 4 through 6 illustrate an embodiment of a tissue engagement device 71 which, referring to FIG. 4, has a handle 72, a tube 73 and a tip 74. The handle 72 has a main body 81 in which sits an actuation lever 75. In the illustrated embodiment, the actuation lever 75 extends from a top side 105 of the handle 72 and, more generally, the device 71. Lever 75 is shown in the forward position, which is when lever 75 is towards surface 76 of handle 72 and the engagement arms 96 and 97 (see FIG. 9) are retracted. A bottom side 106 of handle 72 and device 71 is shown in FIG. 5. The lever 75 can be switched to the rear position, which is when it is towards surface 77, as is also later shown in FIG. 7. A puncture needle 79, which has a tip 135, as shown in FIG. 6, enters through the proximal end 80 of the handle 72 and emerges through a slot 78. The slot 78 is part of a needle pathway 91. FIG. 4 also shows that in the illustrated embodiment, the tube 73 fits into a handle body 81. The puncture needle 79 is shown straight but can be alternatively curved along any portion, which can help bring the tip 135 closer to the tip 74 as the needle 79 is deployed.

Figure 7:
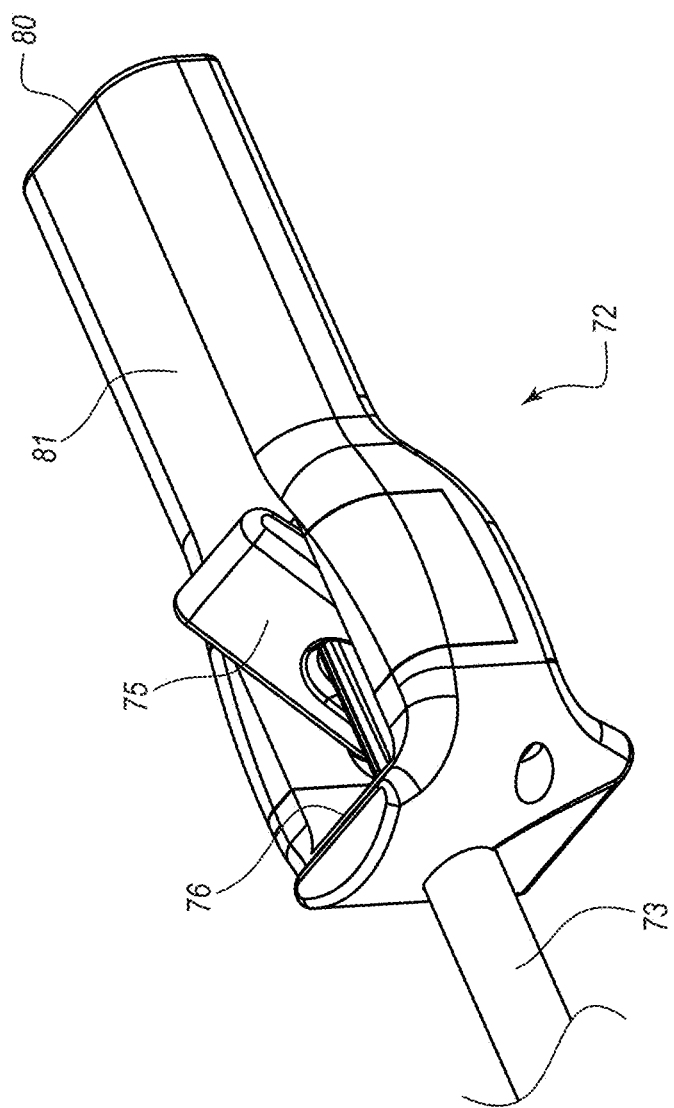
FIG. 7 is an enlarged perspective view of a proximal portion of the tissue engagement device that shows a handle and a lever that is positioned in a deployed state.

FIG. 7 is a detail view of the handle 72, showing where tube 73 enters the body 81. In this figure, lever 75 is switched to the rear position, which is when engagement arms 96 and 97 (see FIG. 9) are deployed.

Figure 8:
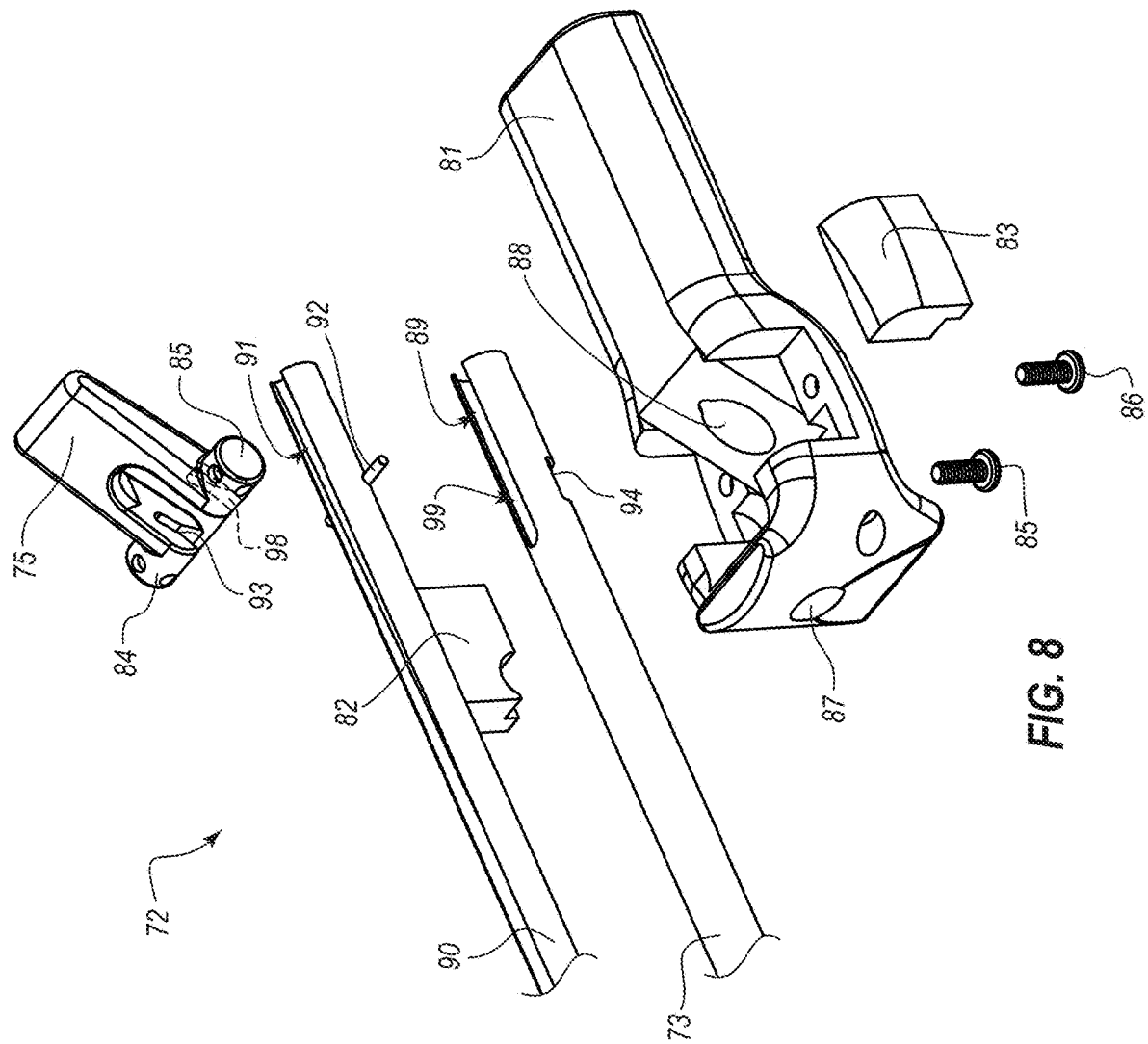
FIG. 8 shows an exploded perspective view of the portion of the tissue engagement device that is depicted in FIG. 7.

FIG. 8 is a perspective exploded view of the handle 72, which shows lever 75 and body 81. Covers 82 and 83 fit over the hubs 84 and 85 of lever 75. In this embodiment, the covers 82, 83 are held in place with screws 85 and 86 that pass through body 81, and thread into covers 82 and 83, respectively. The hubs 84 and 85 are received within recesses defined by the covers 82, 83 and the body 81 of the handle and are permitted to rotate therein. In this way, the lever 75 can pivot relative to the main body 81. Tube 73 fits into holes 87 and 88 of body 81 and is rigidly attached to body 81. In the illustrated embodiment, tube 73 defines a slot 89 at a proximal end thereof, which allows the puncture needle (see FIG. 6) to pass through. FIG. 8 also depicts an actuation rod 90 that defines a groove or needle pathway 91 and through which a pin 92 is pressed transversely. In the illustrated embodiment, actuation rod 90 fits inside of tube 73 and slides freely within. Stated otherwise, the tube 73 defines a lumen 99 that is sized to receive the actuation rod 90 therein. Stated otherwise, in some embodiments, the lumen 99 can define a maximum interior width that is larger than a maximum exterior width of the actuation rod 90. In the illustrated embodiment, the lumen 99 is sufficiently large to permit the actuation rod 90 to translate freely or within the tube 73. Lever 75 has grooves 93 and 98 that extend into the hubs 84 and 85 and are sized to receive respective ends of the pin 92 therein. In the illustrated embodiment, the pin 92 position is not on the same axis as the hubs 84 and 85, so that as lever 75 is pivoted it can move and control the position of actuation rod 90. Stated otherwise, in the illustrated embodiment, the pin 92 position is not restricted to a rotational axis of the hubs 84 and 85, or is capable of translating or otherwise moving relative to a rotational axis through the hubs 84, 85. Rotation of the lever 75, and thus of the hubs 84, 85, can result in a forward or rearward camming of the pin 92, which can translate the actuation rod 90 in a distal direction or a proximal direction, respectively. In order to accommodate the pin 92 motion, the tube 73 has a cutout 94.

Figure 9:
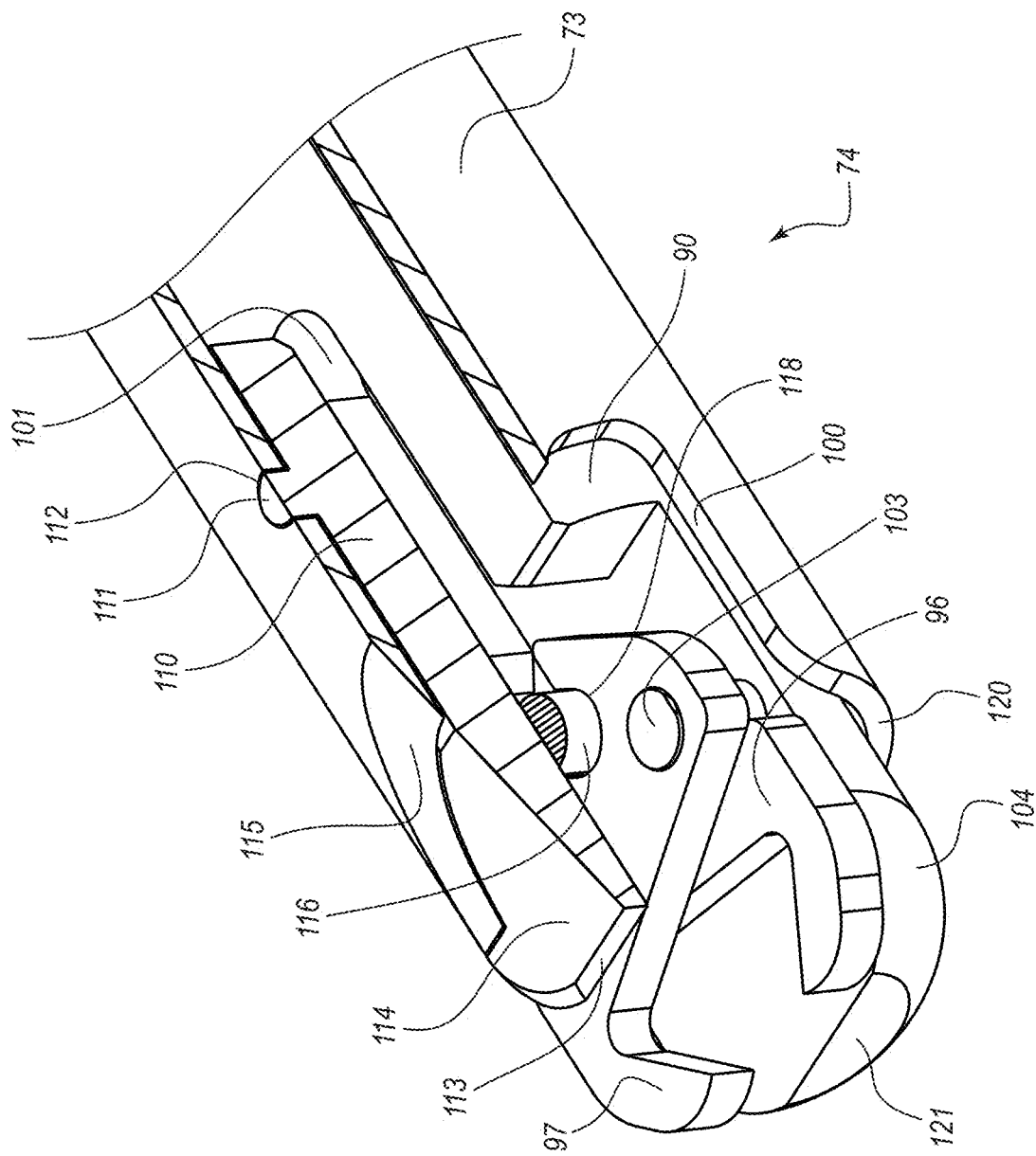
FIG. 9 shows a perspective view in partial cross-section of a tip of the tissue engagement device in the undeployed state.
Figure 10:
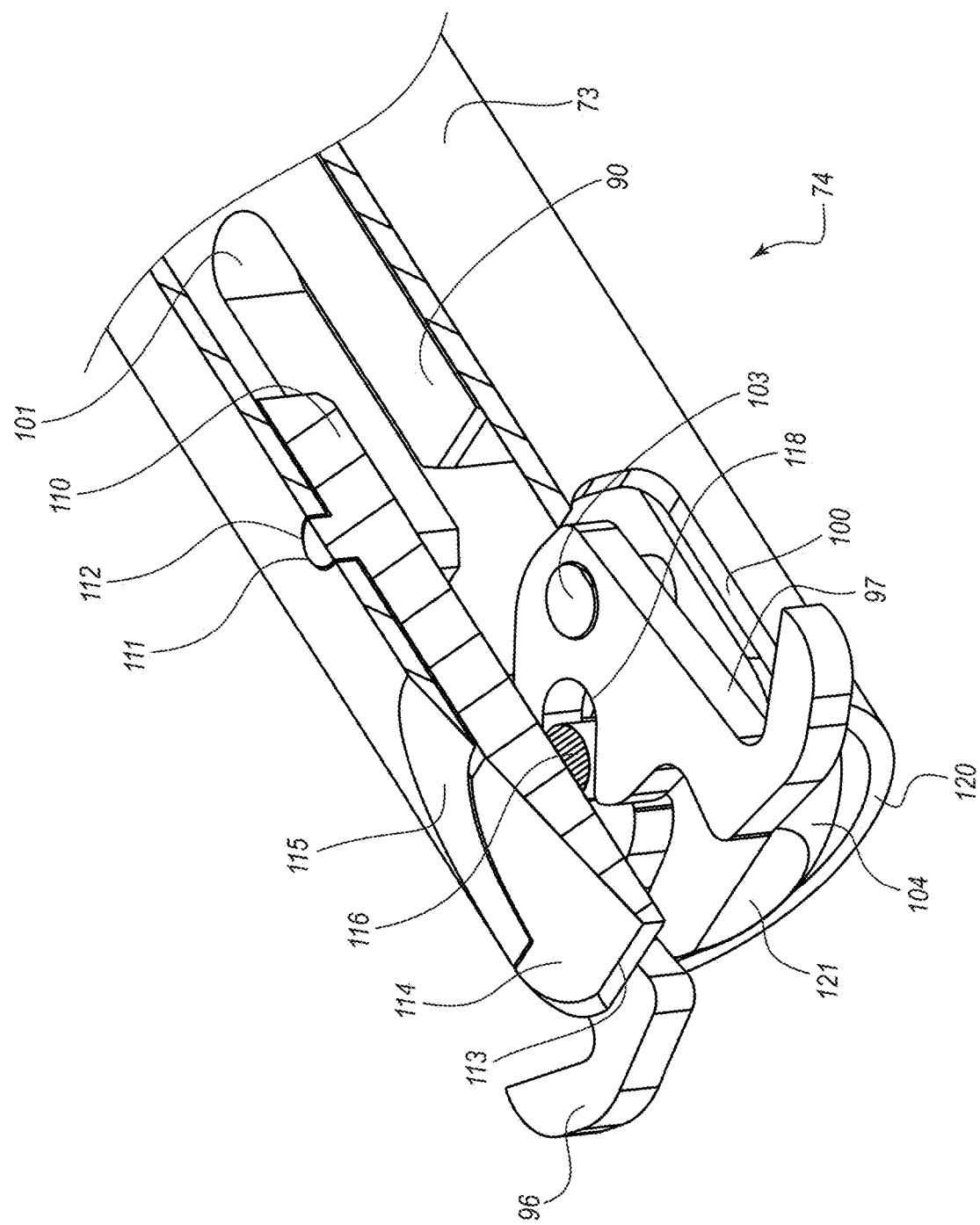
FIG. 10 shows a perspective view in partial cross-section of the tip of the tissue engagement device in the deployed state.

FIGS. 9 and 10 are close-up cutaway views of the tip 74 of the device 71 showing engagement arms 96 and 97 in their retracted and deployed positions, respectively. In the illustrated embodiment, the engagement arms lie directly adjacent or very close to each other. The tube 73 has slot 100 and is shown with the actuation rod 90 in place. Actuation rod 90 has tip 104, slot 101 and posts 102 and 103 on which the arms 96 and 97 are placed and each can pivot about. Guide 110 is shown with post 111 that fits into a hole 112 in tube 73 to hold it in place. In the embodiment shown, the tip 113 of guide 110 has a chamfered face 114 which aligns with the chamfered end 115 of tube 73. This chamfered face 114 is on the same side as the bottom side 106 identified in FIGS. 5 and 6. Stated otherwise, in the illustrated embodiment, the chamfered face 114 is at a bottom side of the device 71. Guide 110 also has guide post 116 extending from it. Arms 96 and 97 also have slots 117 and 118 (see also FIG. 16A) into which post 116 slides. Slots 100, which are positioned at opposite sides of the tube 73 in the illustrated embodiment, allow engagement arms 96 and 97 to pivot and extend beyond the external boundaries of tube 73 during deployment. Chamfered face 114 and chamfered end 115 allow arms 96 and 97 to be positioned and be moved more closely to a tissue layer when the angle between the tip 74 and the surface of the tissue layer to be engaged is shallow, as compared, for example, with an arrangement in which a transverse cross-sectional profile of the tube 73 and/or the guide 110 is not reduced or is unaltered along the distal end of the device 71. The chamfered face 114 and chamfered end 115 may be said to define an acute angle relative to the longitudinal axis $A_L$ of the device 73 (which is also a longitudinal axis of the tube 73, in the illustrated embodiment). This angled configuration can permit the chamfered faces 114, 115 to rest against a tissue layer (e.g., the layer 130 described below) while the tube 73 is at an acute angle relative to the tissue layer.

Now referring to FIG. 4, and FIGS. 6 through 10, as the lever 75 moves from its forward position shown in FIG. 4 to its rear position shown in FIGS. 6 and 7, the actuation rod 90 moves backwards from its position shown in FIG. 9 to its position shown in FIG. 10. Stated otherwise, as can be seen by comparing FIGS. 9 and 10, the actuation rod 90 is retracted into the tube 73. In FIG. 9, the tip 104 of the actuation rod 90 extends past a distal face 120 of the tube 73. In FIG. 10, a greater portion of the tip 104 has been drawn into an interior of the tube 73 and a distal face 121 of the tip 104 extends only slightly past the distal end of the tube 73 in an axial direction. In some embodiments, the tip 104 may be drawn fully into an interior of the tube 73 such that the distal face 121 of the tip 104 is either flush with or axially recessed relative to the distal face 120 of the tube 73. The lever 75 controls the actuation rod 90 motion because of how the two are connected together via the pin 92 and grooves 93 and 98 in which the pin 92 follows, as discussed previously. The backward movement of actuation rod 90 causes the arms 96 and 97 to pivot about posts 102 and 103 as the slots 117 and 118 of arms 96 and 97 interact with the fixed guide post 116. In particular, the slots 117, 118 follow along the fixed guide post 116 to cam the arms to the outstretched, deployed, or expanded configuration, as discussed further below. When the actuation rod 90 is fully retracted, then arms 96 and 97 are fully deployed, as shown in FIG. 10.

Figure 11:
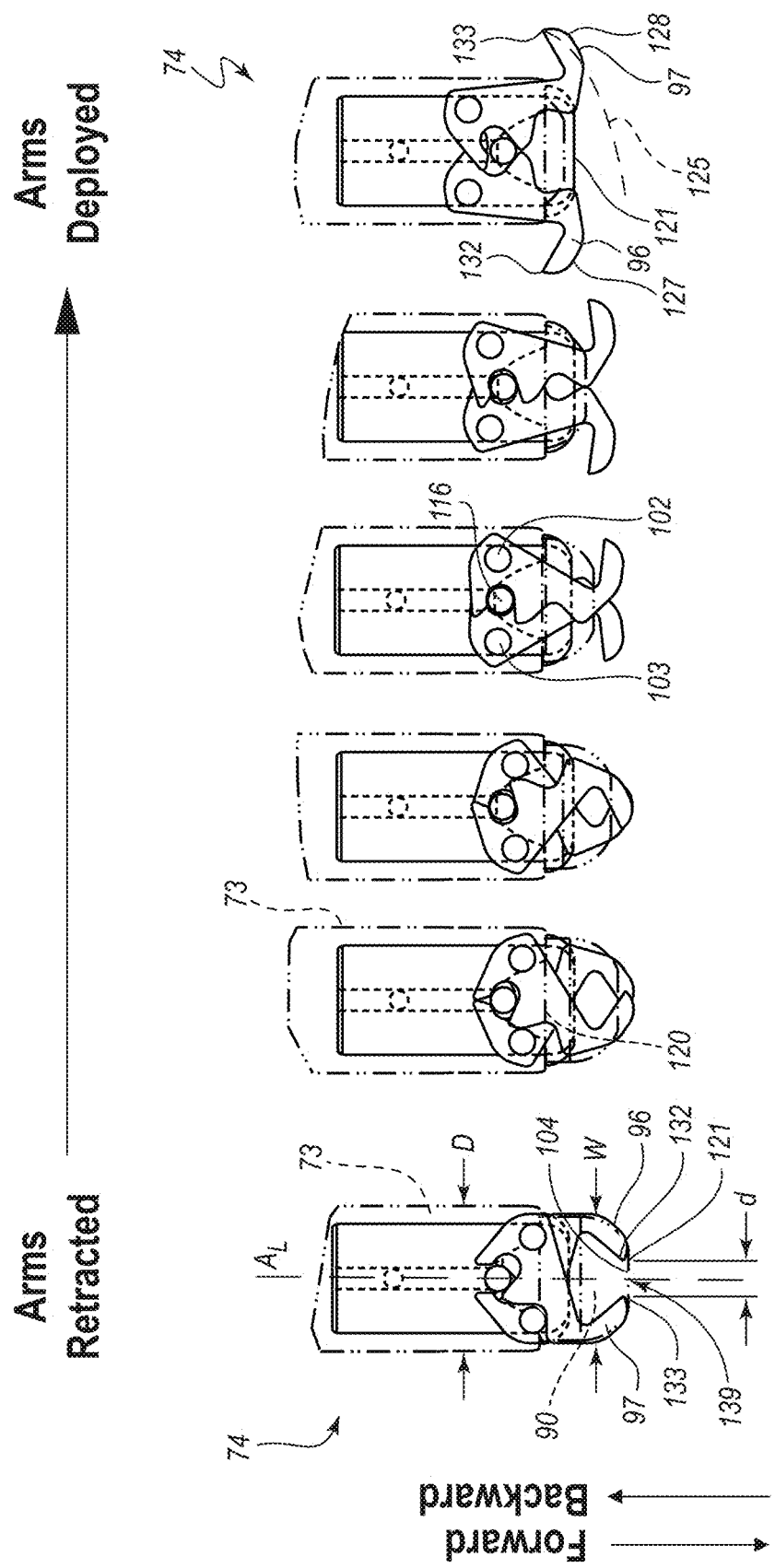
FIG. 11 depicts the tip of the tissue engagement device, with portions thereof reduced to broken lines for clarity, at various sequential stages of deployment.
Figure 12:
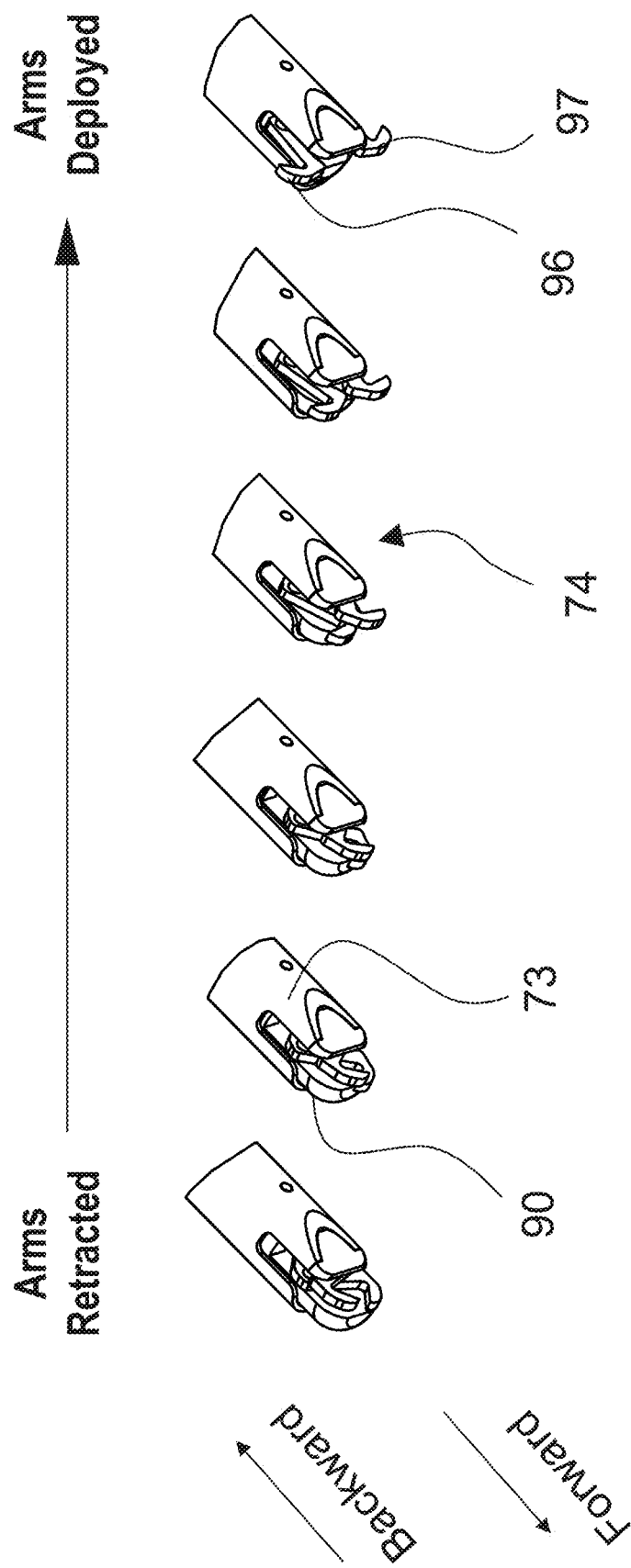
FIG. 12 shows perspective views of the same sequential stages of deployment of the tip of the tissue engagement device as those shown in FIG. 11.

FIGS. 11 and 12 further illustrate the deployment motion of tip 74, specifically showing tip 74 in different states or stages as actuation rod 90 is moved backward relative to the tube 73 to move arms 96 and 97 from their retracted or undeployed state to their deployed state. FIG. 11 shows side views of the distal portion of the device 71 in the different states, and FIG. 12 shows perspective views of the distal portion of the device 71 these same states. Each figure includes a legend identifying a forward (or distal) direction and a backward (or proximal) direction. In the retracted state, which corresponds with the leftmost orientation in FIGS. 11 and 12, the tip 104 is positioned in alignment with the penetrating tips 132 and 133 of arms 96 and 97. Stated otherwise, the penetrating tips 132, 133 the distal-most edges of the arms 96 and 97 are level or flush with the distal face 121 of the tip 104 of actuation rod 90 in the axial direction. Moreover, in the illustrated embodiment, the outer edges of the arms 96, 97 define a rounded profile that substantially matches (e.g., is substantially flush with) a rounded profile defined by the tip 104. When the arms 96, 97 are in the retracted or undeployed state, there is a close correspondence between an outline of the arms 96, 97 and an outline of the tip 104.

With continued reference to FIGS. 11 and 12, the outer profile defined by the moving arms 96, 97 extends outwardly beyond the profile of the tip 104 during deployment of the arms 96, 97. In the illustrated embodiment, the arms 96, 97 extend past the distal face 121 of the tip 104 in the axial direction throughout deployment as the actuation rod 90 is retracted. Indeed, in the illustrated embodiment, at least a portion of each arm 96, 97 is positioned distally relative to the distal face 121 of the tip 104 in each of the five stages or orientations depicted at the right side of FIG. 12.

A distance between the distal face 121 of tip 104 and the penetrating tips 132 and 133 of the arms 96, 97 can be controlled by changing the geometry of arms 96 and 97. For example, the penetrating tips 132 and 133 can be either distally beyond, in alignment with, or proximally retracted relative to the distal face 121 of the tip 104. Changing this relative distance can influence the depth to which the arms 96 and 97 penetrate into tissue as they are actuated. In certain embodiments, penetrating tips 132 and 133 are positioned proximal of the distal face 121 by a distance of between 0 inches and 0.030 inches when the arms are in the retracted state (e.g., the leftmost configuration in FIG. 11). It is contemplated that penetrating tips 132 and 133 could also be at different positions relative to each other (e.g., at different axial depths and/or radial distances from the longitudinal axis $A_L$ of the device 71). As arms 96 and 97 actuate from retracted to fully deployed, their penetrating tips 132 and 133 approach then bypass each other before stopping in positions radially extended from tube 73.

Referring now to FIGS. 11 and 13A-13F, in some embodiments, the tips 132, 133 of the arms 96, 97 define a gap or space d between them when the arms 96, 97 are in the undeployed state. As tip 104 is pressed against soft tissue, a bulge of tissue forms in space 139. The gap or space d can be sized such that a layer of thin tissue 130 will preferentially bulge into space 139 but underlying tissue 131 (i.e., a tissue layer that is beneath the tissue layer being engaged) will not. A transverse width of the space d may be customized for a specific application; for example, when used to engage perineal membrane with a thickness of 0.020 to 0.040 inches (0.5 to 1.0 mm), a width d is preferably twice the membrane thickness, or approximately 0.040 to 0.060 inches (1.0 to 2.0 mm). It is further contemplated that in some embodiments, the starting width of the space d may advantageously be zero or substantially zero; i.e., there is no gap between the tips 132, 133 when the arms 96, 97 are undeployed. In some embodiments, tips 132, 133 that do not define a space d in the retracted state may each be in alignment with the longitudinal axis $A_L$ of the device 71. In other embodiments, the space d is less than 0 inches when the arms 96, 97 are undeployed. Stated otherwise, the tips 132 and 133 may already be in a bypassed configuration when in the undeployed state.

Stated in yet another manner, in the illustrated embodiment, the tips 132, 133 face toward each other in the undeployed state that is depicted in the leftmost orientation of FIGS. 11 and 12 and in FIG. 13A. In this state, the tips 132, 133 are at opposite sides of the longitudinal axis $A_L$ of the device 71 and are directed inwardly (e.g., transversely inwardly or radially inwardly), and in the illustrated embodiment, are directed toward the longitudinal axis $A_L$. Stated otherwise, the tips 132, 133 may be said to face toward an imaginary longitudinal plane that passes through the longitudinal axis $A_L$. In the illustrated leftmost configuration of FIG. 11, the imaginary longitudinal plane is perpendicular to the plane of the page and extends through the longitudinal axis $A_L$. As the arms 96, 97 are transitioned to the deployed state, the tips 132, 133 move in opposite directions relative to the longitudinal axis $A_L$, or stated otherwise, relative to the longitudinal plane that extends through the longitudinal axis $A_L$. In the illustrated orientation, the arm 96 rotates in a clockwise direction to move the tip 132 substantially leftward and upward (e.g., proximally), and the arm 97 rotates in a counterclockwise direction to move the tip 133 substantially rightward and upward (e.g., proximally). In this manner, the arms 96, 97 rotate through the imaginary longitudinal plane and past each other. Stated otherwise, the tips 132, 133 bypass each other in opposite directions. In each of the second through sixth orientations depicted in FIGS. 11 and 12 (counting from left to right), and in FIGS. 13B-13F, the tips 132, 133 have bypassed each other and move progressively further away from each other. That is, even as of the second orientation of FIGS. 11 and 12 (counting from left to right) and as of the orientation of FIG. 13B, the tips 132, 133 have passed the longitudinal axis $A_L$ and move laterally, transversely, or radially outwardly and away from each other and from the longitudinal axis $A_L$. It may also be said that after the tips 132, 133 bypass each other, they face outwardly or face away from each other. They likewise may be said to face away from the longitudinal axis $A_L$ of the device 71. In the illustrated embodiment, the tips 132, 133 face each other, or face inwardly, in the undeployed state. In other embodiments, the tips 132, 133 can face away from each other, or face outwardly, in the undeployed state.

With reference to FIG. 11, in the retracted or undeployed state, the arms 96, 97 define an outer profile having a maximum lateral width W. In the illustrated embodiment, the width W is less than a maximum exterior width or diameter D defined by the tube 73. It is noted that the terms "diameter" and "tube" do not necessarily imply a cylindrical configuration of the tube 73. Although the illustrated embodiment of the tube 73 is substantially cylindrical, other suitable shapes and configurations of the tube 73 are contemplated. In the illustrated embodiment, when the device 71 is in the undeployed state, the size of the gap d is less than the maximum lateral width W of the arms 96, 97, which is smaller than the maximum exterior width D of the tube 73. The arms 96, 97 may thus have a smaller transverse profile than does the tube 73 when in the undeployed state.

As can be appreciated from the rightmost orientation in FIGS. 11 and 12 and from FIG. 13F, when the arms 96, 97 are fully deployed, the arms 96, 97 can have a larger transverse profile than the tube 73. Stated otherwise, the distance between the tips 132, 133 can be greater than the maximum exterior width D of the tube 73 when the arms 96, 97 are deployed.

With reference again to FIG. 11, in the illustrated embodiment, the tips 96, 97 are configured to move only in transverse and proximal directions relative to the tube 73. Stated otherwise, in the illustrated embodiment, throughout deployment of the arms 96, 97, the tips 132, 133 of the arms 96, 97 do not move distally relative to the tube 73. The rightmost depiction in FIG. 11 includes a path 125 that is traveled by the tip 133 during deployment of the arms 96, 97. The illustrated path 125 is arc shaped and may, in some instances, be substantially semicircular (other arc shapes may also be defined in further embodiments). Moreover, in tracing the arc-shaped path 125, no component of movement of the tip 133 is directed distally. Rather, the movement only includes rightward (transverse) and upward (proximal) components in the depicted orientation. Moreover, during the early stages of deployment, the movement is primarily transverse, whereas in later stages, the movement increasingly includes proximal components. The tip 132 traces a path having the same arc shape, but does so in the opposite transverse direction. However, the tips 132, 133 move in unison with each other in the proximal direction. In other embodiments, some amount of distal movement is possible for the tips 132, 133 during the early stages of deployment.

As can be appreciated from the foregoing discussion, and with additional reference to FIGS. 13A-13F, the paths traced by the tips 132, 133 during deployment can be well suited for engaging the thin tissue 130. For example, as previously mentioned, the gap 139 between the tips 132, 133 can receive a bunched portion of the thin tissue 130 therein when the distal end of the device 71 is pressed against the tissue layers 130, 131. As the tips 132, 133 are deployed, they initially move primarily in the transverse direction, or without moving toward the underlying tissue layer 131. Accordingly, the tips 132, 133 can engage the upper, thin tissue 130 without engaging the underlying tissue layer 131. As the tips 132, 133 continue along the arc-shaped paths through the later stages of deployment, the thin tissue 130 is further engaged by the arms 96, 97 and, with more proximally directed components of movement, is lifted away from the underlying tissue layer 131.

Figure 16A:
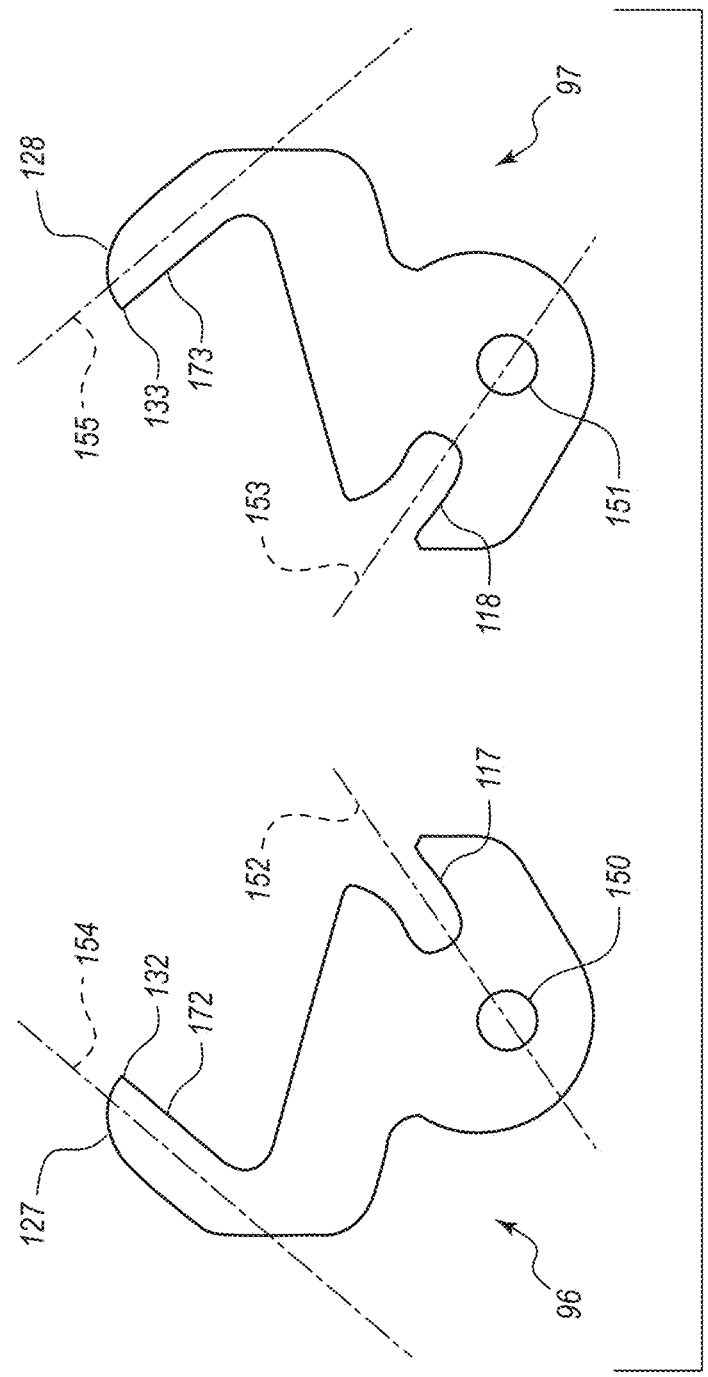
FIG. 16A is a detailed view of an embodiment of a single engagement arm.

With reference again to the rightmost depiction in FIG. 11, and with additional reference to FIG. 16A, the arms 96, 97 can define curved edges 127, 128, which may also be referred to as rounded sides, that extend from the tips 132, 133, respectively. With yet additional reference to FIGS. 13A-13F, as the tips 132, 133 move along the arc-shaped paths during deployment of the arms 96, 97, the curved edges 127, 128 can smoothly pass over the underlying tissue layer 131 without engaging this tissue. Stated otherwise, the curved edges 127, 128 can inhibit trauma to the tissue layer 131 tissue positioned beneath the layer 130 as the curved edges 127, 128 rotate against the tissue layer 131. In some embodiments, the curved edges 127, 128 face distally from the tissue engagement device 71 throughout an entirety of a transition from the retracted orientation to the actuated orientation to inhibit trauma to the additional tissue.

With reference again to FIGS. 11 and 12, mechanics of the deployment of the arms 96, 97 is further discussed. As the actuation rod 90 moves backward it moves the proximal portions of the arms 96 and 97 backwards relative to the guide 110 and the post 116. The grooves 117 and 118 of arms 96 and 97 follow along post 116, and cause arms 96 and 97 to pivot about posts 102 and 103. Stated otherwise, movement of the grooves 117, 118 relative to the post 116 causes the arms 96, 97 to cam or rotate in opposite directions. The motion of tip 104 relative to penetrating arm tips 132 and 133 (e.g., the amount of axial distance between the distal face 121 and the tips 132, 133) can be modified by changing the interaction between the pivots and groove 117 and 118 geometry. It is contemplated that design variations can include configurations in which the tip 104 moves axially faster or slower than the axial displacement of penetrating tips 132 and 133. It is also contemplated that the tip 104 could remain fixed relative to the movement of penetrating tips 132 and 133. This relative movement can influence penetration depth into tissue.

FIGS. 13A-13F show specifically how the same deployment motion and method described in FIGS. 11 and 12 is used to engage a tissue layer 130 that sits directly on top of underlying tissue 131. The deployment method and engagement with tissue is a continuous motion but for clarity is shown in discrete stages in each of FIGS. 13A-13F.

FIG. 13A demonstrates that the tip 74 of device 71 (with arms 96 and 97 in the retracted state) is pressed against tissue 130 with enough force that both tissue layer 130 and underlying tissue 131 are slightly depressed. This results in slight bulging of tissue between arms 96 and 97; however, because of the controlled width d between the tips 132, 133, only tissue layer 130 fully bulges into space 139 between penetrating tips 132 and 133. The resultant effect is that as penetrating tips 132 and 133 rotate toward each other between the illustrated stage and that depicted in FIG. 13B, the tips 132, 133 pinch only tissue 130 while displacing underlying tissue 131 away. In some instances, the rounded edges 127, 128 can assist in pushing away the underlying tissue 131 without engaging it. Continuing this motion, as penetrating tips 132 and 133 bypass each other, rotating in opposite directions, they pierce tissue 130 without puncturing underlying tissue 131.

With reference to FIGS. 13B-13E, lever 75 (see FIGS. 4-7) is transitioned from its forward position towards its rear position causing actuation rod 90 to move backward relative to the tube 73 and causing arms 96 and 97 to pivot. As the arms 96 and 97 continue to pivot, their tips 132 and 133 extend further underneath tissue layer 130 and gradually lift it away from underlying tissue 131. For example, the tips 132, 133 can engage an interior surface of the tissue layer 130. In other instances, the tips 132, 133 may not pierce through a full thickness of the layer 130. Rather, the tips 132, 133 may embed within or otherwise engage the tissue layer 130 without passing through it. In either case, as the arms 96, 97 rotate in opposite directions, the arms 96, 97 apply tension to the tissue layer 130 in opposite directions.

FIG. 13F depicts the arms 96 and 97 in their fully deployed state, and the tips 132 and 133 are underneath the tissue layer 130. The entire device 71 can be maneuvered or pulled back to further manipulate tissue layer 130 from underlying layer 131, and increase the space 134 between the two layers 130, 131. In certain applications, the space 134 is the pericardial space of a patient's heart.

Figure 14E:
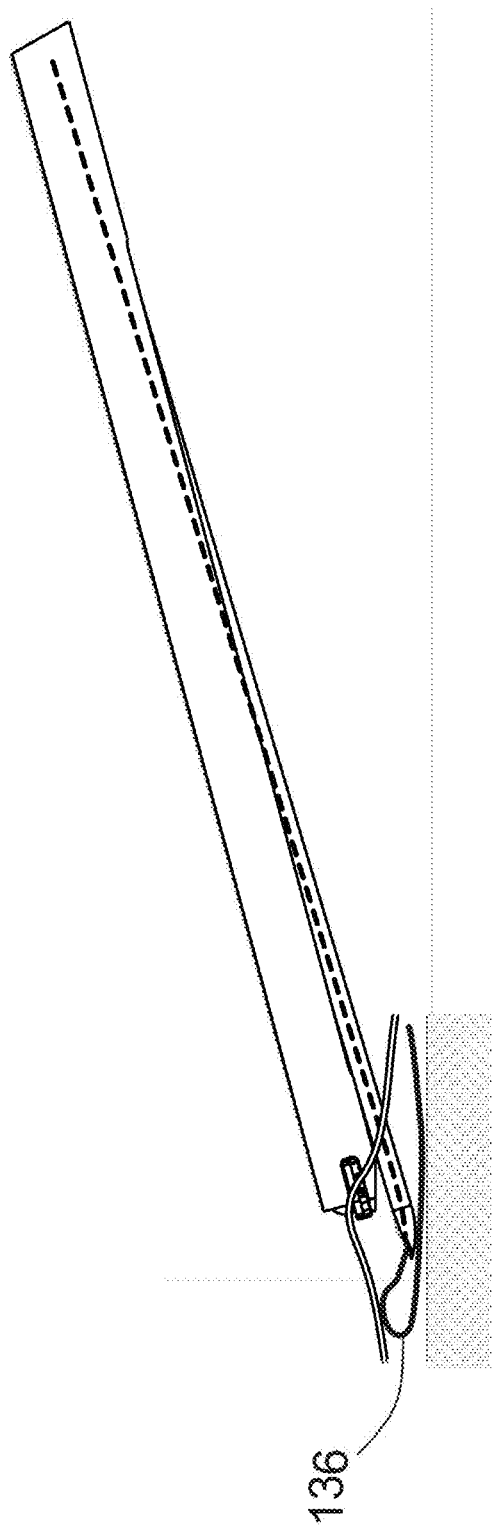
FIG. 14E depicts a side view of an introduction of a guide wire into the pericardial space, and the guide wire can be used to introduce other devices into the pericardial space.

FIGS. 14A-14E depict stages of a method in which the arms 96 and 97 are used in conjunction with the puncture needle 79 (introduced and shown in FIG. 6) when engaging tissue layer at a shallow contact angle relative to tissue layer 130. One or more of the stages of this method can be combined with the method for engaging a tissue layer depicted in FIGS. 13A-13F. With reference to FIG. 14A, the device 71 is pressed against and depresses tissue layer 130 and underlying tissue 131. This is a similar method stage to that shown in FIG. 13A. As shown, for example, in FIGS. 9 and 10, the distal face 121 of the tip 104 of actuation rod 90 is relatively blunt making it very safe to press hard against tissue without risk of puncturing through the tissue. For example, the tip 104 is sufficiently blunt to be pressed against the tissue layers 130 or 131 without penetrating them. This is also true where the tip 104 contacts these layers at contact angles greater than the contact angle depicted in FIG. 14A. In the illustrated embodiment, the puncture needle 79 is loaded into device 71 and is positioned so that the tip 135 passes through actuation rod 90 and emerges from tube 73 through opening 78 (seen in FIGS. 5 and 6).

FIG. 14B shows how the engagement arms 96 and 97 have been deployed to engage tissue layer 130 and lift it away from underlying tissue 131. This stage is similar to that depicted in FIG. 13E.

With reference to FIG. 14C, the puncture needle 79 can be advanced forward (distally) until the tip 135 punctures through tissue layer 130. Prior to advancing the tip 135 in this manner, the tissue layer 130 may be further lifted from the underlying layer 131 be pulling back on the device 71 to expand the space 134. Such expansion of the space 134 is also depicted in FIG. 14C, as can be appreciated by comparing this figure with FIG. 14B.

With reference to FIG. 14D, the puncture needle 79 continues to be advanced forward until the entire tip 135 is inside the space 134 between tissue layer 130 and underlying tissue 131. FIG. 14E shows how a standard guidewire 136 (in some embodiments, the guidewire can have a diameter of from about 0.014 inches to 0.035 inches) can be passed down a lumen of the puncture needle 79 and into the potential space 134 created by (e.g., defined between) the tissue layer 130 and underlying tissue 131.

In many applications, the portion of the device 71 shown in FIGS. 14A-14E will be in tissue and not directly seen by a user. At any suitable point during the method (e.g., at or between any steps shown in FIGS. 14A-14D) it is possible to inject contrast media, or other agents or materials, so that the area outside the tip 135 of needle 79 can be seen with fluoroscopy or any other suitable imaging technique to aid visualization.

FIGS. 15A-15D show how the device 71 and certain features thereof can be used to overcome, for example, the challenge in gaining access through the pericardium due to fat and loose connective tissue. In these figures, the fat and loose connective tissue is identified with reference numeral 140 on the surface of the pericardium, which would be equivalent to tissue layer 130. Tissue 140 has different mechanical properties than tissue layer 130 and underlying tissue 131 and can be more easily pushed apart with a blunt dissection method.

Figure 15A:
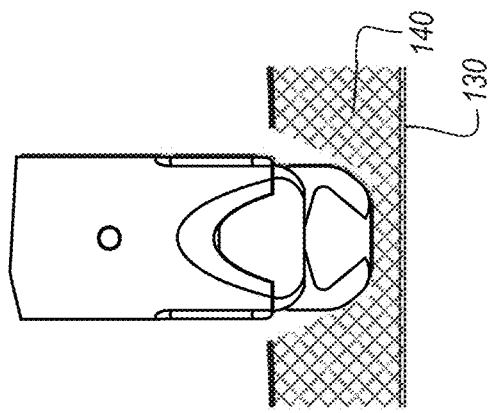
FIGS. 15A-15D depict side views of the tip of the tissue engagement device at various stages of a method in which the device is used to tunnel through adipose tissue on the surface of the fibrous pericardium.
Figure 15B:
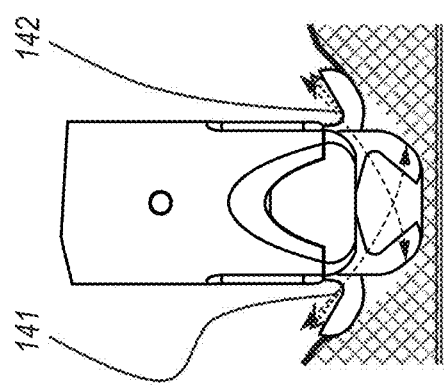

With reference to FIG. 15A, a method can include pushing the tip 74 of device 71 against the surface tissue 140. As shown in FIG. 15B, the lever 75 (see FIGS. 4-7) is actuated to cause arms 96 and 97 to deploy. The arms are shown fully deployed in FIG. 15B.

Figure 15C:
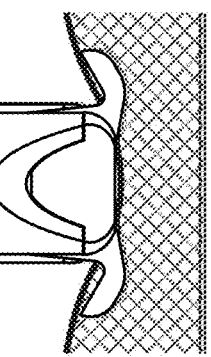

With reference to FIG. 15C, while forward pressure is applied to the device 71, the lever 75 is cycled forward and backward, causing arms 96 and 97 to cyclically deploy and retract, which is shown by the bidirectional arrows 141 and 142. This can be repeated, and typically no more than 2 or 3 times (cycles) should be needed to fully penetrate through the tissue layer 140. Any suitable number of actuation cycles is possible to achieve the desired penetration.

Figure 15D:
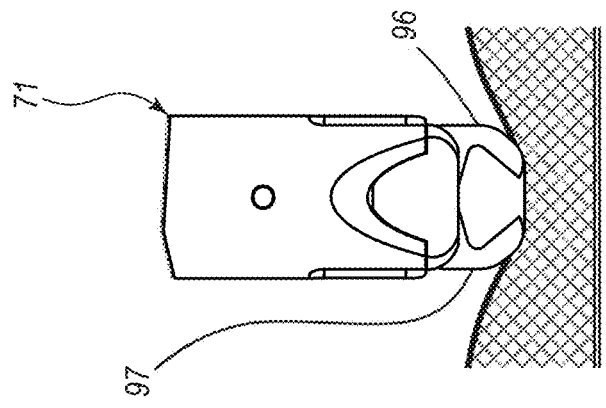

FIG. 15D depicts how the cycling method just described can allow the tip 74 to tunnel or dissect through the tissue layer 140 and bring it much closer to the target tissue layer 130. Additional cycling, while advancing the device forward, may be employed to bring the tip 74 into contact with the tissue layer 130 (but this additional tunneling to the layer 130 is not explicitly shown here).

FIG. 16A shows a top plan view of an embodiment of arms 96 and 97 that may be used in the device 71. In the illustrated embodiment, the arms 96 and 97 are identical and flat, which can help to reduce the overall cost of the device 71. As they are flat, the arms 96 and 97 can be made from stock sheet material using, for example, laser cutting, water jet cutting, photo etching, or stamping processes, and the like, which are low cost. Any suitable material is contemplated for the arms 96, 97, including metal, biocompatible plastic, etc. The arms 96, 97 can be substantially rigid, in some embodiments. The arms 96 and 97 have holes 150 and 151 and grooves 117 and 118, respectively. The centerlines 152 and 153 pass through holes 150 and 151, and the center of grooves 117 and 118, respectively. The orientation of the tips 132 and 133 is defined by axis 154 and 155. The tips 132 and 133 have straight inside edges 172 and 173, which may also be referred to as shelves. As shown in FIG. 13F, the tissue layer 130 may rest on the shelves 172, 173 when the arms 96, 97 are deployed. Stated otherwise, the shelves 172, 173 may extend laterally to engage a lower surface of the tissue layer 130. The shelves 172, 173 may aid in pulling the tissue layer 130 away from the tissue layer 131.

Figure 16B:
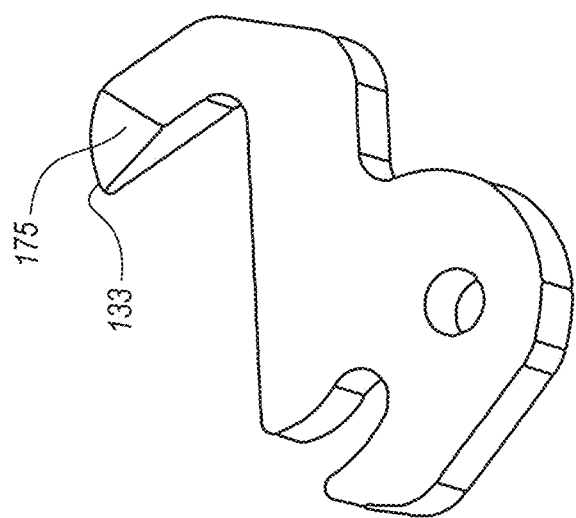
FIG. 16B is a perspective view of the engagement arm that illustrates a bevel to increase tip sharpness.

With reference to FIG. 16B, in some instances, it may be desirable to increase the sharpness near tips 132 and 133. This may be accomplished, for example, by adding one or move bevel planes 175 that are at angles relative to the main planar orientation of the arms 96, 97. Any other suitable sharpened configuration is also contemplated.

Figure 17:
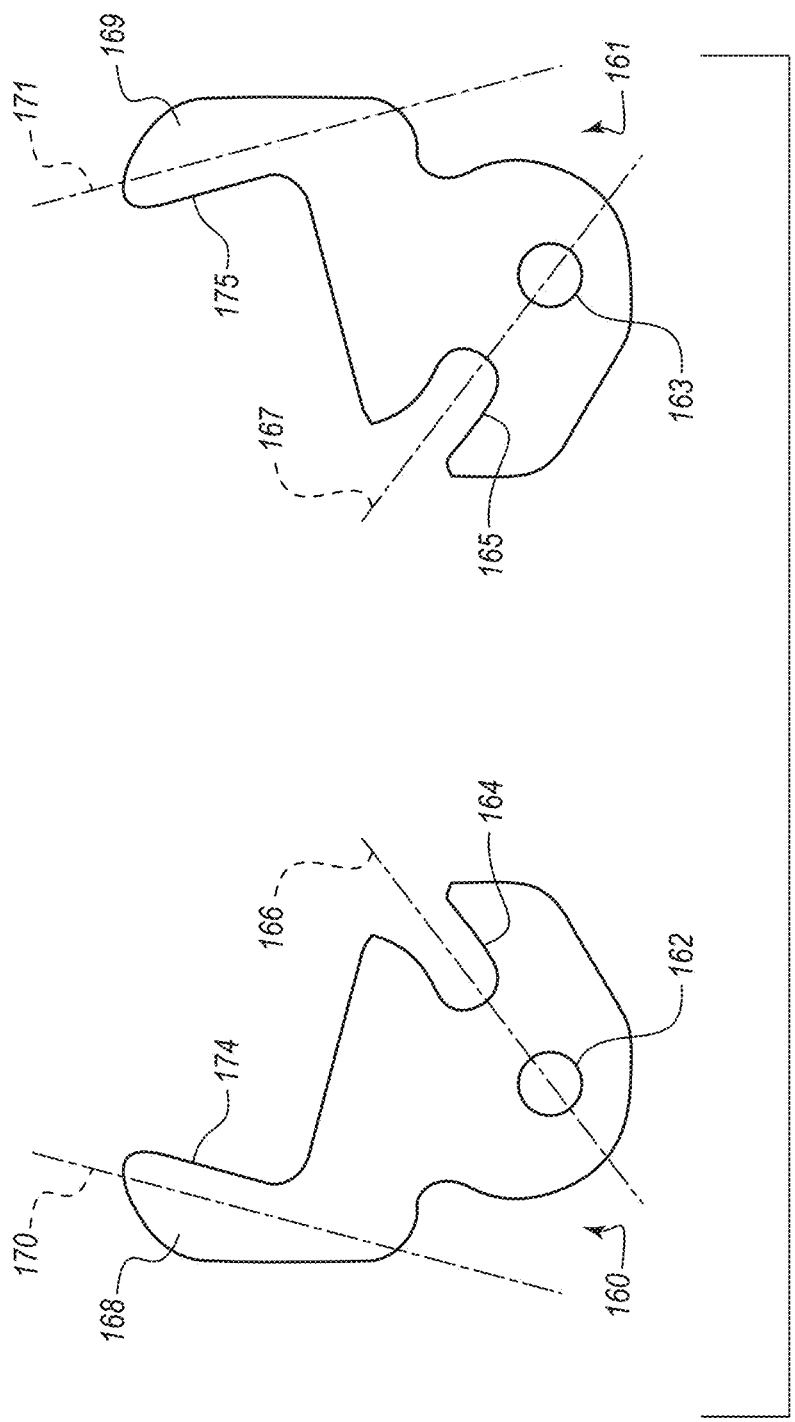
FIG. 17 shows a detailed view of another embodiment of an engagement arm with a rounded tip to reduce tissue injury.

Many different embodiments of the arms are contemplated. FIG. 17 depicts another embodiment of arms 160 and 161 with different tip angles than those of the arms 96 and 97. The arms 160 and 161 have holes 162 and 163, and grooves 164 and 165. Centerlines 166 and 167 pass through the centers of grooves 164 and 165, and holes 162 and 163. The arms 160 and 161 differ from the arms 96 and 97 in that the orientation of tips 168 and 169 defined by axes 170 and 171 are at a greater angle relative to centerline 166 and 167 than axis 154 and 155 are to centerlines 152 and 153 in FIG. 16A. The tips 168 and 169 have straight inside edges 174 and 175. In some arrangements, the larger angle of the arms 160, 161 can result in a larger gap between the tips of the arms 160, 161 in an assembled device that is in the retracted state, as compared, for example, to the gap 139 in FIG. 11.

Figure 18:
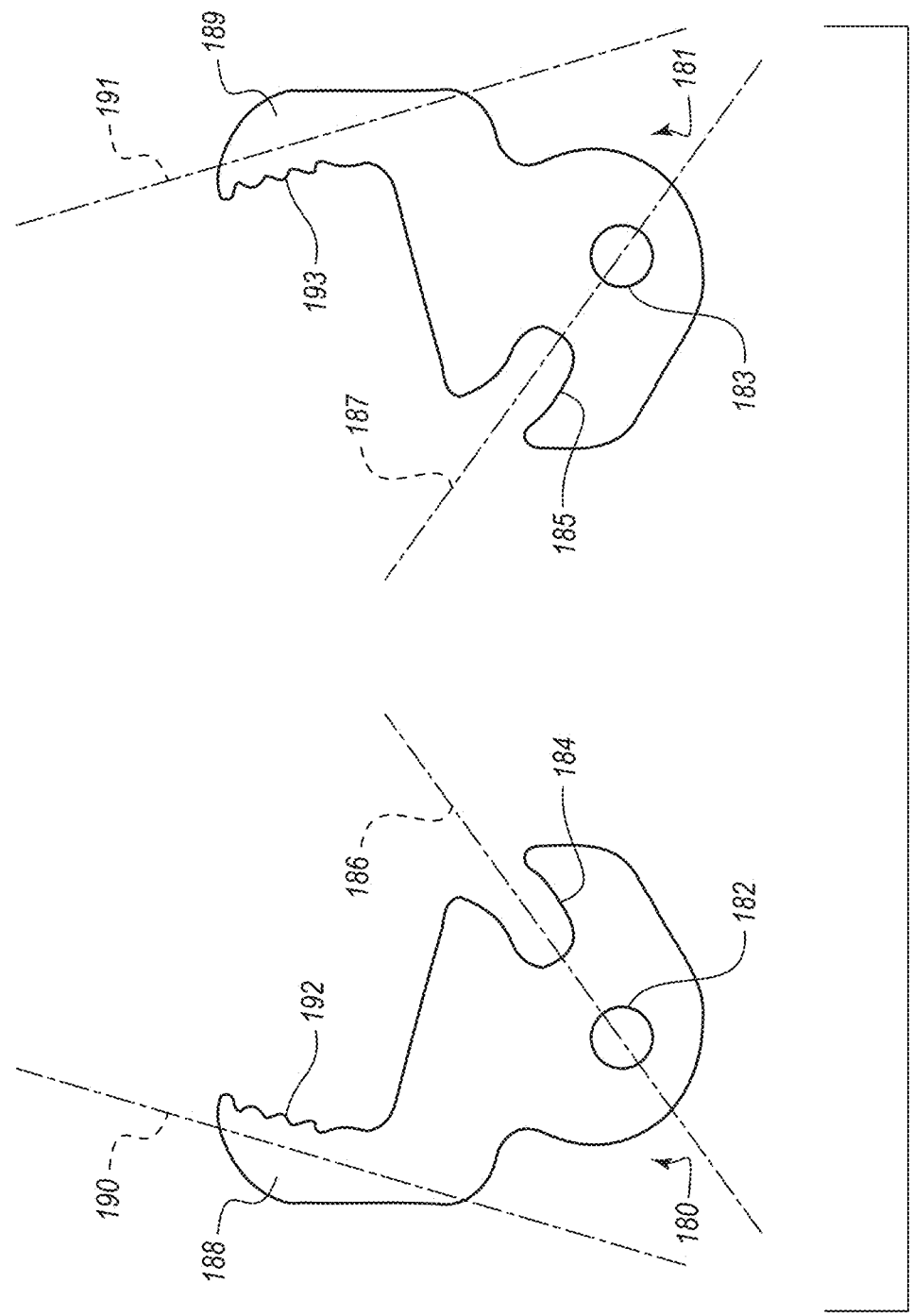
FIG. 18 shows a detailed view of yet another embodiment of an engagement arm with teeth to enhance securement of a tissue layer.

FIG. 18 depicts another embodiment of arms 180 and 181 with different tip angles and tip inside edges than the arms 96 and 97. The arms 180 and 181 have holes 182 and 183, and grooves 184 and 185. Centerlines 186 and 187 pass through the centers of grooves 184 and 185, and holes 182 and 183. The arms 180 and 181 differ from the arms 96 and 97 in that the orientation of tips 188 and 189 defined by axis 190 and 191 are at a greater angle relative to centerline 186 and 187 than axis 154 and 155 are to centerlines 152 and 153 from FIG. 16A. In the illustrated embodiment, the angles are the same as those for the arms 160, 161 of FIG. 17. The tips 188 and 189 of the arms 180, 181 include serrated inside edges 192 and 193, which can assist in engaging the tissue layer 130.

Figure 19:
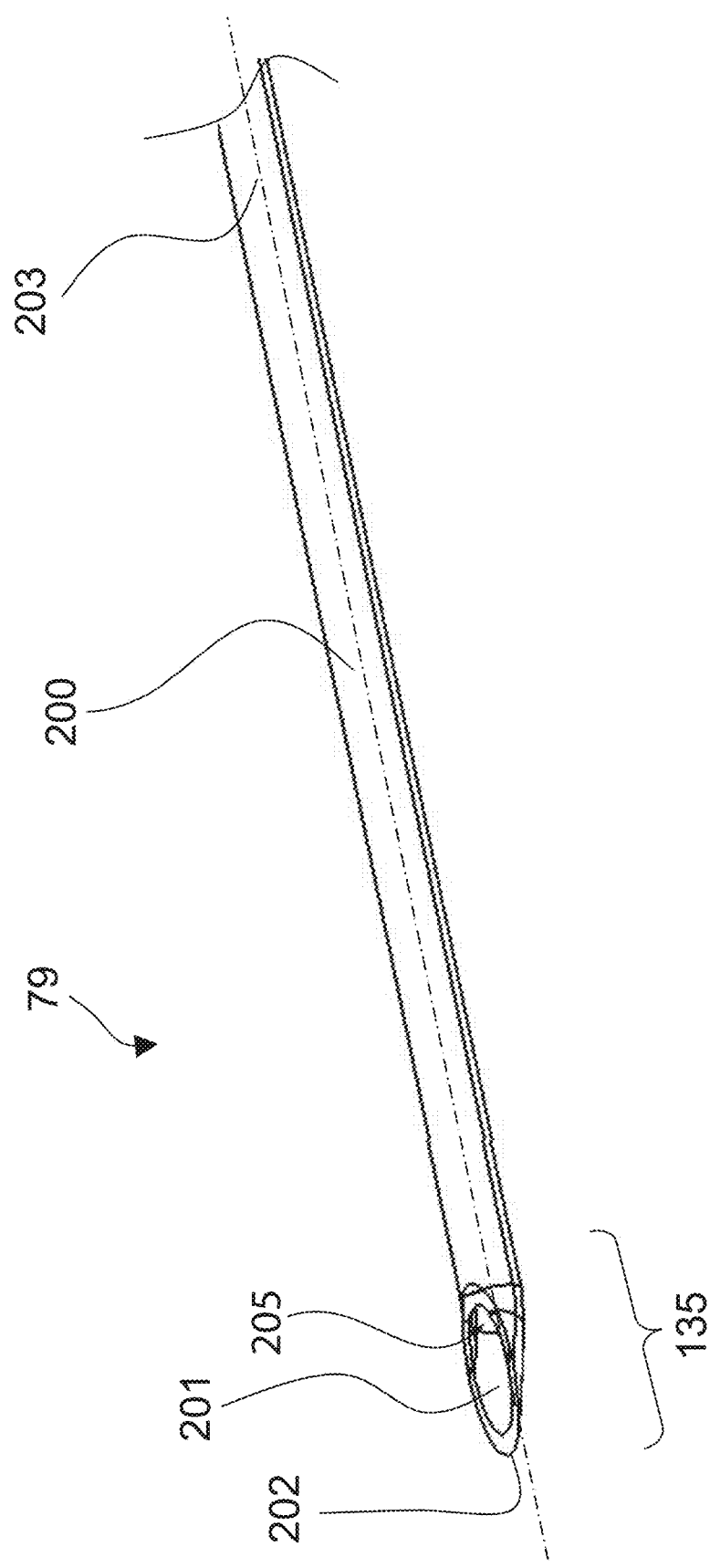
FIG. 19 is a detailed view of the tip of a tissue puncturing needle intended to pass through the tissue layer after securement of the tissue layer with the engagement arms of the tissue engagement device.

FIG. 19 shows a perspective view of a distal end of the puncture needle 79. The needle 79 includes a tube 200 with axis 203. The tube 200 is preferably round but can be any shape. Tip 135 has an opening 201 and distal edge 202. The opening 201 faces away from the main axis 203 and prevents coring of tissue that can enter the distal opening 201 as the needle 79 is pushed along its axis 203 through tissue. Stated otherwise, the needle 79 can be a non-coring needle. Other embodiments can be generally any shape (e.g., any suitable cross-sectional configuration) and can provide any suitable orientation for opening 201. The tube 200 can define a lumen 205 that is used as a delivery pathway for accessory delivery, such as a guidewire and/or contrast media during the access approach, as previously discussed.

Figure 20:
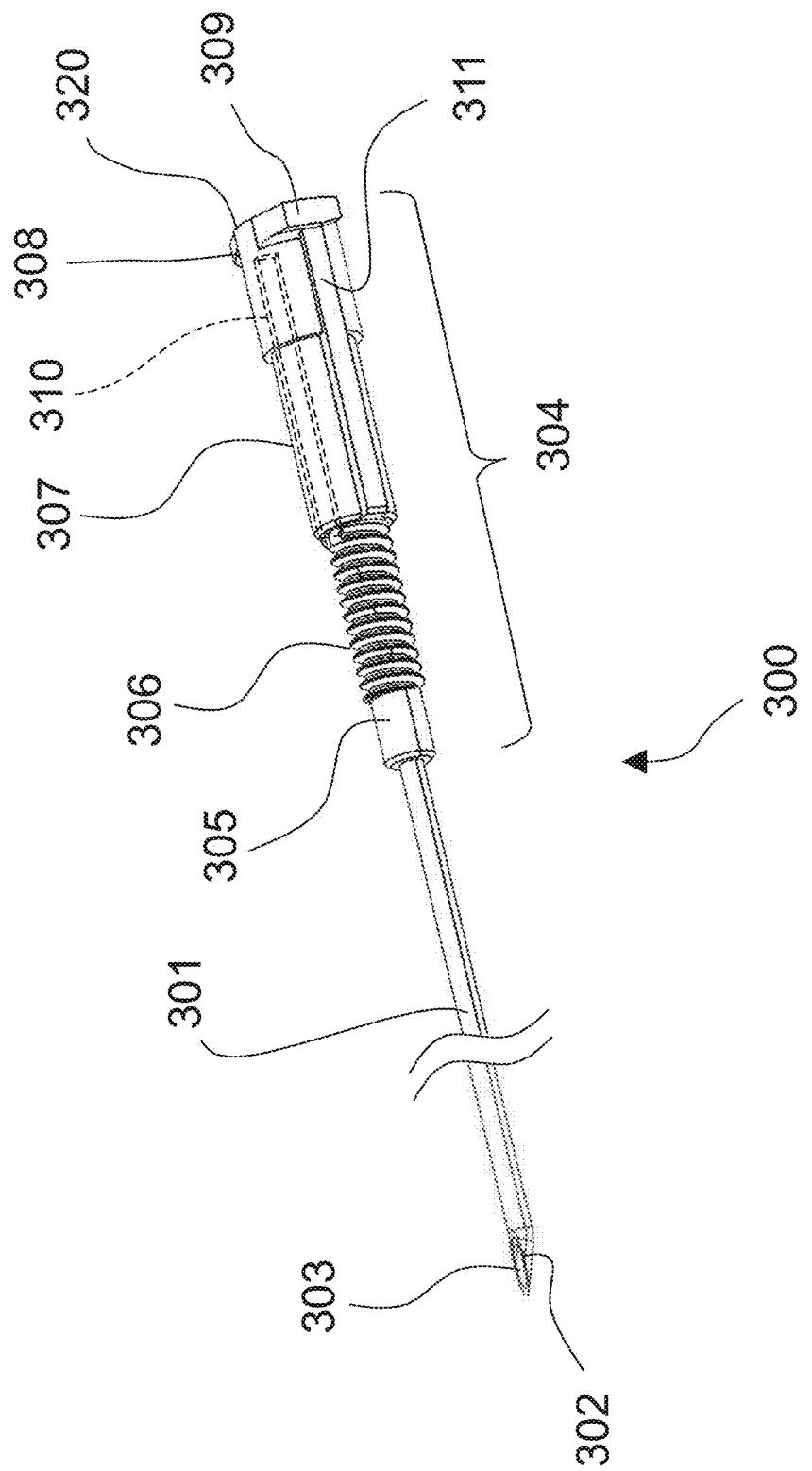
FIG. 20 is a perspective view of a proximal hub for a tissue puncturing needle showing a thread feature for controlled needle advancement; the illustrated hub also has a luer fitting for attachment to a syringe.
Figure 21:
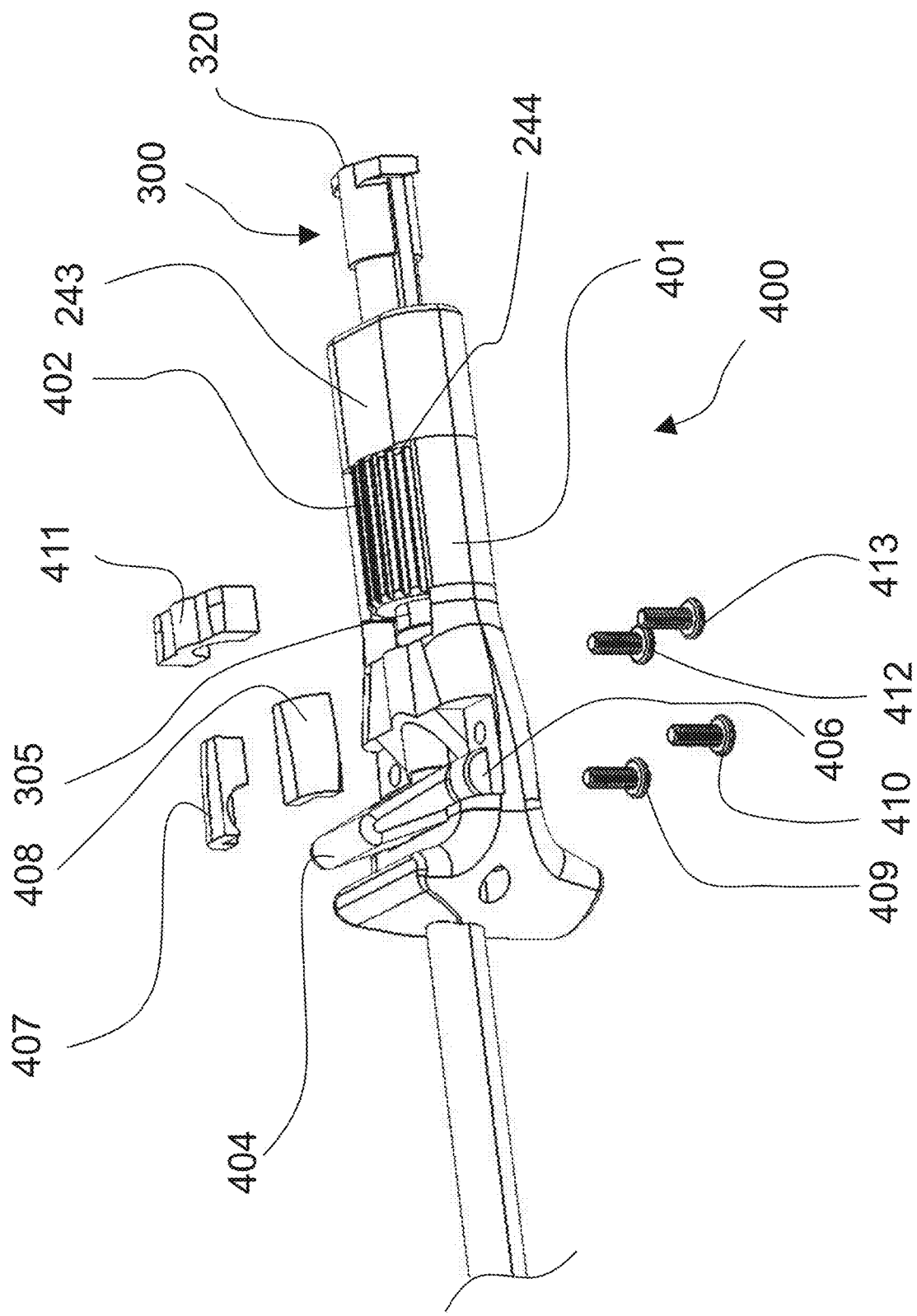
FIG. 21 is an exploded perspective view of an embodiment of a device handle that incorporates a dial that engages the thread feature depicted in FIG. 20.

FIGS. 20 and 21 depict another embodiment of a needle 300 and an embodiment of a mating handle 400, which enables improved motion control of the needle 300 (relative to motion control of the needle 79), and improved means to deliver contrast media and guidewire accessories. The needle 300 includes a tube 301 and a tip 302 with opening 303. A fitting 304 is attached to the proximal end of needle 300. The fitting 304 includes a distal hub 305, a thread 306, and a proximal hub 307. A Luer type connection 320 is integrated into the proximal end of the fitting 304 with ears 308 and 309, and guides 310 and 311. The needle 300 interfaces with the handle 400.

As shown in FIG. 21, the handle 400 includes a body 401 and a knob 402 that is threaded onto the needle thread 306. The handle 400 also has lever 404 with hubs 406 (such as the hubs 84, 85 in FIG. 8). Covers 407 and 408 are fastened using screws 409 and 410 to the handle body 401, and are positioned over the lever hubs 406 so that lever 404 can pivot. Cover 411 is fastened to handle body 401 using screws 412 and 413, and is positioned over the needle fitting distal hub 305 so that fitting 304 is guided through handle body 401. The handle body 401 has matching internal grooves (not visible) for guides 310 and 311, which keep fitting 304 from rotating as knob 402 is rotated.

In use, the knob 402 can be rotated in either direction, which advances or retracts needle 300 without letting the needle 300 rotate. Stated otherwise, rotation of the knob 402 can result in distal or proximal translation of the needle 300. The Luer connection 320 is the common standard type used to interconnect fluid fittings and syringes together. Any other suitable connection interface is contemplated.

The Luer connection 320 can enable additional other functions. One example is that a syringe with contrast media can be connected to the Luer fitting 320, so that as the device 71 is being advanced towards the heart, contrast can be injected to verify the position continuously during the approach. A second example is that once the puncture needle 300 has been placed into the pericardial space, a means for delivering a guide wire into the pericardial space is established. Once a guidewire is delivered, the device 71 can be removed leaving the guidewire in place, which then provides the means to deliver other medical devices such as sheaths and in turn then mapping and ablation catheters.

Figure 22A:
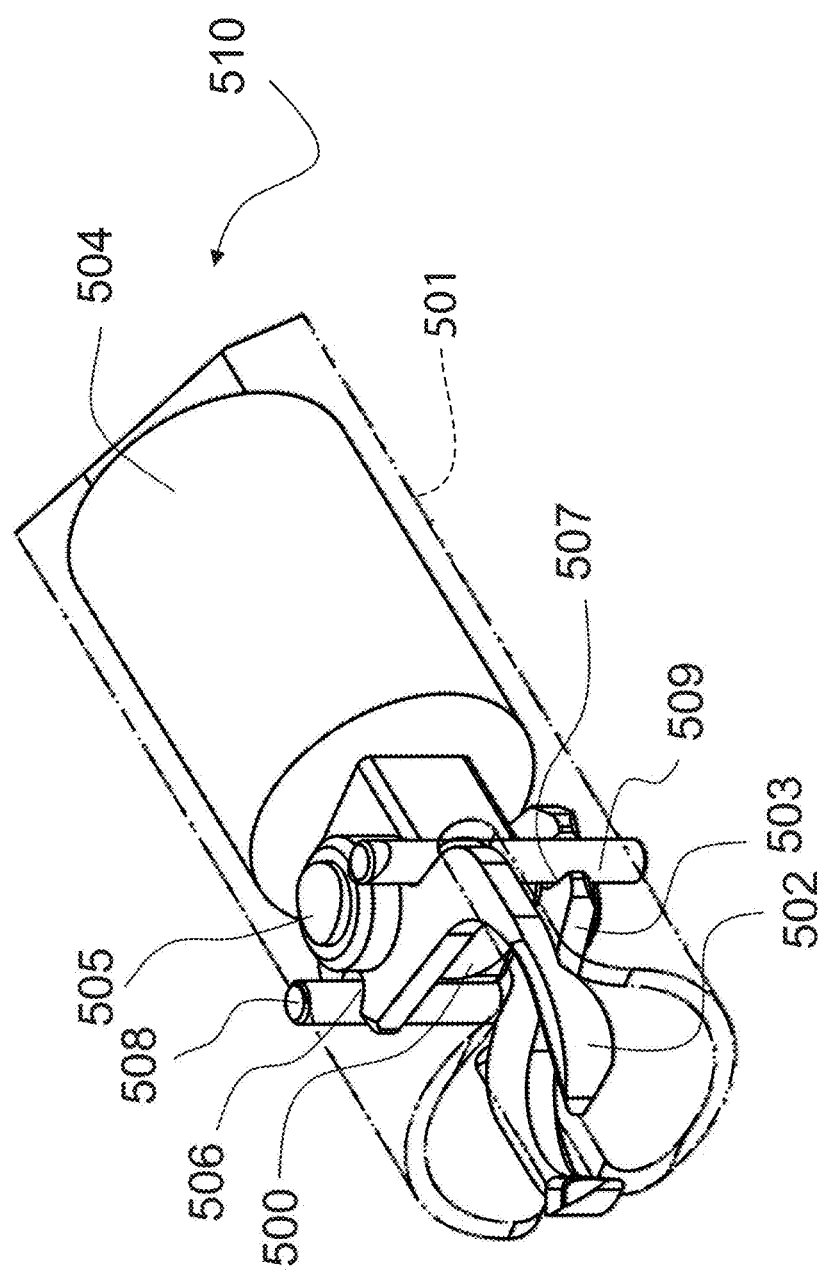
FIG. 22A is a detailed perspective view of a tip of another embodiment of a tissue engagement device in which a needle pathway is between the engagement arms, which are depicted in a retracted state.
Figure 22B:
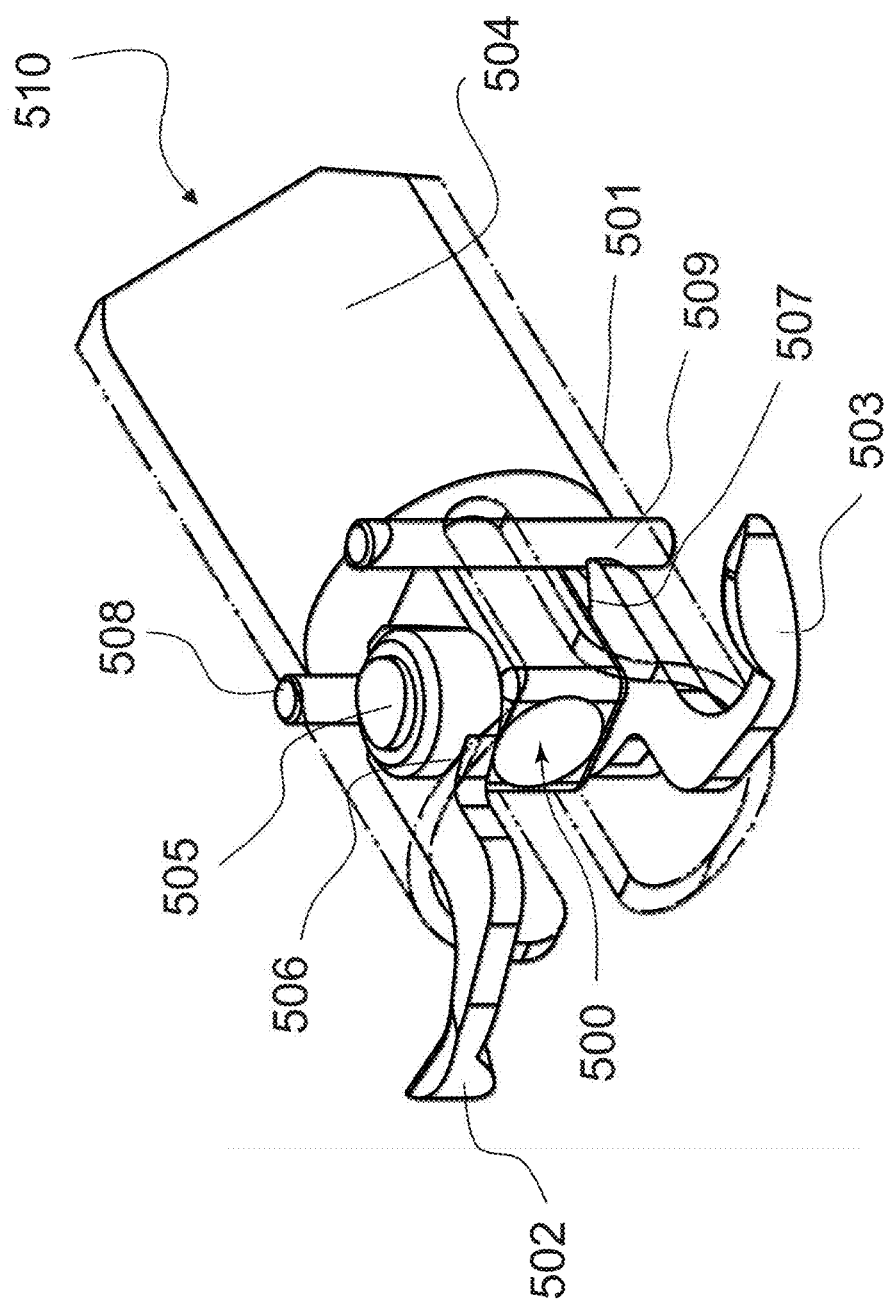
FIG. 22B is a detailed perspective view of the tip of FIG. 22A that depicts the engagement arms in a deployed state.

FIGS. 22A and 22B depict another embodiment of a tissue engagement device 510. The device 510 is shown in an undeployed state in FIG. 22A and is shown in a deployed state in FIG. 22B. The device 510 defines a needle pathway 500 that is either parallel to or collinear with a central axis of an outer or main tube 501. The needle pathway is between (e.g., extends between) tissue engagement arms 502 and 503. In this embodiment the needle pathway 500 is integral to (or defined by) the actuation rod 504. The device 510 includes a pin 505 that is attached to the actuation rod 504. The arms 502, 503 are pivotally coupled to the pin 505 at opposite sides of the needle pathway 500. In this respect, the arms 502, 503 are spaced further apart than they are in the device 71 described above. Engagement arms 502 and 503 have grooves 506 and 507 respectively. Pins 508 and 509 are fixed in a position through main tube 501. Stated otherwise, the pins 508 and 509 are attached to the main tube 501. As actuation rod 504 is pushed forward (e.g. distally) it moves engagement arms 502 and 503 with it, which in turn pivot about pin 505 as their grooves 506 and 507 engage pins 508 and 509 and cause the pivoting motion. Referring to previous figures, this is different than the device 71, where two pivot points were used and a single post effected camming of the arms. Here, a single pivot axis is used (i.e., the axis passing through the post 505), and two separate pins 508 are used to individually effect rotation of each arm 502, 503. Another difference is the actuation rod 504 moves forward (distally) rather than backwards (proximally) to deploy the engagement arms 502, 503 in the present embodiment. The needle path 500 is also parallel to the sidewall of the shaft or tube 501 and is fully encompassed thereby, whereas the needle path 91 of the device 71 is angled relative to its tube 73 and passes through the sidewall thereof, as seen in FIG. 6.

Figure 23A:
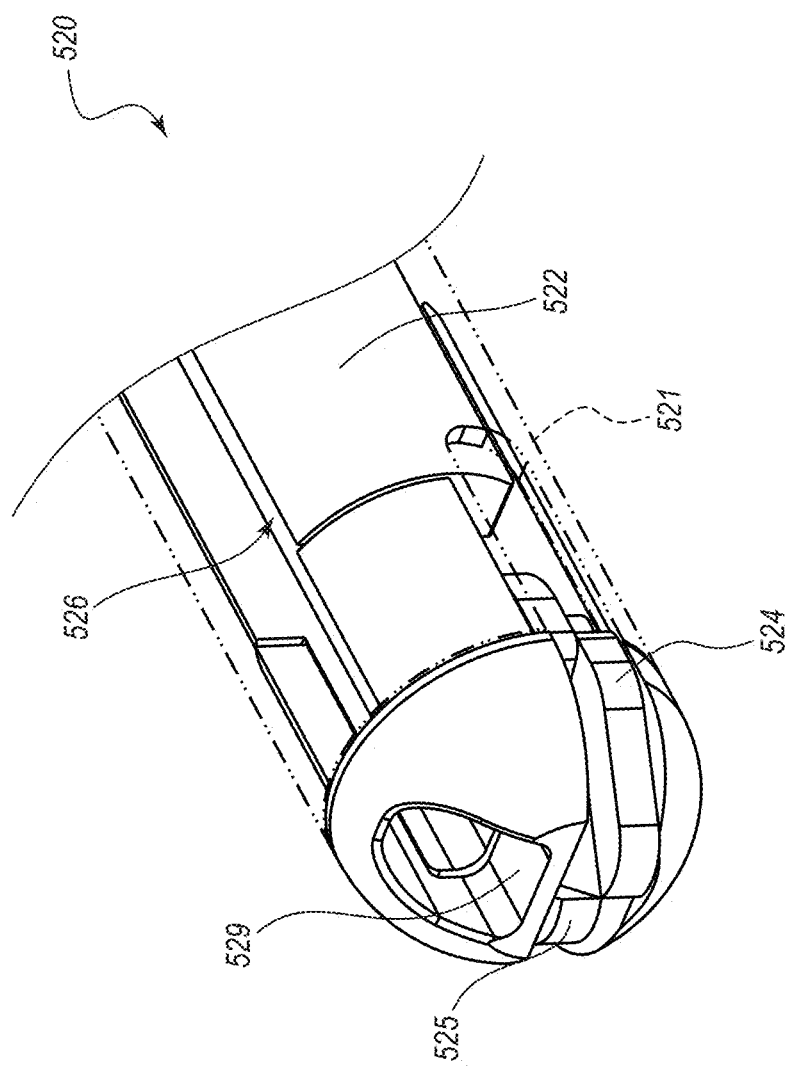
FIG. 23A is a detailed perspective view of the tip of yet another embodiment of a tissue engagement device in which a needle pathway is on the top of the engagement arms, which are depicted in a retracted state.
Figure 23B:
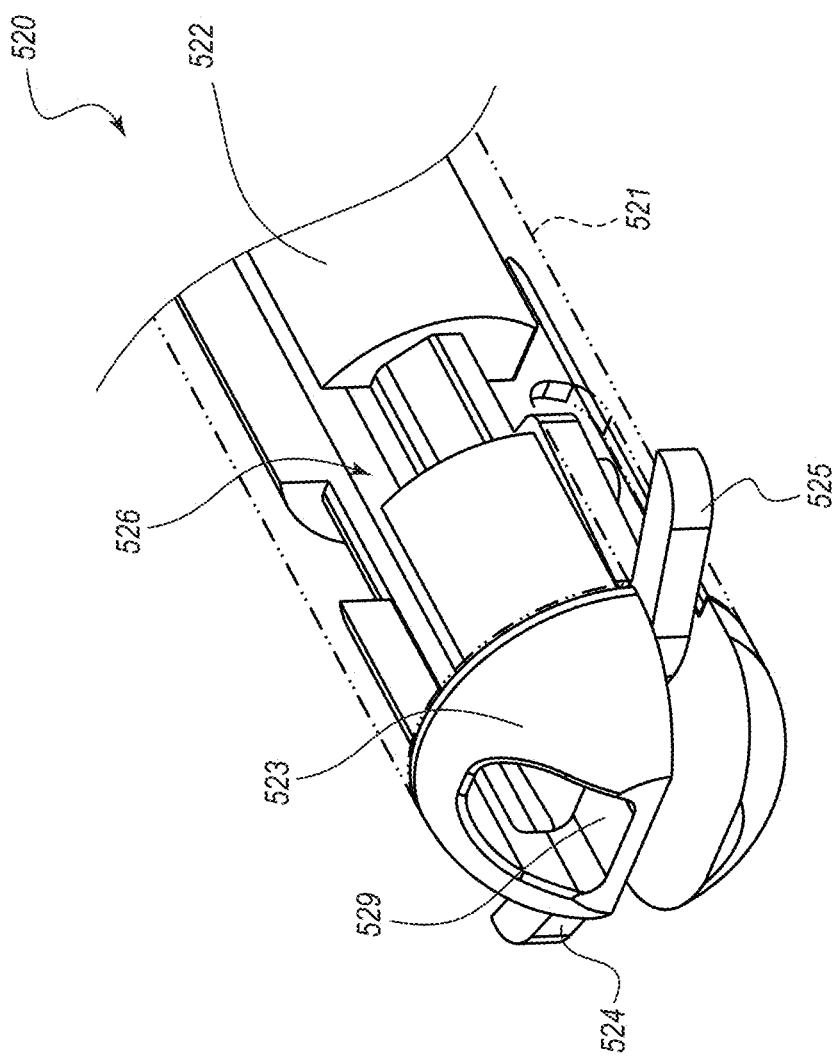
FIG. 23B is a detailed perspective view of the tip of FIG. 23A that depicts the engagement arms in a deployed state.

FIGS. 23A and 23B show another embodiment of a tissue engagement device 520 that defines a straight needle path 526 that is parallel to the main tube 521. Unlike with the device 510, however, the needle path 526 does not pass between the engagement arms 524, 525. Rather, the needle path 526 is above the engagement arms 524 and 525 in the depicted orientation, or stated otherwise, the needle path 526 is laterally offset from the engagement arms 524, 525. The device 520 includes an actuation rod 522 to which engagement arms 524 and 525 are connected by pins (not shown). In a similar way as disclosed herein, actuation rod 522 is used to deploy and retract engagement arms 524 and 525. The device 520 includes a stationary tip 523 that defines a needle opening 529. The tip 523 guards both the top and bottom sides of the engagement arms 524 and 525, in the illustrated orientation. Stationary tip 523 is fixedly attached to the distal end of main tube 521.

Figure 24A:
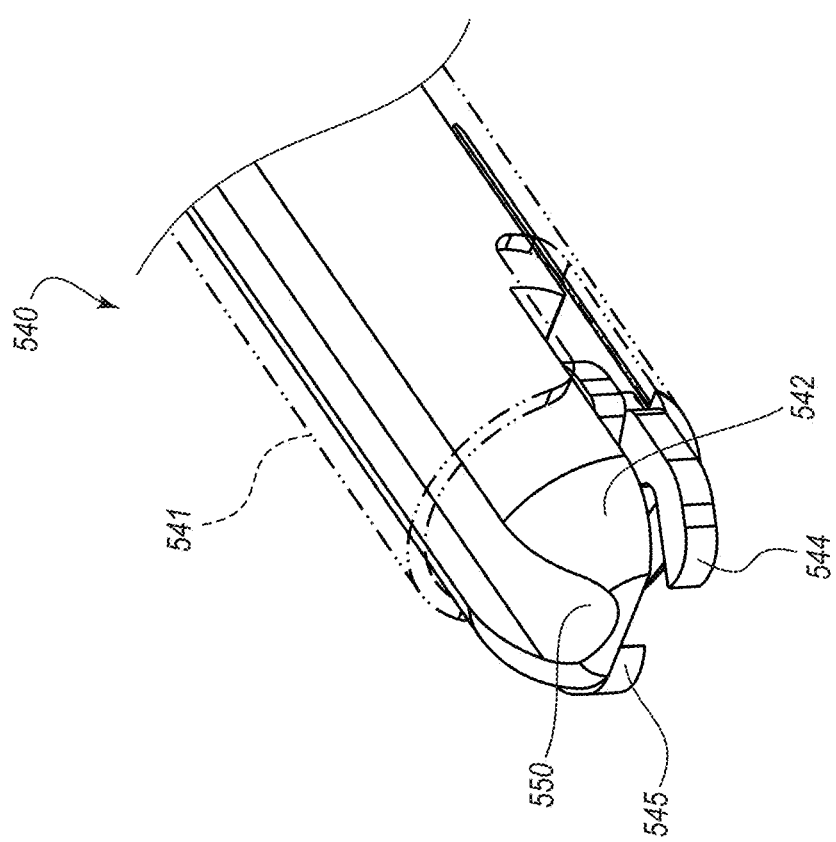
FIG. 24A is a detailed perspective view of the tip of a further embodiment of a tissue engagement device having engagement arms that are depicted in a retracted state.
Figure 24B:
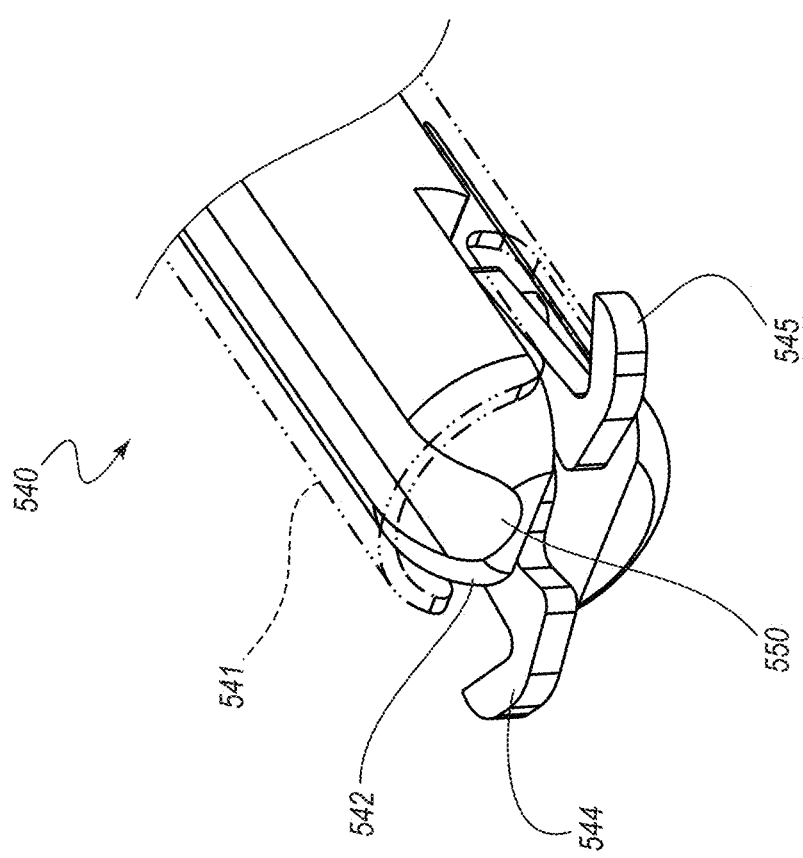
FIG. 24B is a detailed perspective view of the tip of FIG. 23A that depicts the engagement arms in a deployed state.

FIGS. 24A and 24B depict yet another embodiment of a tissue engagement device 540 in undeployed and deployed states, respectively. The device 540 defines a straight needle path 550 that is parallel to a main tube 541 and is positioned above engagement arms 544 and 545. As with prior embodiments described herein, the engagement arms 544 and 545 are deployed by axial movement of actuation rod 542. The needle path 550 is defined by the actuation rod 542 and is bordered along an upper end thereof by the tube 541.

Figure 25A:
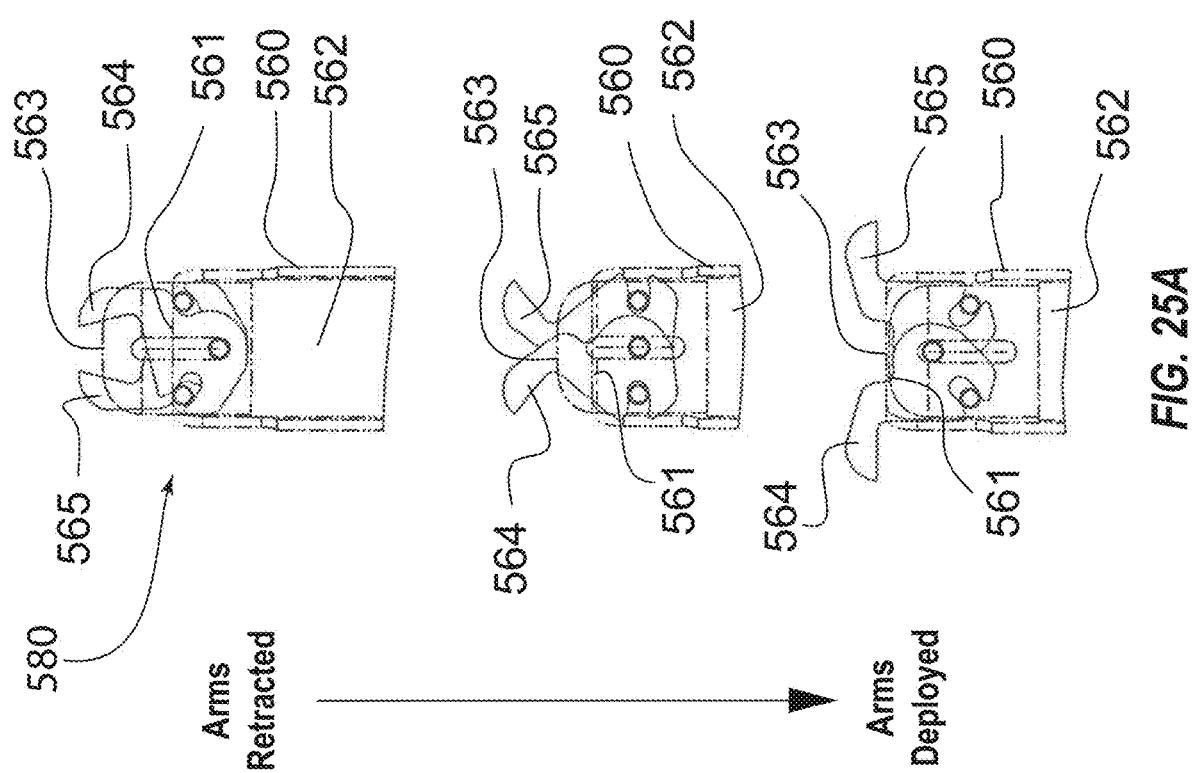
FIG. 25A depicts detailed sequential views of the tip of another embodiment of a tissue engagement device in which an actuation rod is pushed relative to a shaft to deploy the engagement arms, which are pivotally mounted to the actuation rod.
Figure 25B:
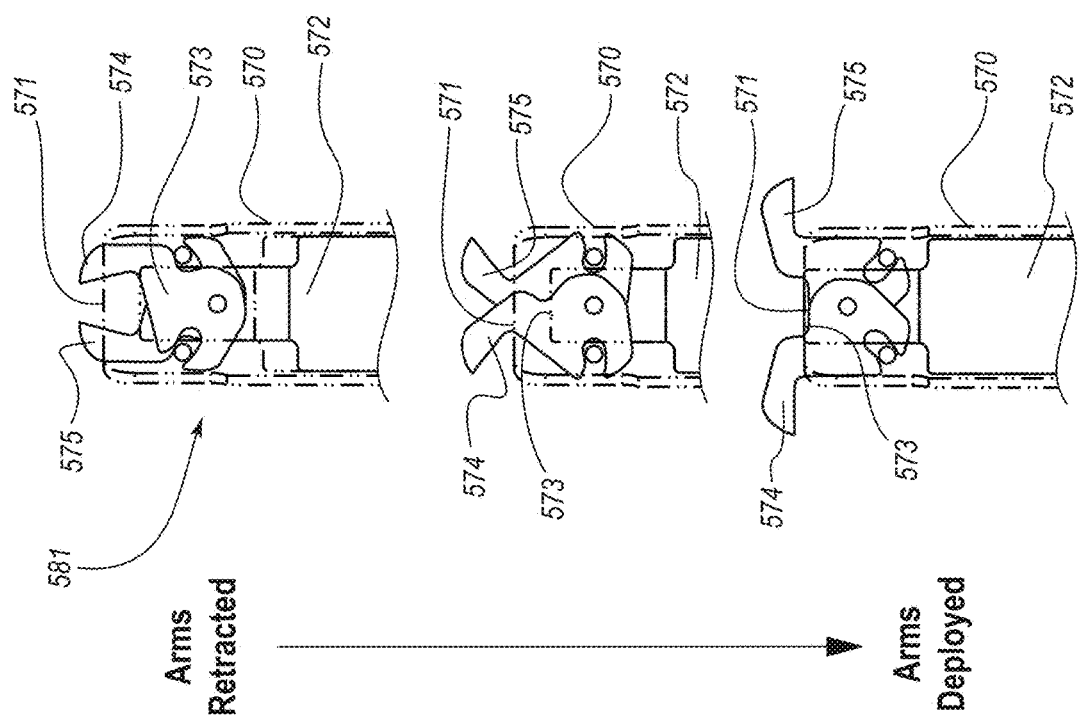
FIG. 25B depicts detailed sequential views of the tip of yet another embodiment of a tissue engagement device in which an actuation rod is pulled relative to a shaft to deploy the engagement arms, which are pivotally mounted to the actuation rod.

FIGS. 25A-25C are detailed images of distal tips of further embodiments of tissue engagement devices 580, 581, 600 that are actuated in different manners; in particular, FIGS. 25A, 25B depict the differences between a pull versus a push actuation motion where engagement arms are pivotally mounted to an actuation rod. In FIG. 25C, the engagement arms are pivotally mounted to the tube.

In FIG. 25A, the device 580 includes a tube 560, an actuation rod 562, and engagement arms 564, 565. The tube 560 has a distal edge 561 and actuation rod 562 has a distal edge 563. As actuation rod 562 is pulled and moves proximally relative to the tube 560, the engagement arms 564 and 565 move from a retracted state to a deployed state in a manner similar to those described above.

In FIG. 25B, the device 581 includes a shaft or tube 570 that has distal edge 571. An actuation rod 572 has distal edge 573. Engagement arms 574 and 575 are pivotally mounted to the actuation rod 572. As actuation rod 572 moves distally (e.g., is pushed) relative to the tube 570, the engagement arms 574 and 575 move from a retracted state to a deployed state. The means by which this actuation is achieved is not limited to the particular arrangement shown.

FIG. 25C depicts another embodiment of a tissue engagement device 600 that includes a sheath, shaft, or tube 610 and an actuation member or actuation rod 620. The device 600 further includes engagement arms 630, 631 similar to engagement arms disclosed above. The engagement arms 630, 631 define camming grooves 632, 633, respectively. The actuation mechanisms are similar between the engagement devices 581 and 600, except that the engagement arms 630, 631 are pivotally attached to the tube 610, rather than being pivotally attached to the actuation rod 620. In particular, both engagement arms 630, 631 are configured to pivot about a common axis that passes through a pivot post 640, which post is fixedly secured to the tube 610. Two camming posts 641 642 are fixedly secured to the actuation rod 620. The device 600 is transitioned from the retracted state to the deployed state by moving the actuation rod 620 proximally relative to the tube 610. Conversely, the device 600 is transitioned from the deployed state to the retracted state by moving the actuation rod 620 distally relative to the tube 610. As with the actuation rod 90 depicted in FIGS. 9 and 10, which defines a slot 101, the actuation rod 620 can define a slot 650. The slot 650 can be sized to permit passage of the pivot post 640.

Any other suitable arrangement is contemplated for actuating the engagement arms. For example, in some embodiments, one or more engagement arms can be pivotally mounted to an actuation rod, one or more additional engagement arms can be pivotally mounted to the tube, and relative movement between the actuation rod and the tube (to which one or more camming posts may be mounted) can transition the actuation arms between the retracted and deployed states.

Figure 26:
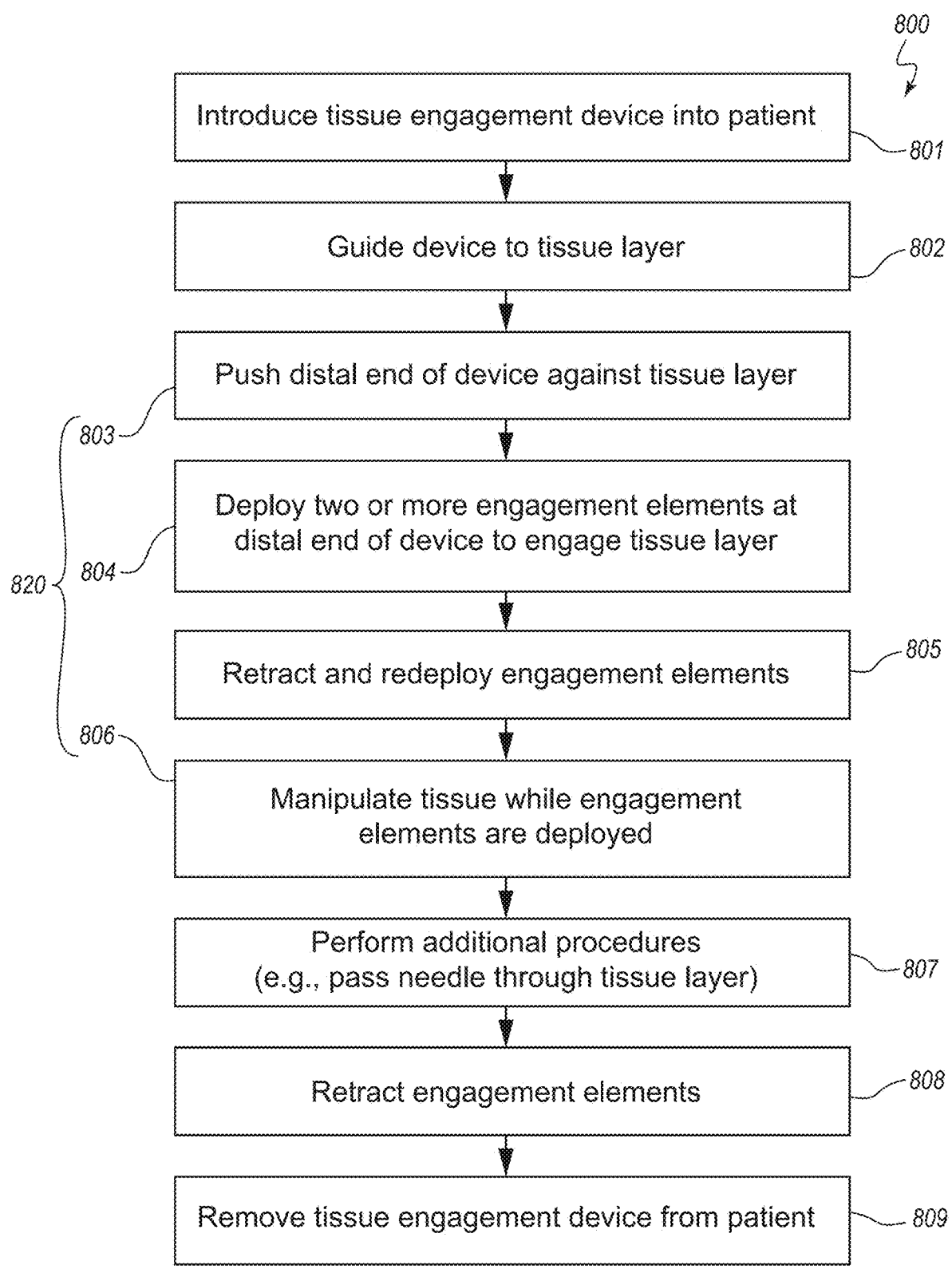
FIG. 26 depicts a method of using the engagement arms of a tissue engagement device to engage and manipulate tissue.
Figure 28A:
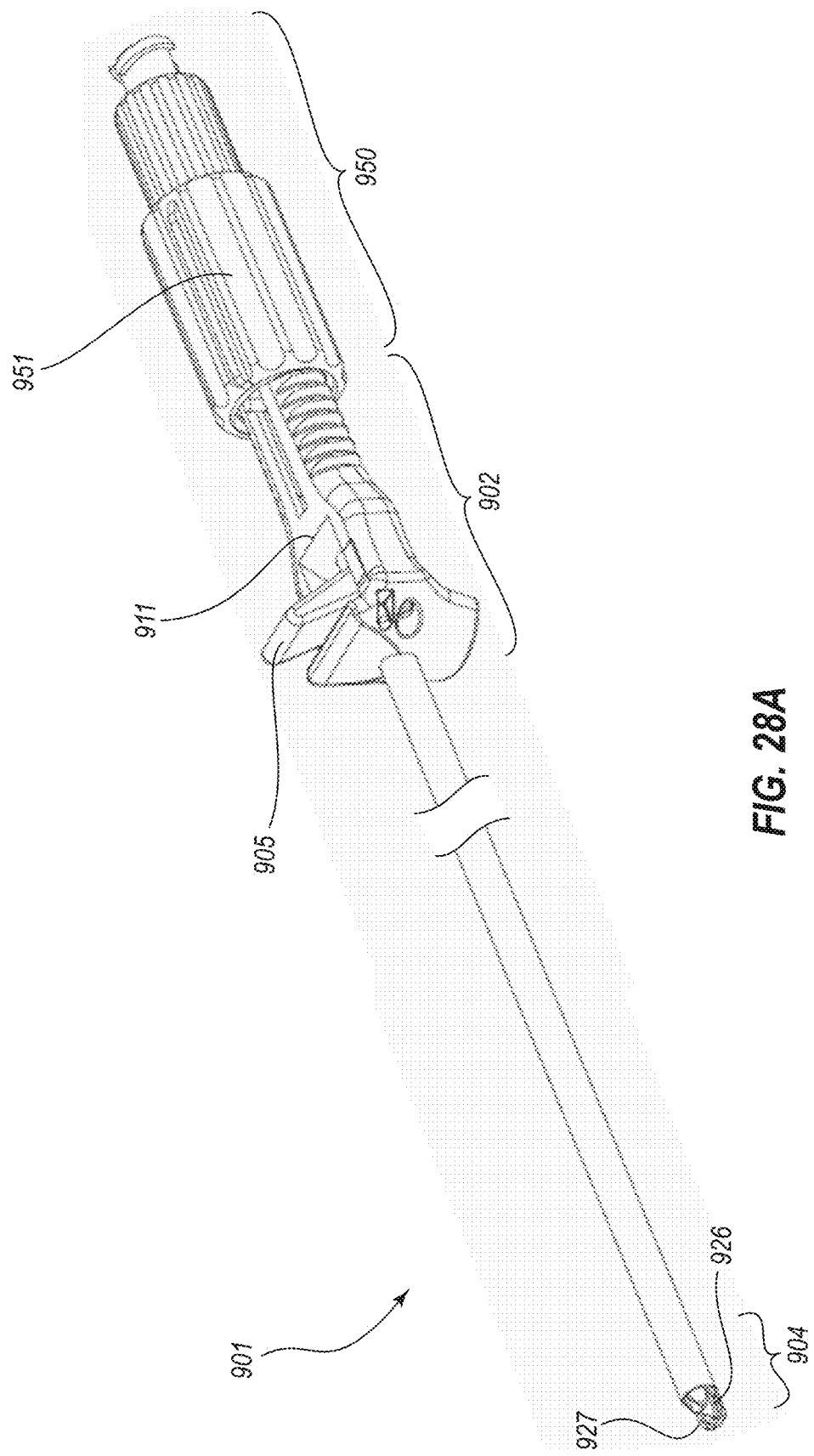
FIG. 28A is a perspective view of another embodiment of a tissue engagement device that incorporates a threaded needle advancement mechanism and a fitting for a locking luer connection.
Figure 28B:
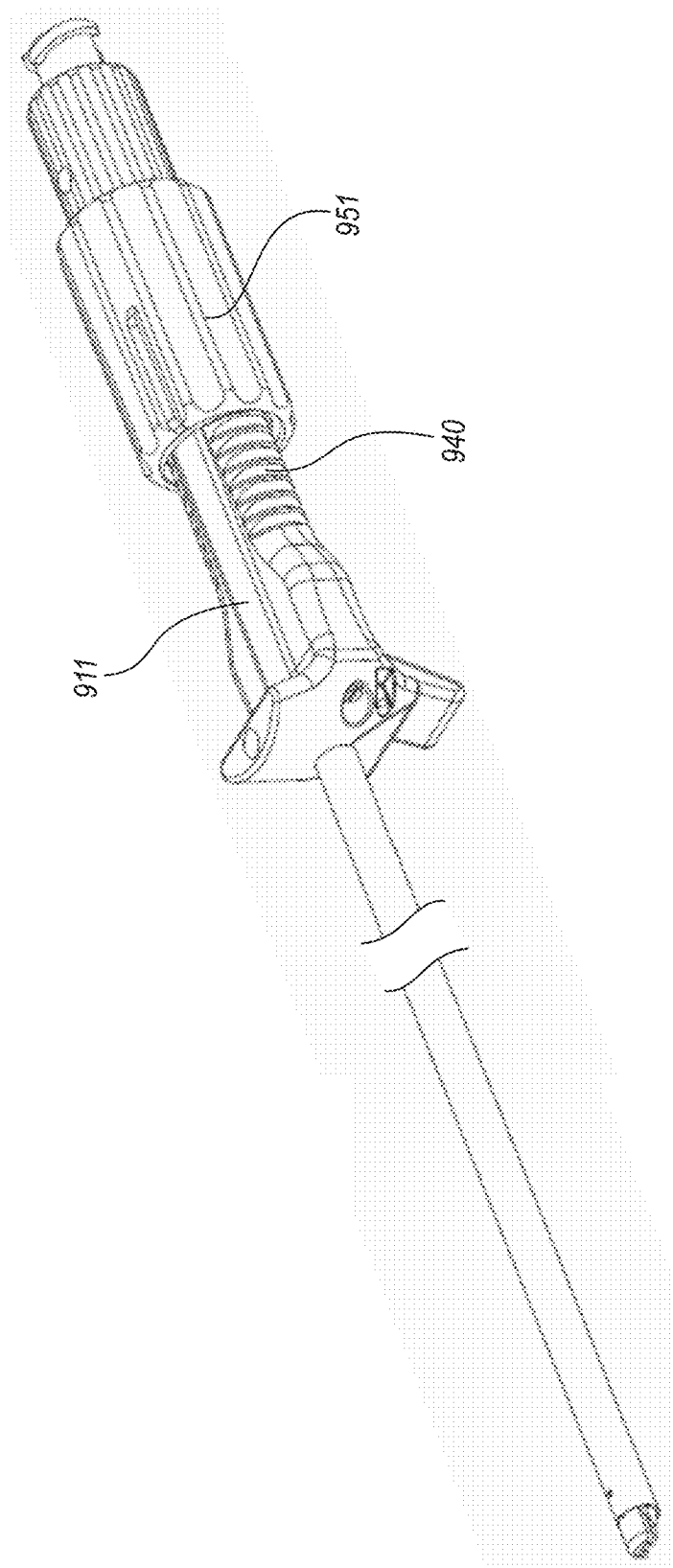
FIG. 28B is an obverse perspective view of the tissue engagement device of FIG. 28A.

FIG. 26 depicts a method 800 for engaging tissue. The method 800 has been described previously herein, and it should be understood that any suitable combination of steps of the method are contemplated. For example, the method 800 includes nine stages or steps 801, 802, 803, 804, 805, 806, 807, 808, 809. Any suitable combination of the steps is contemplated. Thus, for example, a method 820 can include the steps 803, 804, and 806, while other steps (such as the step 805) are omitted. The method 820 may be considered a core method that may be common to numerous methods that employ various permutations of the steps 801 through 809.

At step 801, the distal end of a tissue engagement device (e.g., a surgical grasping instrument), such as any of the devices disclosed herein, is introduced inside the body of a patient. Any suitable method for introducing the tissue engagement device is contemplated, including those known in the art for introducing trocars or other small diameter instruments into a patient.

At step 802, the distal end of the instrument is guided toward a region of soft tissue. Any suitable guiding techniques are contemplated, including fluoroscopy methods such as previously mentioned.

At step 803, the distal end of the tissue engagement or grasping instrument is pushed against the region of soft tissue. As previously discussed, in various embodiments, the grasping instrument can include a plurality of engagement (e.g., penetrating) tips that can, in some instances, define a gap into which a thin layer of tissue is received.

At step 804, two or more piercing elements are deployed. The piercing elements can include tips that approach and then bypass one another. The tips may then move to radially extended positions as they pass into the tissue. Step 804 can correspond, for example, to the steps disclosed in FIGS. 13A-13F.

At step 805, the two or more piercing elements are retracted and they redeployed. Step 805, repeated iteratively, can correspond with the method described with respect to FIGS. 15A-15D.

At step 806, the tissue is manipulated while the piercing elements are maintained in the deployed position so as to maintain a grasp on the soft tissue layer. For example, the tissue engaging or grasping device can be pulled in a proximal direction to provide additional space between adjacent tissue layers (e.g., to enlarge the pericardial space). This step can correspond with the stage depicted, for example, in FIGS. 14B and 14C.

At step 807, additional procedures are performed, such as passing a delivery needle through the soft tissue and passing a guidewire through the needle. This step can correspond with the stages depicted, for example, in FIGS. 14C-14E.

At step 808, the soft tissue is released as the piercing elements are retracted to their original position. Stated otherwise, returning the piercing elements to the undeployed state effects a release of the soft tissue.

At step 809, the surgical grasping device is fully removed from the patient. In some instances, the device may be removed over other devices or instruments that may remain in the body. For example, the guidewire and/or instruments introduced into the body over the guidewire may remain in place.

In some instances, steps 801 and 802 are examples of steps or actions that may be required in order to proceed to step 803, in which the engaging instrument or device invention is pressed against the tissue. The steps 803, 804, 806 of the method 820 are described elsewhere herein, and can include the layer engagement methods that use engagement arms that uniquely deploy radially and pass by each other during deployment.

In some instances, step 807 may employ a threaded advancement methodology like that shown in FIGS. 20 and 21, which can provides a controlled means for advancing the puncture needle 301 and a means for the needle 301 to stay in position when the user lets go. This type of advancement mechanism may, in some instances, limit the tactile feedback to the user of the needle tip 302 as it is penetrating through tissue.

FIGS. 27A and 27B depict another embodiment of a tissue engagement device 821. The device 821 includes a different mechanism for maintaining the puncture needle in a desired position. The device 821 includes a handle 820 having main body 822. In FIG. 27B, a puncture needle 823 is shown in channel or lumen 833. A transverse slot 824 constrains brake pad 825 to have only back and forth motion 827. The brake pad 825 has a sloped surface 836 that faces the needle 823. Knob 828 has a threaded shaft 829 that feeds into a threaded opening 832 so that as knob 828 is turned, it rotates about axis 831, which creates the back and forth (e.g., transverse) motion 827. Brake pad 825 only moves in one direction 827, which is preferably transverse to the deployment direction and long axis of puncture needle 823. In this way, then as brake pad 825 presses against needle 823 it does not cause any additional unwanted motion of the needle 823 along its deployment direction (e.g., in a direction into the page in FIG. 27B). The brake pad 825 is connected to threaded shaft 829 so they stay together but the threaded shaft 829 can independently rotate with rotation motion 830 relative to brake pad 825. Alternatively, the brake pad 825 and the threaded shaft 829 may not be integrated into a single unit, but instead may be pressed together by placing a spring (not shown) at the end of transverse slot 824. In this way, the spring (not shown) presses against the end of brake pad 825 and always biases it against the tip of threaded shaft 829. These are just two examples of a feature that allows a user to apply varying amounts of friction to the needle 823. Other devices, mechanisms and techniques can be employed as well without deviating from the spirit and scope of the present disclosure.

The embodiments described above employ two engagement arms. However, other or further embodiments may have as few as 1 actuation arm or more than 2 actuation arms. In embodiments with more than 2 arms, the arms may be arranged in alternate, interleaving layers and may share common pivot pins or posts, or use different pivots. Further, the shapes, sizes and overall construct of the one or more engagement arms can vary depending on particular needs and applications.

Moreover, the embodiments described above use a lever as an actuator. However, other forms of a user interface for moving the actuation rod are contemplated. Any suitable actuation mechanism may be employed, such as, for example, a knob, a sliding button, or any other suitable mechanical interface. Other suitable forms of actuation include pneumatic, electromechanical, or hydraulic for example. In general, any suitable actuation mechanism for transitioning the engagement arms between deployed and undeployed configurations are contemplated.

FIGS. 28A-30 illustrate yet another embodiment of a tissue engagement device 901, which device includes a handle 902, a tube 903, and a tip 904. A lever 905 extends from body 911, and is used to actuate engagement arms 926 and 927 within tip 904. When lever 905 is angled toward tip 904, the engagement arms 926, 927 are retracted. When lever 905 is pivoted away from tip 904, the engagement arms 926, 927 are actuated. Needle assembly 950 attaches to handle 902 using a threaded coupling that joins handle threads 940 with internal threads 960 (see FIG. 30) on adjustment dial 951. Thus, rotating adjustment dial 951 causes needle assembly 950 to advance forward or backward depending on the direction of rotation. A puncture needle 959 (FIG. 30) is attached to assembly 950 and passes through a needle pathway 921 within tube 903.

Figure 29:
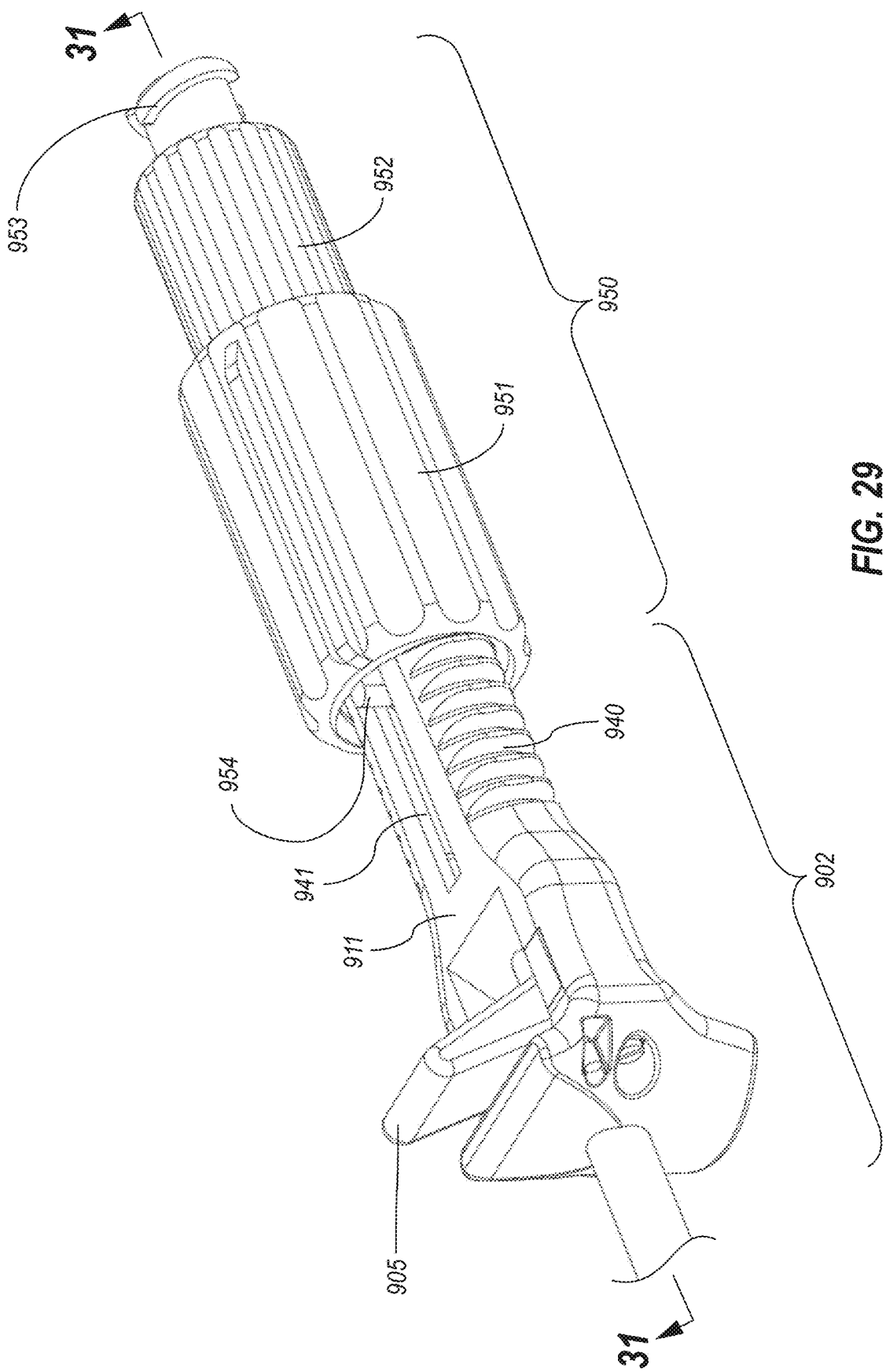
FIG. 29 is a detailed perspective view of a handle portion of the tissue engagement device of FIG. 28A.

FIG. 29 is a detailed view of handle 902 and needle assembly 950. An alignment rib 954 and needle hub 952 are rigidly affixed (e.g., bonded or overmolded) to penetration needle 959. Needle hub 952 features luer lock threads by which a syringe can be attached to needle assembly 950. Adjustment dial 951 is also fixed to assembly 950, but is not rotationally constrained and can freely spin. Alignment rib 954 is sized to slideably fit within handle slot 941 and acts to maintain the orientation of needle 959 as adjustment dial 951 is rotated.

Figure 30:
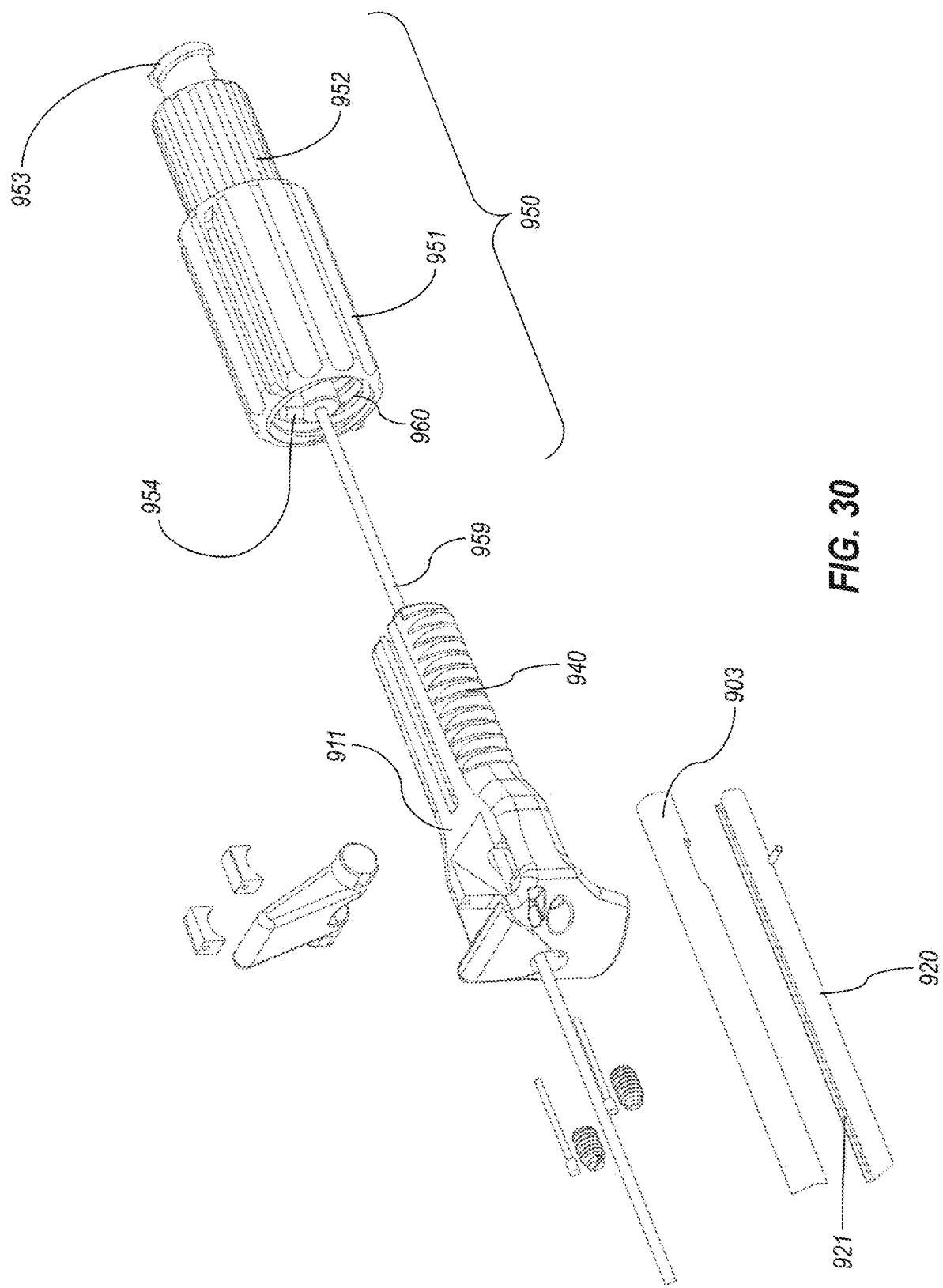
FIG. 30 is an exploded perspective view of the portion of the tissue engagement device depicted in FIG. 29.

FIG. 30 is an exploded, detailed view of handle 902, with needle assembly 950 separated from handle body 911. Needle 959 is affixed to rib 954 and hub 952, and extends through needle passage 921 on connecting rod 920.

Figure 31:
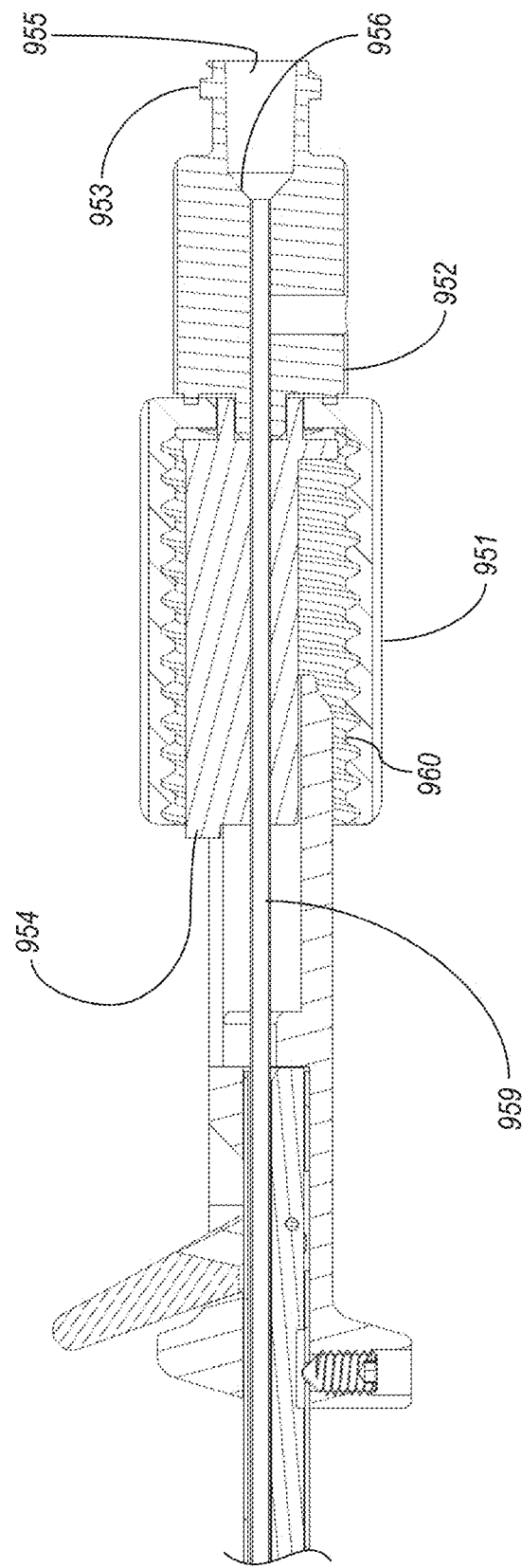
FIG. 31 is a cross-sectional view of the tissue engagement device taken along the view line 31-31 in FIG. 29.

FIG. 31 shows a cross sectional view of handle 902 and needle assembly 950. The position of needle 959 relative to the other components of assembly 950 can be readily seen in this view. Hub 952 is attached to the most proximal location of needle and ends at the female luer cavity 955. A taper 956 from cavity 955 provides a transition to ease the initial insertion of a guidewire (not shown).

Figure 32:
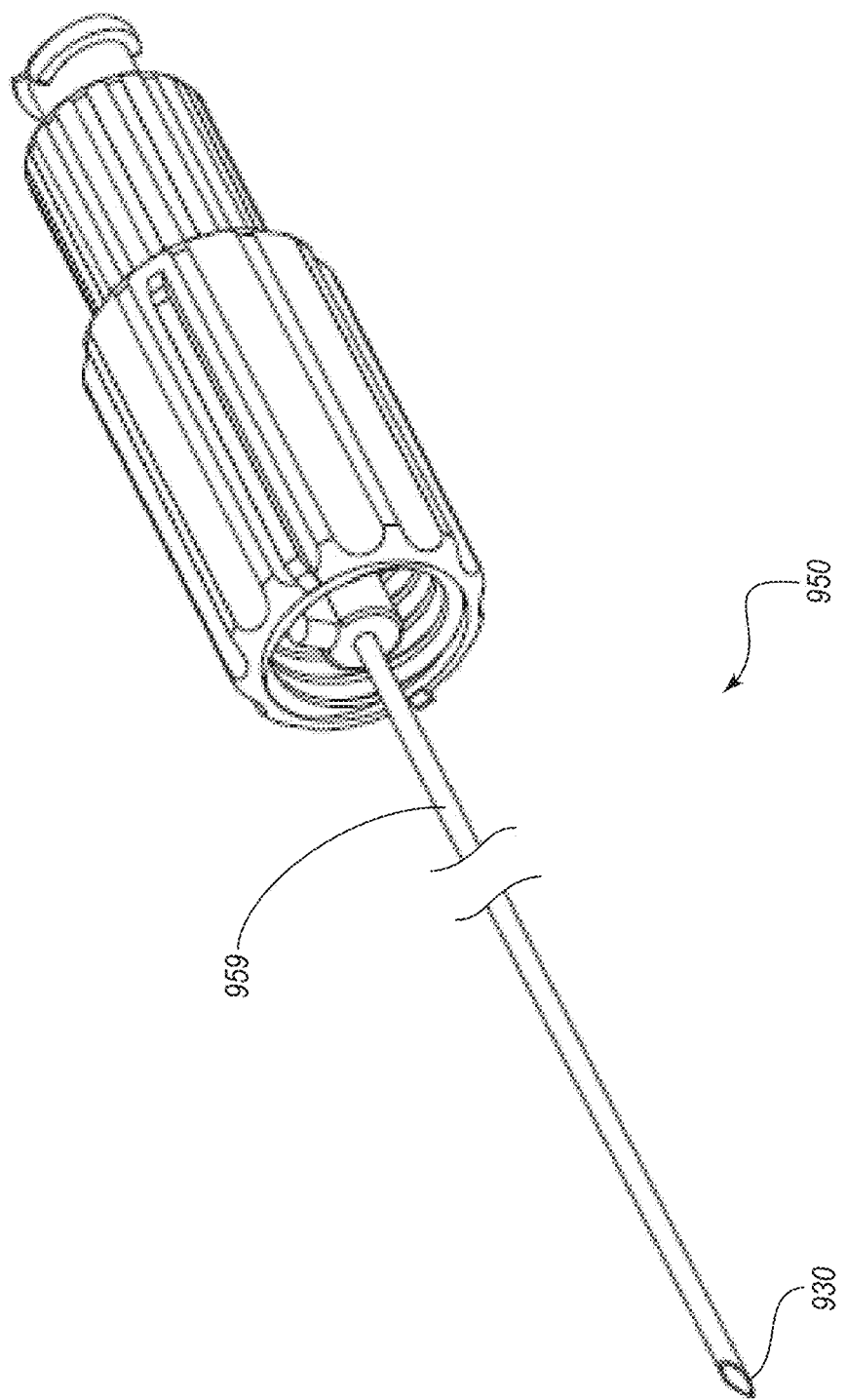
FIG. 32 is a view of a detachable needle assembly that attaches to the tissue engagement device of FIG. 28.
Figure 33:
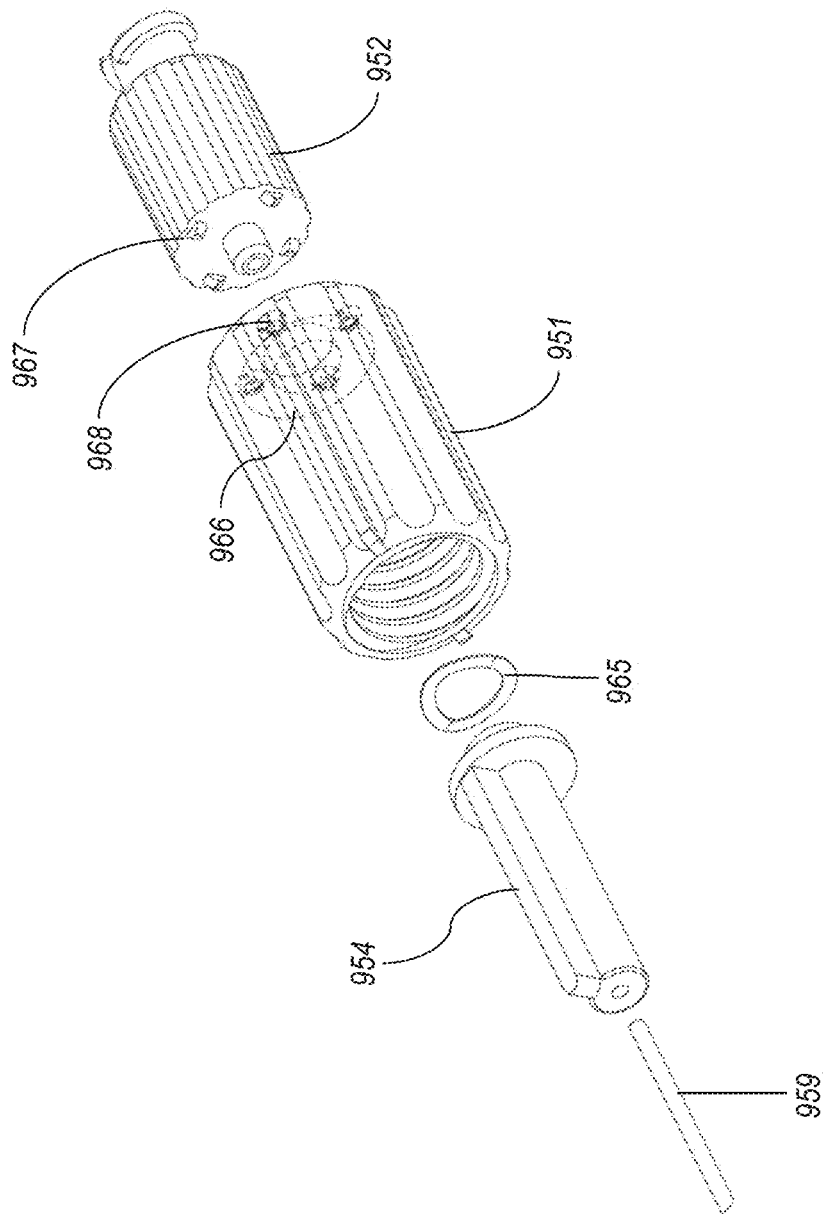
FIG. 33 is a detailed, exploded view of a proximal end of the detachable needle.

FIG. 32 is another view of needle assembly 950, shown in its entirety, including the beveled tip 930 in needle 959. FIG. 33 shows and exploded view of needle assembly 950 that illustrates a mechanism for rotationally indexing the adjustment dial 951. This is achieved with a wave spring 965 that is positioned between rib 954 and internal wall 966 on dial 951; and a set of angularly spaced detents 967 and pockets 968. Spring 965 pushes dial 951 against hub 952 such that when the detents 967 and pocket 968 are aligned, the dial 951 is lightly held in position. By applying a suitable pitch on the threads 940 (shown in FIG. 30) and 960, the indexing mechanism can assist the user in gauging the advancement distance of the needle tip. For example with index positions 90 degrees apart, a thread pitch of 4 millimeters per revolution would mean that the needle advances 1 millimeter each time dial 951 is rotated to the next index stop. Fixed-distance markings on handle 902 can provide additional indicators of the advancement distance of needle assembly 950.

Figure 34:
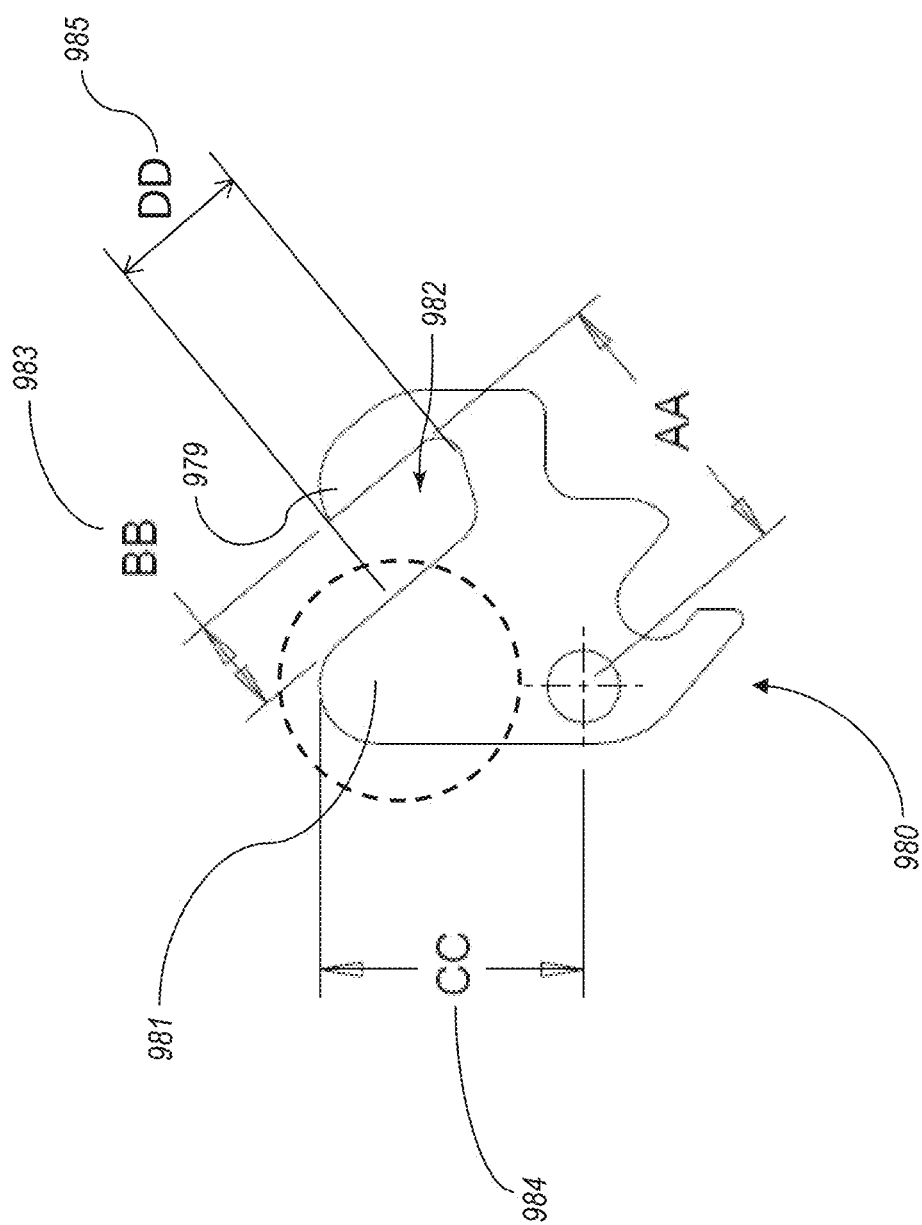
FIG. 34 depicts an embodiment of an engagement arm that is compatible with tissue engagement devices, the engagement arm featuring a shield protrusion capable of preventing inadvertent tissue injury when pulling the engagement arm while it is actuated and/or limiting the penetration depth of the arm into tissue.

FIG. 34 illustrates another embodiment of an engagement arm 980 that is compatible with embodiments disclosed herein. In this design, the engagement arm 980 features a protrusion 981 (encircled by dotted circle) that provides additional advantageous properties. The engagement arm 980 defines a gap 982 with width BB and length DD. This arrangement can assist in controlling a penetration depth of tip 979 by limiting the amount of tissue that can fit into the gap 982. A height CC of the protrusion 981 can further provide control by limiting the engagement of tip 979 into tissue prior to the actuation of arm 980. Stated otherwise, the protrusion 981 can inhibit the tip 979 from coming into contact with the target tissue layer prior to actuation of the arm 980.

Figure 35A:
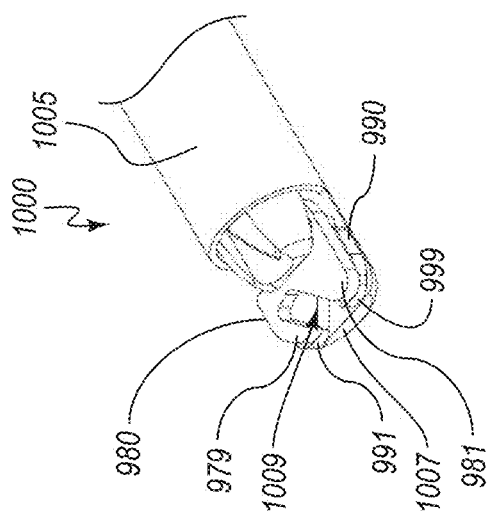
FIGS. 35A-35F depict various stages of deployment of another embodiment of a tissue engagement device that includes alternate engagement arms with shield protrusions.
Figure 35C:
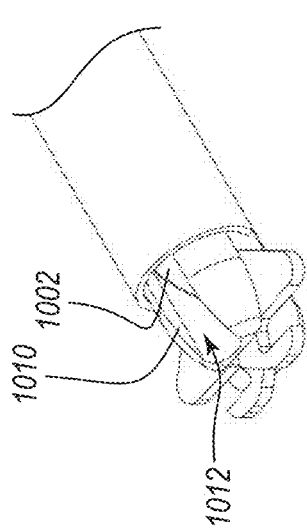
Figure 35B:
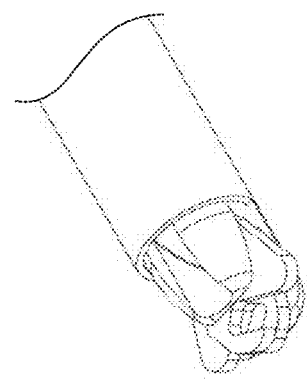
Figure 35F:
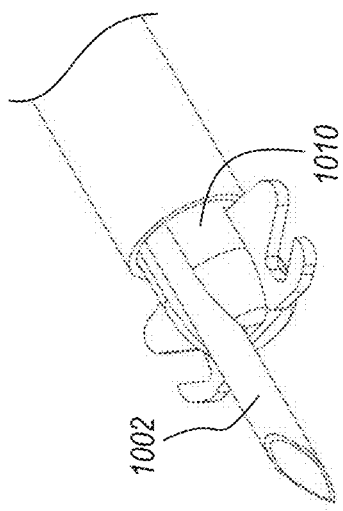
Figure 35E:
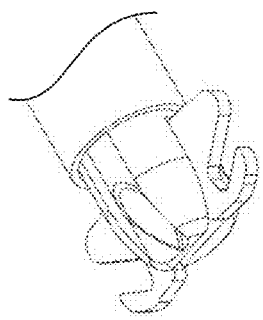
Figure 35D:
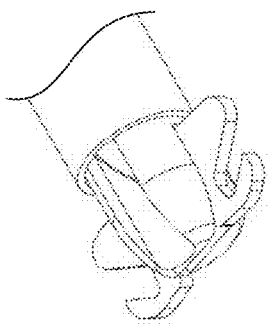

FIGS. 35A-35F depict a device 1000 that includes the engagement arm 980 and an additional engagement arm 990 of the same configuration (but flipped 180 degrees). These drawings depict various stages of deployment of the arms 980, 990 from full retraction (FIG. 35A) to full actuation (FIG. 35D). Deployment of a puncturing needle 1002 is shown in FIGS. 35D-35F, with the needle being fully retracted in FIG. 35D and fully deployed in FIG. 35F. In some instances, it can be preferable to fully deploy the engagement arms 980, 990 to the orientation shown in FIG. 35D prior to deploying the needle 1002 in the manners shown in FIGS. 35D-35F.

As mentioned, the engagement arm 990 can be identical to the arm 980, but may be flipped over such that tips 979, 999 face inwardly (e.g., toward a longitudinal axis of the device each other when in the retracted orientation. Stated otherwise, arm 980 can lie alongside arm 990, but in a mirrored orientation. In the orientation depicted in FIG. 35A, the arm tip 979 on arm 980 is opposed by protrusion 991 on arm 990. For example, a distal edge of the tip 979 of the arm 980 can be substantially flush with a distal edge of the protrusion 991 of the arm 990 in the illustrated orientation. Likewise, a distal edge of the tip 999 of the arm 990 can be substantially flush with a distal edge of the protrusion 981 of the arm 980. Thus, it can be seen that the protrusions 981 and 991 together limit the amount of initial penetration that is possible when the device 1000 is applied against tissue in the illustrated orientation (e.g. in the retracted or undeployed state).

In the illustrated embodiment, the distal edges of the tip 979 and the protrusion 981 of the arm 980 are at approximately the same axial position at or near a distal end 1007 of the tube 1005. Similarly, the distal edges of the tip 999 and the protrusion 991 of the arm 990 are at approximately the same axial position. In the illustrated embodiment, these edges are substantially flush with the distal surface 1007 of the tube 1005. Such an arrangement can further control a manner and/or an amount of a tissue layer that can be received into a gap 1009 or tissue receiving region. This can also control a manner in which portion of the tissue layer that is received therein is engaged as the arms 980, 990 are deployed (FIGS. 35B-35E).

As previously mentioned, FIG. 35D shows the arms 980, 990 in their fully actuated positions and prior to the deployment of the puncture needle 102. The device 1000 can include an actuation rod 1010 that can effect deployment of the arms 980, 990 in manners such as described above. The actuation rod 1010 can define a channel or lumen 1012 within which the needle 1002 is carried. In the illustrated embodiment, the actuation rod 1010 can be advanced distally independent of the needle 1002. Once the actuation rod 1010 has completed deployment of the arms 980, 990, the needle 1002 can be advanced distally through the channel 1012. The needle 1002 can be advanced beyond the distal end of the actuation rod 1010, as shown in FIG. 35F.

In some instances the protrusions 981, 991 can be advantageous in stages such as that depicted in FIG. 35D. In such circumstances, the additional material of protrusions 981 and 991 can enhance the ability to see the actuated arms with imaging methods such as fluoroscopy, which are commonly used during procedures for which the device 1000 is well suited. Yet another advantage is that the protrusions can act as safety guards by shielding the tip points (e.g. tip 979 of arm 980). For example, if the device is withdrawn while the arms are inadvertently actuated, the protrusions will minimize unintended tissue trauma by diverting tissue away and around the tips 979, 999 during retraction of the device 1000. In some instances, the protrusions 981, 991 could assist in or even effectuate partial or full retraction of the arms in such situations, as drawing the protrusions 981, 991 proximally past tissue could force them to rotate partially or fully into the retracted state.

Figure 36:
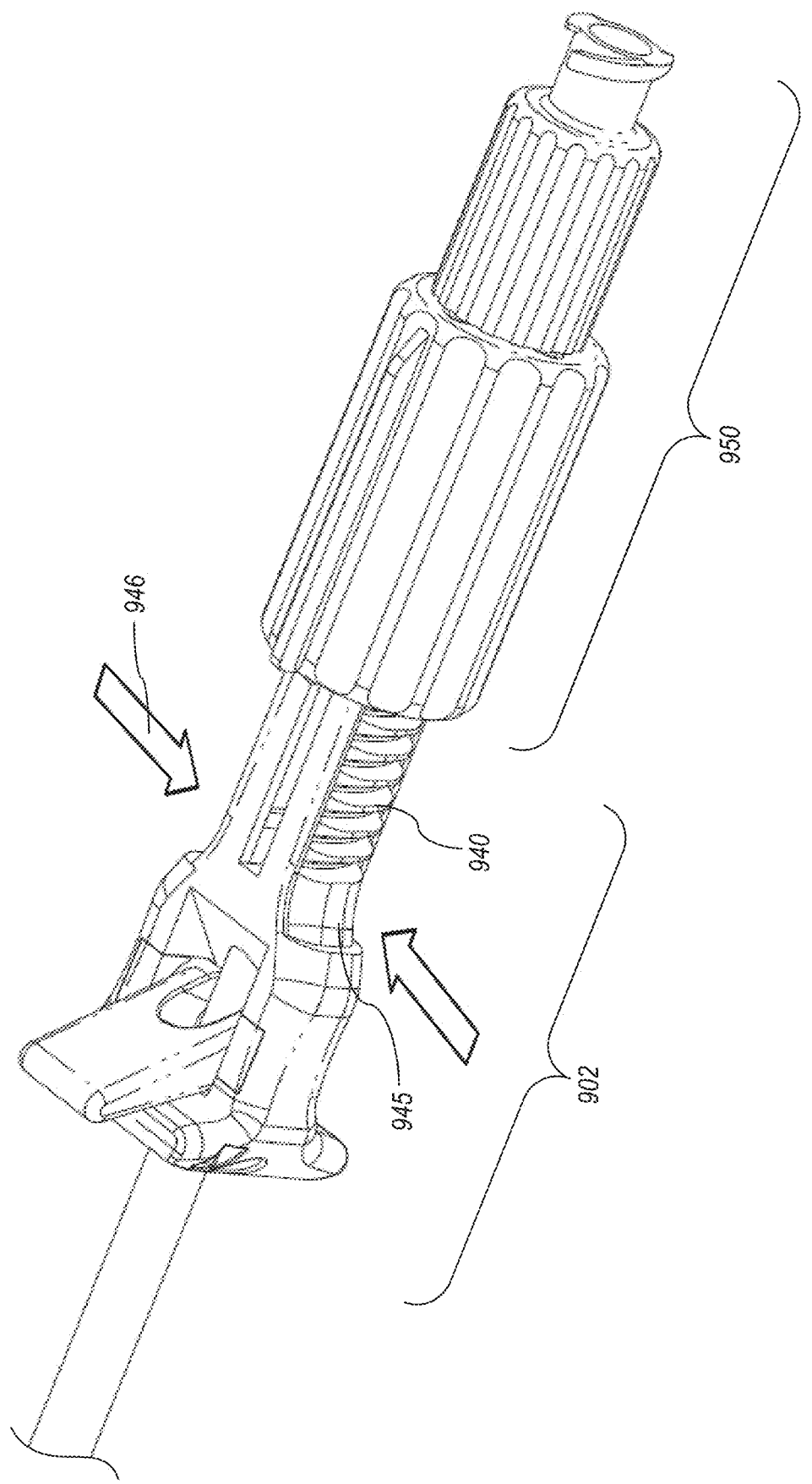
FIG. 36 depicts an illustrative rapid retraction mechanism adapted to a threaded coupling between a needle assembly and a device handle.

In some instance, the ability to rapidly retract the needle during the procedure—after delivery of the guidewire, for example—may be desired by the user. FIG. 36 depicts an example of a rapid retraction mechanism, adapted to the threaded coupling between the needle assembly 950 and the device handle 902. Here, handle threads 940 are located on a slideable segment 945 which can be displaced inwardly by applying a pinching force along direction 946. During normal use, internal springs (not visible) apply an outward biasing force that maintains engagement between handle threads 940 and dial threads 960. Thus, needle assembly 950 can be quickly disengaged and removed by applying the pinching force along direction 946 and retracting assembly 950. Additionally a biasing element, such as a coil spring, may be inserted between needle assembly 950 and handle 902 such that needle assembly 950 is urged away during retraction.

Figure 37:
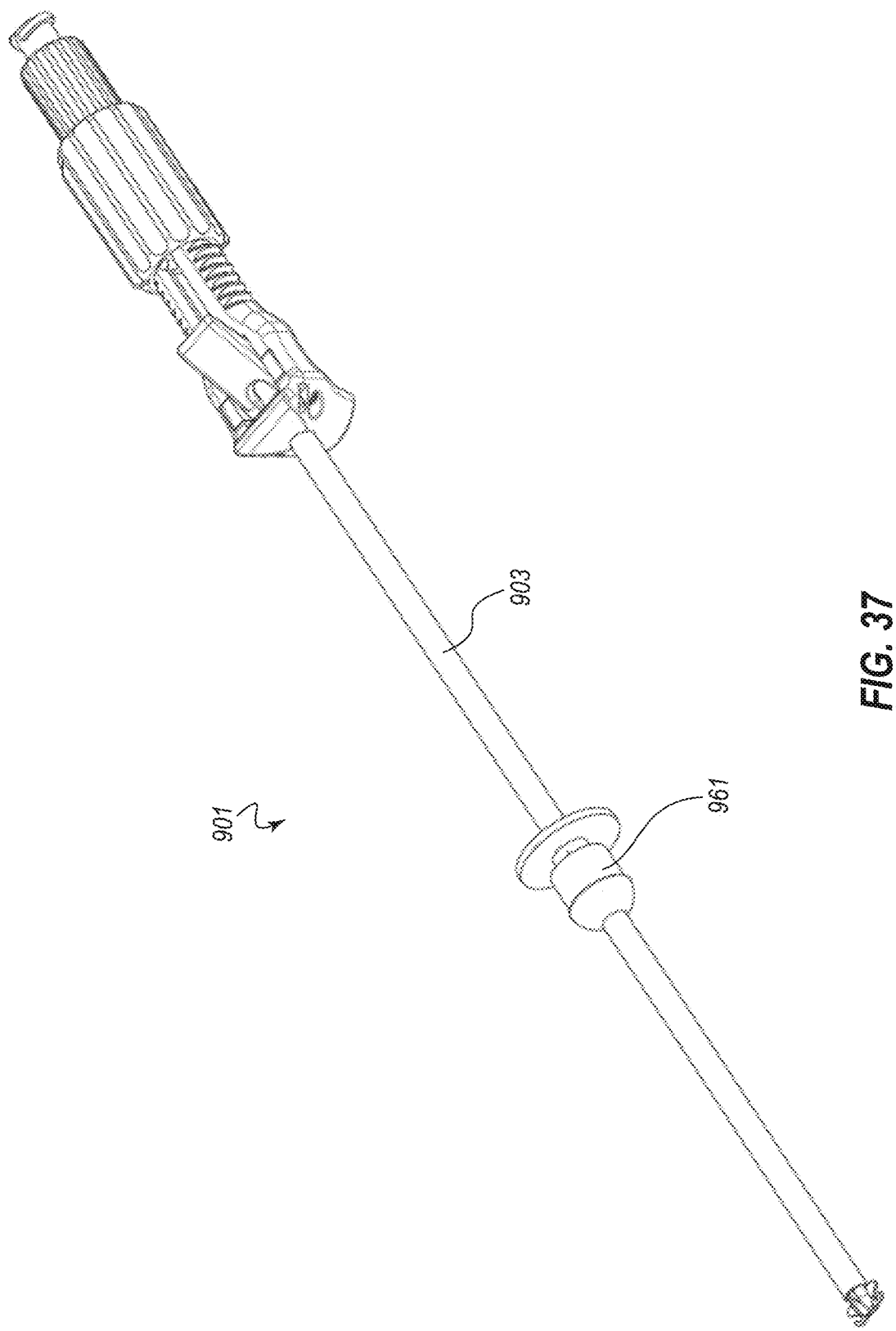
FIG. 37 depicts an embodiment of a device having a lockable collar that fits over a tube shaft.

Referring to FIG. 37, another accessory feature for assisting with user handling of the device is described. FIG. 37 illustrates a slideable and lockable collar 961 that fits over tube 903. Means for locking collar 961 to tube 903 include friction, collets, clamping or other common means for fixing an object axially mounting on a shaft. In some instances, after a user has successfully actuated engagement arms (in this embodiment 980 and 990), and applied traction to the soft tissue, the user may wish to maintain such traction while performing further steps, such as insertion of the guidewire. Rather than manually holding such traction, collar 961 may be slid distally along tube 903 until it is against the patient's skin. Then collar 961 may be locked in position against the skin. This will maintain the traction on the soft tissue, and frees the user's hand for performing subsequent steps of a procedure.

In the embodiment shown in FIG. 37, the shaft 903 of device 901 slides into lockable collar 961. However, lockable collar 961 may have an opening along its length so that it can be slipped onto the shaft 903 of device 901 and taken off without having to slide the device through lockable collar 961. This can be advantageous if, for example, the lockable collar 961 is to be removed while the device 901 is inserted in a patient.

Embodiments have been described herein in the context of pericardial access, but discussion of this context should not be considered limiting as other uses and applications are contemplated. For example, some embodiments are used in endoscopic third ventriculostomy (ETV), which requires lifting the floor of the third ventricle from the underlying tissue to be able to create a hole through it. Another exemplary application is in laparoscopic access into the peritoneal space that requires pulling tissue layers, such as peritoneum, from underlying tissue layers or organs. The device and techniques disclosed herein can be further used in various other applications and procedures.

Advantageously, embodiments described herein have features, geometry, and structure that allow the tissue engagement devices to be mass produced cost effectively. Preferred manufacturing methods for the main components include metal stamping, plastic molding, machining, and laser cutting. Other manufacturing methods known to those of ordinary skill in the art are also contemplated.

The present invention has now been described with reference to several illustrative embodiments thereof. The foregoing disclosure has been provided for clarity of understanding by those skilled in the art. No unnecessary limitations should be taken from the foregoing disclosure. It will be apparent to those skilled in the art that changes can be made in the illustrative embodiments described herein without departing from the scope of the present invention. Thus, the scope of the present invention should not be limited to the illustrative structures and methods described herein, but only by the structures and methods described by the language of the claims and the equivalents of those claimed structures and methods.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially flush" is recited with respect to a feature, it is understood that in further embodiments, the feature can have a precisely flush orientation.

Any reference throughout this specification to "certain embodiments" or the like means that a particular feature, structure or characteristic described in connection with that embodiment is included in at least one embodiment. Thus, the quoted phrases, or variations thereof, as recited throughout this specification are not necessarily all referring to the same embodiment or embodiments.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112(f). Embodiments of the invention in which an exclusive property or privilege is claimed are defined as follows.

The invention claimed is:

1. A tissue engagement device, comprising:
    a lumen tube having a maximum exterior width;
    a proximal end and a distal end; and
    at least two adjacent engagement arms each including a piercing tip and a curved non-piercing edge adjacent the piercing tip, wherein the at least two adjacent engagement arms are configured to move between (i) a retracted undeployed orientation in which the curved non-piercing edges of the two adjacent engagement arms extend out beyond an end of the lumen tube to define a lateral width less than the maximum exterior width of the lumen tube and the piercing tips of the at least two adjacent engagement arms face each other to define a gap therebetween and each curved non-piercing edge is oriented to pass over and deflect tissue, without penetrating the tissue, when the distal end is pressed against the tissue, and (ii) an actuated orientation in which each curved non-piercing edge faces distally from the lumen tube, throughout a transition from the retracted undeployed orientation to the actuated orientation, and the piercing tips of the at least two adjacent engagement arms are moved towards each other to eliminate the gap and then cross over each other to end in a full actuated orientation facing away from each other, such that the curved non-piercing edges are spaced from each other by a distance greater than the maximum exterior width.

2. The device of claim 1, wherein the gap further defines a space configured to receive a bulge of the tissue during actuation.

3. The device of claim 1, further comprising a puncture needle that comprises a tip configured to puncture through a tissue layer after the tissue layer has been engaged by the piercing tips of the at least two adjacent engagement arms.

4. The device of claim 3, wherein a pathway of the puncture needle is either parallel to or collinear with a central axis of the lumen tube.

5. The device of claim 4, wherein the pathway extends between the at least two adjacent engagement arms.

6. The device of claim 1, wherein the at least two adjacent engagement arms are actuated by a lever, a knob, or a sliding button.

7. The device of claim 1, wherein the at least two adjacent engagement arms are actuated by an actuator rod.

8. The device of claim 1, wherein the piercing tips of the at least two adjacent engagement arms are each sharpened along one or more bevel planes.

9. The device of claim 1, wherein the movement of the piercing tips of the at least two adjacent engagement arms includes rotational movement or pivotal movement.

10. The device of claim 1, wherein the at least two adjacent engagement arms each include a slot in which a fixed guide post slides to cam the at least two adjacent engagement arms from the retracted undeployed orientation to the actuated orientation.

11. The device of claim 1, wherein the at least two adjacent engagement arms includes more than two adjacent engagement arms.

12. The device of claim 1, wherein each of the at least two adjacent engagement arms further include a flat shelf portion configured for a tissue layer to rest on during the actuated orientation.

13. A tissue engagement device, comprising:
a handle;
a tube having a lumen and a maximum exterior width, with the tube operatively coupled to the handle; and
a plurality of engagement arms each including a piercing tip and a curved non-piercing edge adjacent the piercing tip, wherein two adjacent engagement arms of the plurality of engagement arms are displaceable between:
(i) a retracted undeployed stage in which the curved non-piercing edges of the two adjacent engagement arms extend out beyond an end of the lumen to define a lateral width less than the maximum exterior width of the lumen and the piercing tips of the two adjacent engagement arms face each another to define a gap therebetween, and wherein the curved non-piercing edge of each of the two adjacent engagement arms is oriented to pass over and deflect tissue, without penetrating the tissue, when the distal end is pressed against the tissue; and
(ii) an actuated stage in which the curved non-piercing edge of each of the two adjacent arms faces distally from the tube, throughout a transition from the retracted undeployed stage to the actuated stage, and the piercing tips of the two adjacent engagement arms are displaced towards each other to eliminate the gap and then cross over each other to face away from each another in a full actuated stage such that the curved non-piercing edges are spaced from each other by a distance greater than the maximum exterior width.

14. The device of claim 13, wherein the gap further defines a space configured to receive a bulge of the tissue during actuation.

15. The device of claim 13, further comprising a puncture needle that comprises a tip configured to puncture through a tissue layer after the tissue layer has been engaged by the piercing tips of the two adjacent engagement arms.

16. The device of claim 15, wherein a pathway of the puncture needle is either parallel to or collinear with a central axis of the tube.

17. The device of claim 16, wherein the pathway extends between the two adjacent engagement arms.

18. The device of claim 13, wherein the two adjacent engagement arms are actuated by a lever, a knob, or a sliding button.

19. The device of claim 13, wherein the two adjacent engagement arms are actuated by an actuator rod.

20. The device of claim 13, wherein the piercing tips of the two adjacent engagement arms are each sharpened along one or more bevel planes.

21. The device of claim 13, wherein the displacement of the piercing tips of the two adjacent engagement arms includes rotational displacement or pivotal displacement.

22. The device of claim 13, wherein the two adjacent engagement arms each include a slot in which a fixed guide post slides to cam the two adjacent engagement arms from the retracted undeployed stage to the actuated stage.

23. The device of claim 13, wherein each of the two adjacent engagement arms further include a flat shelf portion configured for a tissue layer to rest on during the actuated stage.

* * * * *